(12) United States Patent
Weller et al.

(10) Patent No.: US 10,584,387 B2
(45) Date of Patent: Mar. 10, 2020

(54) DETECTION OF HEPATITIS DELTA VIRUS (HDV) FOR THE DIAGNOSIS AND TREATMENT OF SJÖGREN'S SYNDROME AND LYMPHOMA

(71) Applicant: The U.S.A., as represented by the Secretary, Department of Health and Human Services, Bethesda, MD (US)

(72) Inventors: Melodie L. Weller, Silver Spring, MD (US); John A. Chiorini, Dayton, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 621 days.

(21) Appl. No.: 15/027,546

(22) PCT Filed: Oct. 9, 2014

(86) PCT No.: PCT/US2014/059825
§ 371 (c)(1),
(2) Date: Apr. 6, 2016

(87) PCT Pub. No.: WO2015/054451
PCT Pub. Date: Apr. 16, 2015

(65) Prior Publication Data
US 2016/0244846 A1   Aug. 25, 2016

Related U.S. Application Data

(60) Provisional application No. 61/888,706, filed on Oct. 9, 2013, provisional application No. 62/011,962, filed on Jun. 13, 2014.

(51) Int. Cl.
  *C12P 19/34* (2006.01)
  *C12Q 1/6886* (2018.01)
  *C12Q 1/6883* (2018.01)
  *C12Q 1/70* (2006.01)

(52) U.S. Cl.
  CPC ......... *C12Q 1/6886* (2013.01); *C12Q 1/6883* (2013.01); *C12Q 1/706* (2013.01); *C12Q 1/707* (2013.01)

(58) Field of Classification Search
  CPC .... C12Q 1/6883; C12Q 1/6886; C12Q 1/706; C12Q 1/707
  USPC .................................................. 435/6, 91.2
  See application file for complete search history.

(56) References Cited

U.S. PATENT DOCUMENTS

2016/0032411 A1 * 2/2016 Kodani ............... C12Q 1/706
                                                        435/5

OTHER PUBLICATIONS

Weller et al., (Pathog. Immun., 1(1): 12-40, May (Year: 2016).*
Mayeux et al., NeuroRx, 1, pp. 182-18 (Year: 2004).*
Wilelke et al., Arthritis Research and Therapy, 9, R115, 1-7, (Year: 2007).*
Dispenza et al., Brazilian Journal of Otorhinolaryngology, 2011; 77(5): 639-44. (Year: 2011).*
Yamada et al., J. Neurol. Neurosurg. Psychiatry, 76: 576-578, (Year: 2005).*
Garcia-Carrasco et al., Int. J. Clin. Rheumtol.; 7(6): 651-659, Dec. (Year: 2012).*
Pimenta et al., Cancers, 6: 969-997 (Year: 2014).*
Altuglu et al., "Hepatitis delta virus (HDV) genotypes in patients with chronic hepatitis: molecular epidemiology of HDV in Turkey," *Int J Infect Dis* 11:58-62, 2007.
Vitali et al., "Classification criteria for Sjogren's syndrome: a revised version of the European criteria proposed by the American-European Consensus Group," *Ann Rheum Dis* 61:554-558, 2002.
Ali et al., "Hepatitis C Infection: A Systemic Disease with Extrahepatic Manifestations," *Cleveland Clinic J. Med.*, vol. 72:1005-1019, 2005.
Andersen et al., "Reactivation of Hepatitis D Virus after Chemotherapy for Diffuse Large B Cell Lymphoma Despite Lamivudine Prophylaxis," *Int. J. Hematol.*, vol. 92:378-380, 2010.
Ardeleanu et al., "Chronic Lymphoproliferative Diseases Associated with Chronic Hepatitic Viral Infections," *Virchows Arch.*, vol. 457:191, 2010.
Bordier et al., "In Vivo Antiviral Efficacy of Prenylation Inhibitors Against Hepatitis Delta Virus," *J. Clin. Invest.*, vol. 112:407-414, 2003.
Chang et al., "Action of Inhibitors on Accumulation of Processed Hepatitis Delta Virus RNAs," *J. Virol.*, vol. 80:3205-3214, 2006.
Einav et al., "Prenylation Inhibitors: A Novel Class of Antiviral Agents," *J. Antimicrob. Chemo.*, vol. 52:883-886, 2003.
Gottenberg et al., "Failure to Confirm Coxsackievirus Infection in Primary Sjögren's Syndrome," *Arthritis Rheum.*, vol. 54(6):2026-2028, 2006.
Gomes-Gouvêa et al., "Hepatitis D and B Virus Genotypes in Chronically Infected Patients from the Eastern Amazon Basin," *Acta Tropica*, vol. 106:149-155, 2008.

(Continued)

*Primary Examiner* — Cynthia B Wilder
(74) *Attorney, Agent, or Firm* — Klarquist Sparkman, LLP

(57) ABSTRACT

Viral infection has been suspected in the development of primary Sjögren's syndrome (pSS). Using a custom viral microarray, hepatitis delta virus (HDV) genomes and antigens were detected in minor salivary glands of patients with pSS. Expression of HDV antigens in healthy mice led to a Sjögren's syndrome-like pathogenesis characterized by a reduction in salivary flow, increase in lymphocytic foci, and the development of an autoantibody profile similar to HDV-positive patients. Also described herein is the detection of HDV in patients diagnosed with lymphoma. Expression of HDV antigen in healthy mice resulted in the development of tertiary lymphoid structures characteristic of the early stages of lymphoma. A sensitive, nested qPCR assay to detect HDV transcript and/or HDV genome in patient samples is also described.

29 Claims, 18 Drawing Sheets
Specification includes a Sequence Listing.

(56) References Cited

OTHER PUBLICATIONS

Horiuchi et al., "Possible Involvement of IL-12 Expression by Epstein-Barr Virus in Sjögren's Syndrome," *J. Clin. Pathol.*, vol. 52:833-837, 1999.

Jadali et al., "Autoimmune Diseases Co-Existing with Hepatitis C Virus Infection," *Iran J. Allergy Asthma Immunol.*, vol. 9:191-206, 2010.

Katsoulidou et al., "Development and Assessment of a Novel Real-Time PCR Assay for Quantification of Hepatitis D Virus RNA to Study Viral Kinetics in Chronic Hepatitis D," *J. Viral Hepatitis*, vol. 20:256-262, 2013.

Marcos et al., "Chronic Hepatitis B Virus Infection in Sjögren's Syndrome. Prevalence and Clinical Significance in 603 Patients," *Autoimmunity Reviews*, vol. 8:616-620, 2009.

Molagic et al., "Preliminary Data on the Involvement of B, C and D Hepatitis Viruses in the Etiopathogenesis of Chronic Lymphoproliferative Syndromes in Romania," *Rom. J. Intern. Med.*, vol. 47:25-34, 2009.

Obermayer-Straub et al., "Hepatitis C and D, Retroviruses and Autoimmune Manifestations," *J. Autoimmun.*, vol. 16:275-285, 2001.

Saito et al., "Detection of Epstein-Barr Virus DNA by Polymerase Chain Reaction in Blood and Tissue Biopsies from Patients with Sjögren's Syndrome," *J. Exp. Med.*, vol. 169:2191-2198, 1989.

Taylor et al., "Origin of Hepatitis δ Virus," *Future Microbiol*, vol. 5:393-402, 2010.

Triantafyllopoulou et al., "Evidence for Coxsackievirus Infection in Primary Sjögren's Syndrome," *Arthritis Rheum.*, vol. 50:2897-2902, 2004.

Vergani et al., "Autoimmune Manifestations in Viral Hepatitis," *Semin. Immunopathol.*, vol. 35:73-85, 2013.

Vladareanu et al., "Retrospective and Prospective Analysis on the Impact of Hepatitis Viruses on Chronic Lymphoproliferative Disorders," *Haematologica*, vol. 94:397-398, 2009.

Vladareanu et al., "The Impact of Hepatitis Viruses on Chronic Lymphoproliferative Disorders—Preliminary Results," *J. Med. Life*, vol. 3:320-329, 2010.

Witzig et al., "Multi-institutional phase 2 study of the farnesyltransferase inhibitor tipifarnib (R115777) in patients with relapsed and refractory lymphomas," *Blood*, vol. 118(18):4882-4889, 2011.

GenBank Accession No. AJ000558, "Hepatitis D virus complete genome," deposited Jul. 31, 1997.

\* cited by examiner

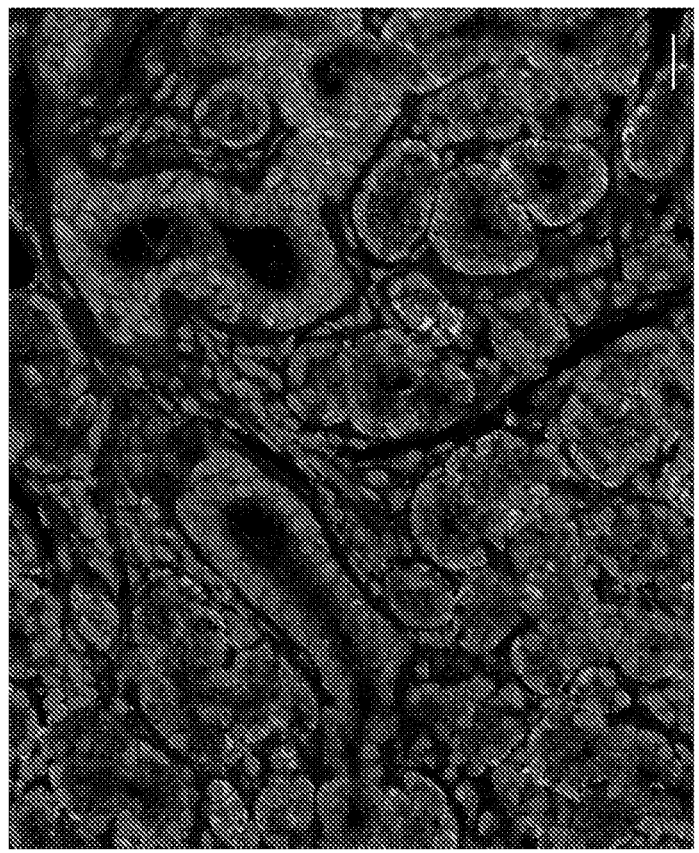
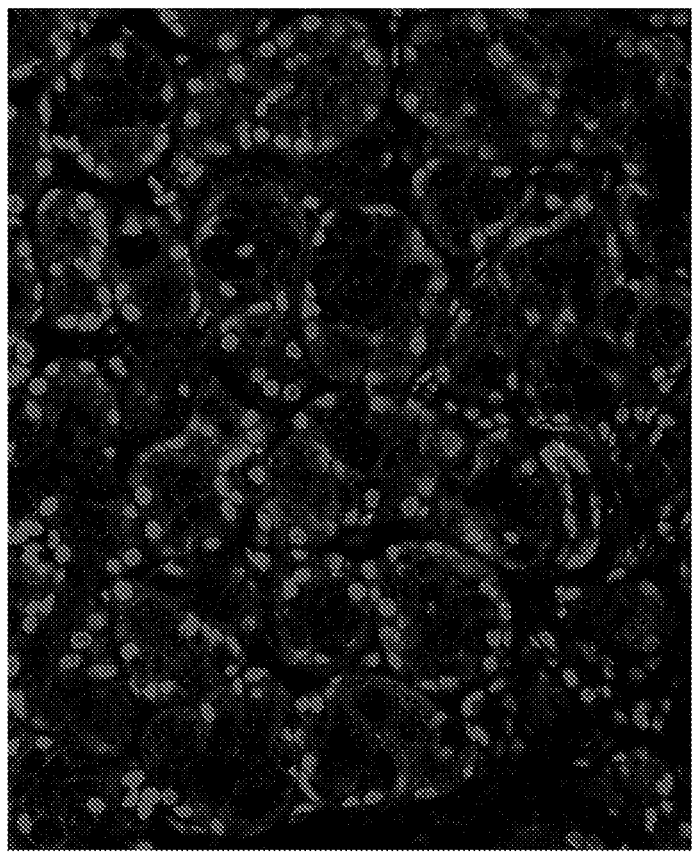
FIG. 1B

FIG. 1C

```
pSS    1     GGAGATGCCATGCCGACCCGAAGAGGAAAGAAGGACGCGAGACGCAAACCTGTGAGTGGA    60
             ||||||||||||||||||||||||||||||||||||||||||||||||||||||||||||
HDV    881   GGAGATGCCATGCCGACCCGAAGAGGAAAGAAGGACGCGAGACGCAAACCTGTGAGTGGA    940 pSS    61    ANCCCGCTTTATTCACTGGGGTCGACAACTCTGGGGAGAAAAGGGCGGATCGGCTGGGAA   120
             | ||||||||||||||||||||||||||||||||||||||||||||||||||||||||||
HDV    941   AACCCGCTTTATTCACTGGGGTCGACAACTCTGGGGAGAAAAGGGCGGATCGGCTGGGAA   1000 pSS    121   GAGTATATCCCATGGAAATCCCTGGTTTCCCCTGATGTCCAGCCCCTCCCCGGTCCGAGA   180
             ||||||||||||||||||||||||||||||||||||||||||||||||||||||||||||
HDV    1001  GAGTATATCCCATGGAAATCCCTGGTTTCCCCTGATGTCCAGCCCCTCCCCGGTCCGAGA   1060 pSS    181   GAAGGGGGACTCCGGGACTCCCTGCAGATTGGGGACGAAGCCGCCCCCGGGCGCTCCCCT   240
             ||||||||||||||||||||||||||||||||||||||||||||||||||||||||||||
HDV    1061  GAAGGGGGACTCCGGGACTCCCTGCAGATTGGGGACGAAGCCGCCCCCGGGCGCTCCCCT   1120 pSS    241   CGATCCACCTTCGAGGGGGTTCACACCCCCAACCGGCGGGCCGGCTA ctcttcttccct   300
             ||||||||||||||||||||||||||||||||||||||||||||||| ||||||||||||
HDV    1121  CGATCCACCTTCGAGGGGGTTCACACCCCCAACCGGCGGGCCGGCTACTCTTCTTTCCCT   1180 pSS    301   cctctgtcttcctcggtcaacctcctgagttcctcttcttcctcctt GCTGAGGNTCNT   360
             ||||||||||||||||||||||||||||||||||||||||||||||| |||||||| | |
HDV    1181  TCTCTCGTCTTCCTCGGTCAACCTCCTGAGTTCCTCTTCTTCCTCCTTGCTGAGGTTCTT   1240 pSS    361   GCCTCCCGCCGATAGCTGCTTCTTCTTGTTCTCGAGGGCCTTCCTTCGTCGGTGATCCTG   420
             ||||||||||||||||||||||||||||||||||||||||||||||||||||||||||||
HDV    1241  GCCTCCCGCCGATAGCTGCTTCTTCTTGTTCTCGAGGGCCTTCCTTCGTCGGTGATCCTG   1300 pSS    421   CCNCTCCTTGT   431
             || |||||||||
HDV    1301  CCTCTCCTTGT   1311
```

```
M21012     GAGATGCCATGCCGACCCGAAGAGGAAAGAAGGACGCGAGACGCAAACCTGTGAGTGGAA 60
Contig_7   -AGATGCCATGCCGACCCGAAGAGGAAAGAAGGACGCGAGACGCAAACCTGTGAGTGGAA 59
Contig_8   GAGATGCCATGCCGACCCGAAGAGGAAAGAAGGACGCGAGACGCAAACCTGTGAGTGGNA 60
Contig_9   GAGATGCCATGCCGACCCGAAGAGGAAAGAAGGACGCGAGACNCNAACCTGTGAGTGGNA 60
Contig_10  GAGATGCCATGCCGACCCGAAGAGGAAAGAAGGACGCGAGACGCAAACCTGTGAGTGGNA 60
           ********************************************.* *********** *

M21012     ACCCGCTTTATTCACTGGGGTCGACAACTCTGGGGAGAAAAGGGCGGATCGGCTGGGAAG 120
Contig_7   ACCCGCTTTATTCACTGGGGTCGACAACTCTGGGGAGAAAAGGGCGGATCGGCTGGGAAG 119
Contig_8   ACCCGCTTTATTCACTGGGGTCGACAAYTCTGGGGAGAAAAGGGCGGATCGGCTGGGAAG 120
Contig_9   ACCCGCTTTATTCACTGGGGTCGACAACTCTGGGGAGAAAAGGGCGGATCGGCTGGGAAG 120
Contig_10  ACCCGCTTTATTCACTGGGGTCGACAACTCTGGGGAGAAAAGGGCGGATCGGCTGGGAAG 120
           ************************** ********************************

M21012     AGTATATCCTATGGAAATCCCTGGTTTCCCCTGATGTCCAGCCCCTCCCCGGTCCGAGAG 180
Contig_7   AGTATATCCTATGGAAATCCCTGGTTTCCCCTGATGTCCAGCCCCTCCCCGGTCCGAGAG 179
Contig_8   AGTATATCCTATGGAAATCCCTGGTTTCCCCTGATGTCCAGCCCCTCCCCGGKCCGAGAG 180
Contig_9   AGTATATCCATGGAAATCCCTGGTTTCCCCTGATGTCCAGCCCCTCCCCGGTCCGAGAG 180
Contig_10  AGTATATCCATGGAAATCCCTGGTTTCCCCTGATGTCCAGCCCCTCCCCGGTCCGAGAG 180
           *********  ********************************** .*******

M21012     AAGGGGGACTCCGGGACTCCCTGCAGATTGGGGACGAAGCCGCCCCCGGGCGCTCCCCTC 240
Contig_7   AAGGGGGACTCCGGGACTCCCTGCAGATTGGGGACGAAGCCGCCCCCGGGCGCTCCCCTC 239
Contig_8   AAGGGGGACTCCGGGACTCCCTGGAGATTGGGGACGAAGCCGCCCCCGGGCGCTCCCCTC 240
Contig_9   AAGGGGGACTCCGGGACTCCCTGCAGATTGGGGACGAAGCCGCCCCCGGGCGCTCCCCTC 240
Contig_10  AAGGGGGACTCCGGGACTCCCTGCAGATTGGGGACGAAGCCGCCCCCGGGCGCTCCCCTC 240
           *********************** ************************************

M21012     GATCCACCTTCGAGGGGGTTCACACCCCCAACCGGCGGGCCGGCTACTCTTCTTTCCCTT 300
Contig_7   GATCCACCTTCGAGGGGGTTCACACCCCCAACCGGCGGGCCGGCTACTCTTCTTTCCCTT 299
Contig_8   GATCCACCTTCGAGGGGGTTCACACCCCCMACCGGCGGGCCGGCTACTCTTCYTTCCCTT 300
Contig_9   GATCCACCTTCGAGGGGGTTCACACCCCCAACCGGCGGGCCGGCTACTCTTCTTTCCCTT 300
Contig_10  GATCCACCTTCGAGGGGGTTCACACCCCCAACCGGCGGGCCGGCTACTCTTCTTTCCCTT 300
           ***************************** ****************** ******

M21012     CTCTCGTCTTCCTCGGTCAACCTCCTGAGTTCCTCTTCTTCCTCCTTGCTGAGGTTCTTG 360
Contig_7   CTCTCGTCTTCCTCGGTCAACCTCCTGAGTTCCTCTTCTTCCTMCTTGCTGAGGTTCTTG 359
Contig_8   CTCTCGTCTTCCTCGGTCAACCTCCTGARTTCCTCTTCTTCCTCCTTGCTGNAGTTCTTG 360
Contig_9   CTCTCGTCTTCCTCGGTCAACCTCCTGAGTTCCTCTTCTTCCTCCTTGCTGAGGTNCTNG 360
Contig_10  CTCTCGTCTTCCTCGGTCAACCTCCTGAGTTCCTCTTCTTCCTCCTTGCTGAGGNTCTKG 360
           ************************** ************** ****** ,*..**,*

M21012     CCTCCCGCCGATAGCTGCTTCTTCTTGTTCTCGAGGGCCTTCCTT 405
Contig_7   CCTCCCGCCGATAGCTGCTTCTTCTTGTTCTCGAGGGCCTTCCTT 404
Contig_8   CCTCCCGCCGATAGCTGCTTCTTCTTGTTCTCGAGGGCCTTCCTT 405
Contig_9   CCTCCCGCCGATAGCTGCTTCTTCTTGTTCTCGAGGGNCTTCCTT 405
Contig_10  CCTCCCGCCGATAGCTGCTTCTTCTTGTTCTCGAGGGCCTTCCTT 405
           ************************************* ******
```

FIG. 1D

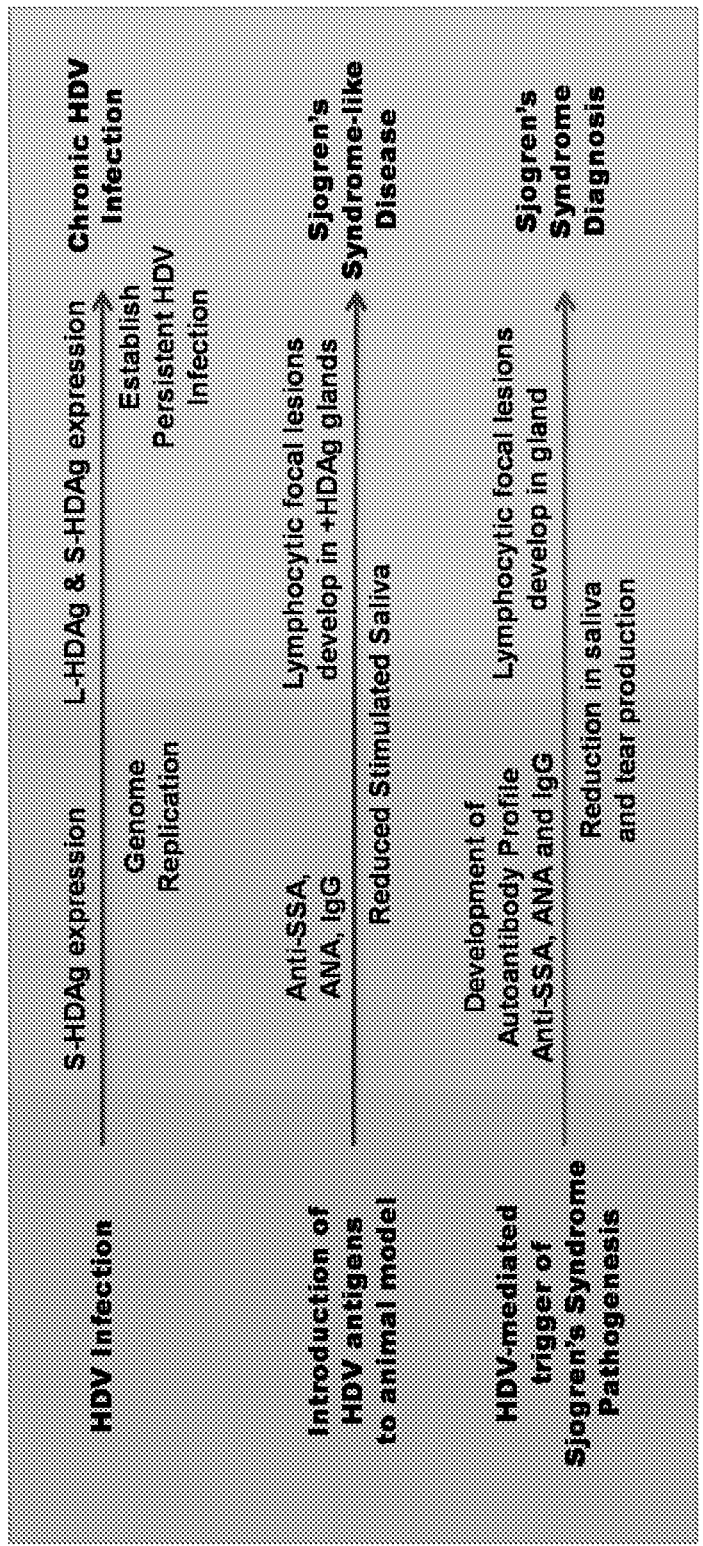
FIG. 5 Proposed pathway to HDV-mediated Sjogren's syndrome pathogenesis Rb IgG Ctrl - Lymphocytes Anti-HDAg - Lymphocytes

… (1)

SEQUENCE LISTING

```
<160> NUMBER OF SEQ ID NOS: 16

<210> SEQ ID NO 1
<211> LENGTH: 1679
<212> TYPE: DNA
<213> ORGANISM: Hepatitis D virus

<400> SEQUENCE: 1
cctgagccaa gttccgagcg aggagacgcg gggggaggat cagcacccga gagggatgt      60 cacggtaaag agcattggaa cgtcggagaa actactccca agaagcaaag agaggtctta    120
ggaagcggac gagatcccca caacgccgga gaatctctgg aagggaaag aggaaggtgg     180 aagaaaaagg ggcgggcctc ccgatccgag gggcccaatc tccagatctg gagagcactc    240
cggcccgaag ggttgagtag cactcagagg gaggaatcca ctcggagatg agcagagaaa    300
tcacctccag aggaccccctt cagcgaacaa gaggcgcttc gagcggtagg agtaagacca    360
tagcgatagg aggagatgct aggagtaggg ggagaccgaa gcgaggagga aagcaaagaa    420
agcaacgggg ctagccggtg ggtgttccgc cccccgagag gggacgagtg aggcttatcc    480
cggggaactc gacttatcgt ccccatctag cgggaccccg gaccccttc gaaagtgacc     540 ggaggggggtg ctgggaacac cggggaccag tggagccatg ggatgccctt cccgatgctc    600
gattccgact cccccccca agggtcgccc aggaatggcg ggacccact ctgcagggtc      660 cgcgttccat ccttcttac ctgatggccg gcatggtccc agcctcctcg ctggcgccgg     720
ctgggcaaca ttccgagggg accgtccct cggtaatggc gaatgggacc cacaaatctc      780
tctagattcc gatagagaat cgagagaaaa gtggctctcc cttagccatc cgagtggacc     840
```

| | | | | |
|---|---|---|---|---|
| tgcgtcctcc | ttcggatgcc | caggtcggac | cgcgaggagg | tggagatgcc atgccgaccc | 900 |
| gaagaggaaa | gaaggacgcg | agacgcaaac | ctgtgagtgg | aaacccgctt tattcactgg | 960 |
| ggtcgacaac | tctggggaga | aaagggcgga | tcggctggga | agagtatatc ctatggaaat | 1020 |
| ccctggtttc | ccctgatgtc | cagccccctcc | ccggtccgag | agaaggggga ctccgggact | 1080 |
| ccctgcagat | tggggacgaa | gccgcccccg | ggcgctcccc | tcgatccacc ttcgaggggg | 1140 |
| ttcacacccc | caaccggcgg | gccggctact | cttctttccc | ttctctcgtc ttcctcggtc | 1200 |
| aacctcctga | gttcctcttc | ttcctccttg | ctgaggttct | tgcctcccgc cgatagctgc | 1260 |
| ttcttcttgt | tctcgagggc | cttccttcgt | cggtgatcct | gcctctcctt gtcggtgaat | 1320 |
| cctcccctga | gaggcctctt | ccgaggtccg | gagtctacct | ccatctggtc cgttcgggcc | 1380 |
| ctcttcgcgg | ggggagcccc | ctctccatcc | ttatccttct | ttccgagaat tcctttgatg | 1440 |
| ttccccagcc | agggattttc | gtcctctatc | ttcttgagtt | tcttctttgt cttccggagg | 1500 |
| tctctctcga | gttcctctaa | cttctttctt | ccggccaccc | actgctcgag gatctcttct | 1560 |
| ctccctccgc | ggttcttcct | cgactcggac | cggctcatct | cggctagagg cggcagtcct | 1620 |
| cagtactctt | acacttttct | gtaaagagga | gactgctgga | ctcgccgccc gagcccgag | 1679 |

<210> SEQ ID NO 2
<211> LENGTH: 195
<212> TYPE: PRT
<213> ORGANISM: Hepatitis D virus

<400> SEQUENCE: 2

Met Ser Arg Ser Glu Ser Arg Lys Asn Arg Gly Gly Arg Glu Glu Ile
1               5                   10                  15

Leu Glu Gln Trp Val Ala Gly Arg Lys Lys Leu Glu Glu Leu Glu Arg
            20                  25                  30

Asp Leu Arg Lys Thr Lys Lys Lys Leu Lys Lys Ile Glu Asp Glu Asn
        35                  40                  45

Pro Trp Leu Gly Asn Ile Lys Gly Ile Leu Gly Lys Lys Asp Lys Asp
    50                  55                  60

Gly Glu Gly Ala Pro Pro Ala Lys Arg Ala Arg Thr Asp Gln Met Glu
65                  70                  75                  80

Val Asp Ser Gly Pro Arg Lys Arg Pro Leu Arg Gly Gly Phe Thr Asp
                85                  90                  95

Lys Glu Arg Gln Asp His Arg Arg Arg Lys Ala Leu Glu Asn Lys Lys
            100                 105                 110

Lys Gln Leu Ser Ala Gly Gly Lys Asn Leu Ser Lys Glu Glu Glu Glu
        115                 120                 125

Glu Leu Arg Arg Leu Thr Glu Glu Asp Glu Arg Arg Glu Arg Arg Val
    130                 135                 140

Ala Gly Pro Pro Val Gly Gly Val Asn Pro Leu Glu Gly Gly Ser Arg
145                 150                 155                 160

Gly Ala Pro Gly Gly Gly Phe Val Pro Asn Leu Gln Val Pro Glu
                165                 170                 175

Ser Pro Phe Ser Arg Thr Gly Glu Gly Leu Asp Ile Arg Gly Asn Gln
            180                 185                 190

Gly Phe Pro
        195

<210> SEQ ID NO 3
<211> LENGTH: 24

```
<212> TYPE: DNA
<213> ORGANISM: Artificial Sequence
<220> FEATURE:
<223> OTHER INFORMATION: Synthetic polynucleotide

<400> SEQUENCE: 3
gagatsccat gccgacccga agag                                              24

<210> SEQ ID NO 4
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 4
gaaggaaggc cctsgagaac aaga                                              24

<210> SEQ ID NO 5
<211> LENGTH: 431
<212> TYPE: DNA
<213> ORGANISM: Hepatitis D virus

<400> SEQUENCE: 5
ggagatgcca tgccgacccg aagaggaaag aaggacgcga gacgcaaacc tgtgagtgga       60
aacccgcttt attcactggg gtcgacaact ctggggagaa aagggcggat cggctgggaa      120
gagtatatcc catggaaatc cctggtttcc cctgatgtcc agcccctccc cggtccgaga      180 gaaggggggac tccgggactc cctgcagatt ggggacgaag ccgccccggg gcgctcccct     240
cgatccacct tcgagggggt tcacaccccc aaccggcggg ccggctactc ttctttccct      300
tctctcgtct tcctcggtca acctcctgag ttcctcttct tcctccttgc tgaggttctt      360
gcctcccgcc gatagctgct tcttcttgtt ctcgagggcc ttccttcgtc ggtgatcctg      420
cctctccttg t                                                           431

<210> SEQ ID NO 6
<211> LENGTH: 431
<212> TYPE: DNA
<213> ORGANISM: Artificial Sequence
<220> FEATURE:
<223> OTHER INFORMATION: Hepatitis delta virus consensus sequence
<220> FEATURE:
<221> NAME/KEY: misc_feature
<222> LOCATION: (62)..(62)
<223> OTHER INFORMATION: n is a, c, g, or t
<220> FEATURE:
<221> NAME/KEY: misc_feature
<222> LOCATION: (356)..(356)
<223> OTHER INFORMATION: n is a, c, g, or t
<220> FEATURE:
<221> NAME/KEY: misc_feature
<222> LOCATION: (359)..(359)
<223> OTHER INFORMATION: n is a, c, g, or t
<220> FEATURE:
<221> NAME/KEY: misc_feature
<222> LOCATION: (423)..(423)
<223> OTHER INFORMATION: n is a, c, g, or t

<400> SEQUENCE: 6
ggagatgcca tgccgacccg aagaggaaag aaggacgcga gacgcaaacc tgtgagtgga       60 anccgcttt attcactggg gtcgacaact ctggggagaa aagggcggat cggctgggaa       120
gagtatatcc catggaaatc cctggtttcc cctgatgtcc agcccctccc cggtccgaga      180 gaaggggggac tccgggactc cctgcagatt ggggacgaag ccgccccggg gcgctcccct     240
```

```
cgatccacct tcgagggggt tcacaccccc aaccggcggg ccggctactc ttctttccct    300
tctctcgtct tcctcggtca acctcctgag ttcctcttct tcctccttgc tgaggntcnt    360
gcctcccgcc gatagctgct tcttcttgtt ctcgagggcc ttccttcgtc ggtgatcctg    420
ccnctccttg t                                                         431
```

```
<210> SEQ ID NO 7
<211> LENGTH: 404
<212> TYPE: DNA
<213> ORGANISM: Hepatitis D virus
<220> FEATURE:
<221> NAME/KEY: misc_feature
<222> LOCATION: (58)..(58)
<223> OTHER INFORMATION: n is a, c, g, or t

<400> SEQUENCE: 7
agatgccacg ccgacccgaa gaggaaagaa ggacgcgaga cgcaaacctg tgagtggnaa     60
cccgctttat tcactggggt cgacaactct ggggagaaaa gggcggatcg gctgggaaga    120
gtatatccta tggaaatccc tggtttcccc tgatgtccag cccctcccg gtccgagaga    180 aggggggactc cggagctccc tgcagattgg ggacgaagcc gccccggggc gctcccctcg    240
atccaccttc gaggggggttc acaccccccaa ccggcgggcc ggctactctt ctttcccttc    300
tctcgtcttc ctcggtcaac ctcctgagtt cctcttcttc ctccttgctg tgkttcttgc    360
ctcccgccga tagctgcttc ttcttgttct cgagggcctt cctt                     404
```

```
<210> SEQ ID NO 8
<211> LENGTH: 405
<212> TYPE: DNA
<213> ORGANISM: Hepatitis D virus
<220> FEATURE:
<221> NAME/KEY: misc_feature
<222> LOCATION: (59)..(59)
<223> OTHER INFORMATION: n is a, c, g, or t
<220> FEATURE:
<221> NAME/KEY: misc_feature
<222> LOCATION: (352)..(352)
<223> OTHER INFORMATION: n is a, c, g, or t

<400> SEQUENCE: 8
gagatgccat gccgacccga agaggaaaga aggacgcgag acgcaaacct gtgagtggna     60 acccgctttta ttcactgggg tcgacaaytc tggggagaaa agggcggatc ggctgggaag    120
agtatatcct atggaaatcc ctggtttccc ctgatgtcca gccctcccc ggkccgagag    180 aagggggact ccgggactcc ctgsagattg gggacgaagc cgccccgggg cgctcccctc    240
gatccacctt cgaggggggtt cacacccccm accggcgggc cggctactct tcyttccctt    300
ctctcgtctt cctcggtcaa cctcctgart tcctcttctt cctccttgct gnagttcttg    360
cctcccgccg atagctgctt cttcttgttc tcgagggcct tcctt                    405
```

```
<210> SEQ ID NO 9
<211> LENGTH: 405
<212> TYPE: DNA
<213> ORGANISM: Hepatitis D virus
<220> FEATURE:
<221> NAME/KEY: misc_feature
<222> LOCATION: (43)..(43)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
```

```
<222> LOCATION: (59)..(59)
<223> OTHER INFORMATION: n is a, c, g, or t
<220> FEATURE:
<221> NAME/KEY: misc_feature
<222> LOCATION: (356)..(356)
<223> OTHER INFORMATION: n is a, c, g, or t
<220> FEATURE:
<221> NAME/KEY: misc_feature
<222> LOCATION: (359)..(359)
<223> OTHER INFORMATION: n is a, c, g, or t
<220> FEATURE:
<221> NAME/KEY: misc_feature
<222> LOCATION: (398)..(398)
<223> OTHER INFORMATION: n is a, c, g, or t

<400> SEQUENCE: 9
gagatgccat gccgacccga agaggaaaga aggacgcgag acncnaacct gtgagtggna      60
acccgcttta ttcactgggg tcgacaactc tggggagaaa agggcggatc ggctgggaag     120
agtatatccc atggaaatcc ctggtttccc ctgatgtcca gccctcccc ggtccgagag      180 aaggggact ccgggactcc ctgcagattg gggacgaagc cgcccccggg cgctcccctc     240
gatccacctt cgagggggtt cacaccccca accggcgggc cggctactct tctttccctt     300
ctctcgtctt cctcggtcaa cctcctgagt tcctcttctt cctccttgct gaggtnctng     360
cctcccgccg atagctgctt cttcttgttc tcgagggnct tcctt                    405

<210> SEQ ID NO 10
<211> LENGTH: 405
<212> TYPE: DNA
<213> ORGANISM: Hepatitis D virus
<220> FEATURE:
<221> NAME/KEY: misc_feature
<222> LOCATION: (59)..(59)
<223> OTHER INFORMATION: n is a, c, g, or t
<220> FEATURE:
<221> NAME/KEY: misc_feature
<222> LOCATION: (355)..(355)
<223> OTHER INFORMATION: n is a, c, g, or t

<400> SEQUENCE: 10
gagatgccat gccgacccga agaggaaaga aggacgcgag acgcaaacct gtgagtggna     60
acccgcttta ttcactgggg tcgacaactc tggggagaaa agggcggatc ggctgggaag    120
agtatatccc atggaaatcc ctggtttccc ctgatgtcca gccctcccc ggtccgagag     180 aaggggact ccgggactcc ctgcagattg gggacgaagc cgcccccggg cgctcccctc    240
gatccacctt cgagggggtt cacaccccca accggcgggc cggctactct tctttccctt    300
ctctcgtctt cctcggtcaa cctcctgagt tcctcttctt cctccttgct gaggntctkg    360
cctcccgccg atagctgctt cttcttgttc tcgagggcct tcctt                   405

<210> SEQ ID NO 11
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 11
ggctactctt ctttcccttc tc                                              22

<210> SEQ ID NO 12
<211> LENGTH: 19
<212> TYPE: DNA
<213> ORGANISM: Artificial Sequence
<220> FEATURE:
```

```
<223> OTHER INFORMATION: Synthetic polynucleotide

<400> SEQUENCE: 12
acaaggagag gcaggatca                                                    19

<210> SEQ ID NO 13
<211> LENGTH: 19
<212> TYPE: DNA
<213> ORGANISM: Artificial Sequence
<220> FEATURE:
<223> OTHER INFORMATION: Synhtetic polynucleotide

<400> SEQUENCE: 13
tctcgtcttc ctcggtcaa                                                    19

<210> SEQ ID NO 14
<211> LENGTH: 20
<212> TYPE: DNA
<213> ORGANISM: Artificial Sequence
<220> FEATURE:
<223> OTHER INFORMATION: Synhtetic polynucleotide

<400> SEQUENCE: 14
gccctcgaga acaagaagaa                                                   20

<210> SEQ ID NO 15
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 15
ttcctccttg ctgaggttct tgcc                                              24

<210> SEQ ID NO 16
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(4)
<223> OTHER INFORMATION: Xaa can be any naturally occurring amino acid

<400> SEQUENCE: 16

Cys Xaa Xaa Xaa
1
```

DETECTION OF HEPATITIS DELTA VIRUS (HDV) FOR THE DIAGNOSIS AND TREATMENT OF SJÖGREN'S SYNDROME AND LYMPHOMA

CROSS REFERENCE TO RELATED APPLICATIONS

This application is the U.S. National Stage of International Application No. PCT/2014/059825, files Oct. 9, 2014, published in English under PCT Article 21(2), which claims the benefit of U.S. Provisional Application No. 62/011,962, filed Jun. 13, 2014, and U.S. Provisional Application No. 61/888,706, filed Oct. 9, 2013. The above-listed applications are herein incorporated by reference in their entirety.

FIELD

This disclosure concerns detection of hepatitis delta virus (HDV) in lymphoma patients and in the salivary glands of patients with Sjögren's syndrome, and the use of HDV for the diagnosis and treatment of lymphoma and Sjögren's syndrome.

BACKGROUND

Hepatitis delta virus (HDV) is an infectious agent dependent upon hepatitis B virus (HBV) for the formation of viral particles. The HDV genome is a small single-stranded RNA of approximately 1700 nucleotides in length that is circular in conformation. The genome RNA is capable of folding using about 74% base pairing to form an unbranched rod-like structure. Replication of the HDV genome occurs through a symmetrical rolling-circle mechanism that involves RNA intermediates, and results in the accumulation of new genomes and complementary RNA species known as antigenomes. In a classic HDV:HBV infection, up to 300,000 copies of genome and 100,000 copies of antigenome accumulate per infected cell during HDV genome replication. It is believed that the genomic and antigenomic RNA circles act as templates for the generation of the multimeric strands of both polarities, which are greater than the 1700-nucleotide unit length. These are processed to unit length RNAs due to the presence of a site-specific ribozyme sequence in both the genome and antigenome. After ribozyme cleavage, the unit-length RNAs are ligated to form new circular RNA species. Since HDV does not encode its own replicase and can replicate autonomously in its host, one or more host RNA polymerases are redirected for its replication (Taylor and Pelchat, *Future Microbiol* 5:393-402, 2010).

A third HDV RNA species approximately 900 nucleotides in length and of antigenomic polarity is also produced at approximately 500 copies per infected cell in the classic HDV:HBV infection. The open reading frame of this RNA encodes a protein that is 195 amino acids in length and is referred to as the small delta antigen (S-HDAg). During replication, an adenosine deaminase that acts on dsRNA converts an adenosine in the termination codon of S-HDAg to an inosine. This amino acid conversion leads to the generation of an mRNA where the termination codon encodes tryptophan, resulting in the production of a second viral protein species that is 19 amino acids longer at the C-terminus, referred to as the large delta antigen (L-HDAg) (Taylor and Pelchat, *Future Microbiol* 5:393-402, 2010).

SUMMARY

Disclosed herein is the identification of HDV nucleic acid and HDV antigen in salivary glands of patients diagnosed with Sjögren's syndrome. Further disclosed is the finding that expression of HDV antigen in healthy mice induces the development of a Sjögren's syndrome-like pathogenesis. Also disclosed herein is the identification of HDV nucleic acid and HDV antigen in lymphoma tumor biopsies. Further disclosed is the finding that expression of HDV antigen in healthy mice induces the development of organized tertiary lymphoid structures in the salivary gland, which is indicative of early stage lymphoma.

Provided herein is a method of diagnosing a subject as having Sjögren's syndrome, or susceptible to developing Sjögren's syndrome, by detecting the presence of HDV nucleic acid or HDV antigen in a sample obtained from the subject; and diagnosing the subject as having Sjögren's syndrome, or susceptible to developing Sjögren's syndrome, if HDV nucleic acid or HDV antigen is detected in the sample. Methods of diagnosing a subject as being susceptible to developing lymphoma are also provided. The methods include detecting the presence of HDV nucleic acid or HDV antigen in a sample obtained from the subject; and diagnosing the subject as being susceptible to developing lymphoma if HDV nucleic acid or HDV antigen is detected in the sample. In some embodiments, the methods further include administering an appropriate therapy to treat the subject. In particular examples, one or any combination of HDV nucleic acid, HDV large antigen (L-HDAg) and HDV small antigen (S-HDAg) are detected in the sample. In some examples, the methods further include detecting the absence of HBV-specific and/or HDV-specific antibodies in a blood or serum sample obtained from the subject. In some embodiments, the methods further include administering an appropriate therapy to treat the subject.

Also provided herein is a method of treating a subject diagnosed with Sjögren's syndrome by selecting a subject who has been diagnosed with Sjögren's syndrome and/or in whom HDV nucleic acid or HDV antigen has been detected; and administering an inhibitor of HDV to the subject. A method of treating lymphoma in a subject, or preventing or inhibiting the development of lymphoma in a subject, is also provided. The method includes selecting a subject diagnosed with lymphoma, a subject susceptible to developing lymphoma and/or a subject in whom HDV nucleic acid or HDV antigen has been detected, and administering an inhibitor of HDV to the subject. In some embodiments, the methods further include detecting HDV nucleic acid or HDV antigen in a sample obtained from the subject. In particular examples, one or any combination of HDV nucleic acid, HDV large antigen (L-HDAg) and HDV small antigen (S-HDAg) are detected in the sample.

Further provided are isolated nucleic acid molecules comprising the nucleotide sequence of an HDV nucleic acid isolated from a patient with Sjögren's syndrome. In some embodiments, the isolated nucleic acid comprises the nucleotide sequence of SEQ ID NO: 6, 7, 8, 9 or 10. In some embodiments, the isolated nucleic acid molecule is a synthetic, labeled and/or chemically modified nucleic acid molecule. Vectors and host cells comprising the nucleic acid molecules are also provided by present disclosure. Isolated viruses comprising the nucleotide sequence of any one of SEQ ID NO: 6, 7, 8, 9 or 10 are also provided by the present disclosure.

Also provided herein are isolated oligonucleotide primers and probes for the detection of HDV nucleic acid in a biological sample and/or the diagnosis of Sjögren's syndrome or lymphoma. In some embodiments, the isolated oligonucleotide is 16 to 40 nucleotides in length and comprises at least 16 contiguous nucleotides of SEQ ID NO: 3, SEQ ID NO: 4, SEQ ID NO: 11, SEQ ID NO: 12, SEQ ID NO: 13, SEQ ID NO: 14 or SEQ ID NO: 15. In some examples, the oligonucleotides are synthetic, labeled and/or chemically modified.

Further provided is a method of detecting HDV nucleic acid in a biological sample by performing an RT-PCR assay to amplify HDV nucleic acid that is present in the biological sample. The RT-PCR assay is performed using a pair of primers specific for HDV; and detecting amplified HDV nucleic acid. In some embodiments, the nucleotide sequences of the primers include the sequences of SEQ ID NO: 3 and SEQ ID NO: 4; SEQ ID NO: 11 and SEQ ID NO: 12; or SEQ ID NO: 13 and SEQ ID NO: 14.

In some embodiments, the method of detecting HDV nucleic acid in a biological sample includes amplifying the HDV nucleic acid using a nested PCR assay. The nested PCR assay comprises a first round of PCR using a first pair of oligonucleotide primers and a second round of PCR using a second pair of oligonucleotide primers; and detecting the amplified HDV nucleic acid using a probe specific for HDV transcript. Kits comprising oligonucleotide primers and/or probes for detection of HDV nucleic acid are further provided.

The foregoing and other objects, features, and advantages of the invention will become more apparent from the following detailed description, which proceeds with reference to the accompanying figures.

BRIEF DESCRIPTION OF THE DRAWINGS

FIG. 1B: Detection of HDV antigen in minor salivary gland biopsy from patients diagnosed with primary Sjögren's syndrome. Immunohistochemical staining of paraffin-embedded minor salivary gland tissue was performed with anti-HDV antigen (HDAg), anti-aquaporin-5 (AQP5) and DAPI nuclear stain.

FIG. 1C: PCR confirmation of HDV sequence identified in RNA isolated from minor salivary glands of patients diagnosed with primary Sjögren's syndrome. The pSS sequence (SEQ ID NO: 6) is a consensus sequence of four individual patients, which is aligned with a portion of an HDV sequence deposited under GenBank™ Accession No. AJ000558 (SEQ ID NO: 5). Variability (N) represents divergence within the patients.

FIG. 1D: Alignment of HDV sequences isolated from four individual Sjögren's syndrome patients (labeled Contig_7, Contig_8, Contig_9 and Contig_10) and the corresponding sequence from an HDV isolate deposited under GenBank™ Accession No. M21012 (nucleotides 883-1287 of SEQ ID NO: 1). Contig_7, Contig_8, Contig_9 and Contig_10 sequences are set forth herein as SEQ ID NO:7, SEQ ID NO: 8, SEQ ID NO: 9 and SEQ ID NO: 10, respectively.

(FIG. 2A) Anti-HDV antibody was measured in serum from healthy controls and pSS patients. No correlation with HDV levels in salivary gland was identified. (FIG. 2B) Anti-HBVc antibody was not detected in pSS patients that were positive for HDV as determined by microarray analysis of RNA isolated from minor salivary gland biopsy.

(FIG. 4A) Pilocarpine stimulated saliva was significantly decreased in mice that were cannulated with S-HDAg (p=0.02, n=5-14). (FIG. 4B) Lymphocytic foci were significantly increased in mice that were cannulated with a combination of rAAV2-S-HDAg/L-HDAG (p<0.005, n=7-11). Foci area was significantly increased in the mice that were cannulated with a combination of rAAV2-S-HDAg/L-HDAG (p<0.005, n=7-11). (FIG. 4C) Foci area was increased in mice that were cannulated with a combination of rAAV2-S-HDAg/L-HDAg (*p<0.05, n=7-36). (FIG. 4D) Anti-nuclear antibodies were significantly increased in in mice that were cannulated with rAAV2-S-HDAg (* p<0.05, n=7-11). (FIG. 4E) Anti-SSA/Ro antibodies were elevated in mice that were cannulated with single HDAg or the combination of S-HDAg/L-HDAg in comparison to control mice transduced with rAAV2-luciferase. (FIG. 4F) Anti-SSB/La was not significantly altered in the presence of HDAg. (FIG. 4G) Total IgG was elevated in the presence of S-HDAg, L-HDAg and S-HDAg/L-HDAg compared to control (*p<0.05, n=7-11). (FIG. 4H) Detection of HDAg in mice cannulated with rAAV2-HDAg.

FIG. 5: Proposed pathway to HDV-mediated development of Sjögren's syndrome. HDV infection initiates with the expression of S-HDAg. In the animal model, S-HDAg significantly induces anti-SSA antibody production, overall upregulation of IgG levels and significant reduction of stimulated saliva production. Autoantibody profiles in patients have been noted to develop about 7 years prior to disease diagnosis. As HDV infection progresses, mutation of the amber stop codon results in increased levels of L-HDAg expressed. The combined expression of S-HDAg and L-HDAg resulted in a significant increase in foci in the mouse model. Lymphocytic infiltrates in humans have been noted to occur later in the pSS disease process.

SEQUENCE LISTING

Figure 1A:
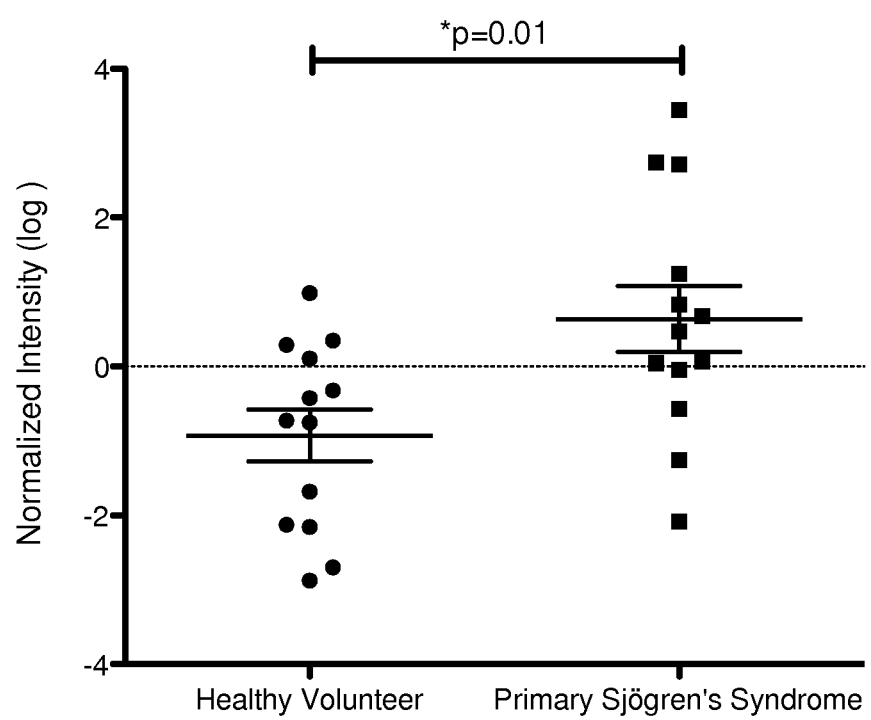
FIG. 1A: Hepatitis delta virus detected in minor salivary glands of primary Sjögren's syndrome patients. Microarray analysis of RNA isolated from minor salivary glands revealed an increase in HDV in primary Sjögren's syndrome patients compared to healthy controls. P-value=0.01, n=13.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Mar. 31, 2016, 10.9 KB, which is incorporated by reference herein. In the accompanying sequence listing:

SEQ ID NO: 1 is the nucleotide sequence of the HDV genome, deposited under GenBank™ Accession No. M21012.

SEQ ID NO: 2 is the amino acid sequence of HDV antigen, deposited under GenBank™ Accession No. M21012.

SEQ ID NOs: 3 and 4 are nucleotide sequences of primers used for detection of HDV.

SEQ ID NO: 5 is the nucleotide sequence of a portion of an HDV genome deposited under GenBank™ Accession No. AJ000558.

SEQ ID NO: 6 is a nucleotide consensus sequence of HDV isolated from four Sjögren's syndrome patient samples.

SEQ ID NOs: 7-10 are HDV nucleotide sequences isolated from four Sjögren's syndrome patient samples.

SEQ ID NOs: 11-15 are nucleotide sequences of primers and a probe for amplification and detection of HDV nucleic acid.

SEQ ID NO: 16 is the amino acid sequence of the CXXX box motif.

DETAILED DESCRIPTION

I. Abbreviations

AAV adeno-associated virus
DAPI 4',6-diamidino-2-phenylindole
ALT alanine aminotransferase
ANA anti-nuclear antibody
AST aspartate aminotransferase
CBV coxsackievirus B
EBV Epstein-Barr virus
FTI farnesyltransferase inhibitor
HBcAb hepatitis B core antibody
HBV hepatitis B virus
HBVc hepatitis B virus core antigen
HCV hepatitis C virus
HDV hepatitis D virus (or hepatitis delta virus)
HIV human immunodeficiency virus
HTLV human T-lymphotropic virus
IFN interferon
L-HDAg large hepatitis delta antigen
MALT mucosa-associated lymphoid tissue
NHL non-Hodgkin's lymphoma
pSS primary Sjögren's syndrome
RT-PCR reverse transcriptase polymerase chain reaction
S-HDAg small hepatitis delta antigen
siRNA small interfering RNA
SS Sjögren's syndrome
TLS tertiary lymphoid structures II. Terms and Methods Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Administration: To provide or give a subject an agent, such as a therapeutic agent, by any effective route. Exemplary routes of administration include, but are not limited to, injection (such as subcutaneous, intramuscular, intradermal, intraperitoneal, and intravenous), oral, intraductal, sublingual, rectal, transdermal, intranasal, vaginal and inhalation routes.

Agent: Any protein, nucleic acid molecule (including chemically modified nucleic acids), compound, small molecule, organic compound, inorganic compound, or other molecule of interest. Agent can include a therapeutic agent, a diagnostic agent or a pharmaceutical agent. A therapeutic or pharmaceutical agent is one that alone or together with an additional compound induces the desired response (such as inducing a therapeutic or prophylactic effect when administered to a subject).

Agent that promotes salivary production: Any compound that increases the amount of saliva produced in a subject (for example, a subject with Sjögren's syndrome). In some cases, an agent that promotes salivary production is a therapeutic agent prescribed by a physician, such as pilocarpine (Salagen™) or cevimeline (Evoxac™).

Antibody: A polypeptide ligand comprising at least a light chain or heavy chain immunoglobulin variable region which recognizes and binds (such as specifically recognizes and specifically binds) an epitope of an antigen, or a fragment thereof. Immunoglobulin molecules are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody.

Antibodies include intact immunoglobulins and the variants and portions of antibodies well known in the art, such as single-domain antibodies (e.g. VH domain antibodies), Fab fragments, Fab' fragments, F(ab)'$_2$ fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term "antibody" also includes genetically engineered forms such as chimeric antibodies (for example, humanized murine antibodies) and heteroconjugate antibodies (such as bispecific antibodies). See also, *Pierce Catalog and Handbook*, 1994-1995 (Pierce Chemical Co., Rockford, Ill.); Kuby, J., *Immunology*, 3$^{rd}$ Ed., W. H. Freeman & Co., New York, 1997.

Typically, a naturally occurring immunoglobulin has heavy (H) chains and light (L) chains interconnected by disulfide bonds. There are two types of light chain, lambda (λ) and kappa (κ). There are five main heavy chain classes (or isotypes) which determine the functional activity of an antibody molecule: IgM, IgD, IgG, IgA and IgE.

Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs." The extent of the framework region and CDRs has been defined according to Kabat et al. (see, Kabat et al., *Sequences of Proteins of Immunological Interest*, U.S. Department of Health and Human Services, 1991) and the ImMunoGeneTics (IMGT) database (available online; Lefranc, *Nucleic Acids Res* 29:207-9, 2001). The Kabat database also is maintained online. The sequences of the framework regions of different light or heavy chains are relatively conserved within a species, such as humans. The framework region of an antibody, that is the combined framework regions of the constituent light and heavy chains, serves to position and align the CDRs in three-dimensional space.

The CDRs are primarily responsible for binding to an epitope of an antigen. The CDRs of each chain are typically referred to as CDR1, CDR2, and CDR3, numbered sequentially starting from the N-terminus, and are often identified by the chain in which the particular CDR is located. Thus, a $V_H$ CDR3 (or H-CDR3) is located in the variable domain of the heavy chain of the antibody in which it is found, whereas a $V_L$ CDR1 (or L-CDR1) is the CDR1 from the variable domain of the light chain of the antibody in which it is found. An antibody that binds a particle antigen will have a specific $V_H$ region and $V_L$ region sequence, and thus specific CDR sequences. Antibodies with different specificities (i.e. different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

References to "$V_H$" or "VH" refer to the variable region of an immunoglobulin heavy chain, including that of an Fv, scFv, dsFv or Fab. References to "$V_L$" or "VL" refer to the variable region of an immunoglobulin light chain, including that of an Fv, scFv, dsFv or Fab.

A "monoclonal antibody" is an antibody produced by a single clone of B-lymphocytes or by a cell into which the light and/or heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

A "chimeric antibody" has framework residues from one species, such as human, and CDRs (which generally confer antigen binding) from another species, such as a murine antibody.

A "human" antibody (also called a "fully human" antibody) is an antibody that includes human framework regions and all of the CDRs from a human immunoglobulin. In one example, the framework and the CDRs are from the same originating human heavy and/or light chain amino acid sequence. However, frameworks from one human antibody can be engineered to include CDRs from a different human antibody. A "humanized" immunoglobulin is an immunoglobulin including a human framework region and one or more CDRs from a non-human (for example a mouse, rat, or synthetic) immunoglobulin. The non-human immunoglobulin providing the CDRs is termed a "donor," and the human immunoglobulin providing the framework is termed an "acceptor." In one embodiment, all the CDRs are from the donor immunoglobulin in a humanized immunoglobulin. Constant regions need not be present, but if they are, they must be substantially identical to human immunoglobulin constant regions, i.e., at least about 85-90%, such as about 95% or more identical. Hence, all parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. Humanized immunoglobulins can be constructed by means of genetic engineering (see for example, U.S. Pat. No. 5,585,089).

Antigen: A compound, composition, or substance that can stimulate the production of antibodies or a T-cell response in an animal, including compositions that are injected or absorbed into an animal. An antigen reacts with the products of specific humoral or cellular immunity, including those induced by heterologous immunogens. In some embodiments of the disclosed compositions and methods, the antigen is the HDV large antigen or HDV small antigen.

Antisense compound: Refers to an oligomeric compound that is at least partially complementary to the region of a target nucleic acid molecule to which it hybridizes. As used herein, an antisense compound that is "specific for" a target nucleic acid molecule is one which specifically hybridizes with and modulates expression of the target nucleic acid molecule. As used herein, a "target" nucleic acid is a nucleic acid molecule to which an antisense compound is designed to specifically hybridize. Non-limiting examples of antisense compounds include primers, probes, antisense oligonucleotides, siRNAs, miRNAs, shRNAs and ribozymes. As such, these compounds can be introduced as single-stranded, double-stranded, circular, branched or hairpin compounds and can contain structural elements such as internal or terminal bulges or loops. Double-stranded antisense compounds can be two strands hybridized to form double-stranded compounds or a single strand with sufficient self-complementarity to allow for hybridization and formation of a fully or partially double-stranded compound.

Antisense oligonucleotide: A single-stranded antisense compound that is a nucleic acid-based oligomer. An antisense oligonucleotide can include one or more chemical modifications to the sugar, base, and/or internucleoside linkages. In some cases, antisense oligonucleotides are "DNA-like" such that when the antisense oligonucleotide hybridizes to a target RNA molecule, the duplex is recognized by RNase H (an enzyme that recognizes DNA:RNA duplexes), resulting in cleavage of the RNA.

Chemical modification (of a nucleic acid): Refers to any non-naturally occurring chemical alteration of a nucleic acid molecule. Exemplary chemical modifications include but are not limited to modified internucleoside linkages, modified sugar moieties and modified bases. Specific chemical modifications that can be made to oligonucleotides are discussed in greater detail in section VI, subsection A.

Control: A "control" refers to a sample or standard used for comparison with an experimental sample, such as a biopsy obtained from a patient with lymphoma. In some embodiments, the control is a sample obtained from a healthy volunteer (also referred to herein as a "normal" control), such as a subject that does not have, or has not been exposed to HDV, does not have HDV localized in the tissues of interest, does not have Sjögren's syndrome and/or does not have lymphoma. In some embodiments, the control is a historical control or standard value (i.e. a previously tested control sample or group of samples that represent baseline or normal values).

Corticosteroids: Steroid hormones that are produced in the adrenal cortex. Corticosteroids are involved in a wide range of physiologic systems such as stress response, immune response and regulation of inflammation, carbohydrate metabolism, protein catabolism, blood electrolyte levels, and behavior. Examples of corticosteroids include cortisol and prednisone.

Detectable label: A detectable compound or composition that is conjugated directly or indirectly to another molecule (such as an oligonucleotide) to facilitate detection of that molecule. Specific, non-limiting examples of labels include, but are not limited to, radioactive isotopes, enzyme substrates, co-factors, ligands, chemiluminescent agents, fluorophores, haptens, enzymes, and combinations thereof. Methods for labeling and guidance in the choice of labels appropriate for various purposes are discussed for example in Sambrook et al. (Molecular Cloning: A Laboratory Manual, Cold Spring Harbor, N.Y., 1989) and Ausubel et al. (In Current Protocols in Molecular Biology, John Wiley & Sons, New York, 1998).

Diagnosis: The process of identifying a disease by its signs, symptoms and/or results of various tests. The conclusion reached through that process is also called "a diagnosis." Forms of testing commonly performed include physical examination, blood tests, medical imaging, genetic analysis, urinalysis, and biopsy.

Farnesyltransferase: An enzyme that adds a 15-carbon isoprenoid (called a farnesyl group) to proteins having a CXXX (SEQ ID NO: 16) box motif at their extreme C-terminal end. The process of adding the farnesyl group is referred to as farnesylation, which is one type of prenylation. The HDV large antigen (L-HDAg) contains a conserved CXXX (SEQ ID NO: 16) motif and farnesylation of this site is required for HDV particle assembly.

Farnesyltransferase inhibitor (FTI): Any agent that inhibits the activity of a farnesyltransferase enzyme. In some examples herein, the FTI is FTI-277, FTI-2153 or BZA-5B.

Focus score: A measure of inflammation often used in the diagnosis of Sjögren's syndrome. Focus score is determined by measuring the number of lymphocytic foci (containing at least 50 inflammatory cells) in a 4 mm$^2$ glandular section.

Healthy control subject: A subject that is not clinically diagnosed with Sjögren's syndrome, lymphoma and/or HDV after an appropriate examination. Healthy control subjects are also referred to herein as "healthy volunteers."

Hepatitis delta virus (HDV): A small, enveloped, spherical virus with a negative sense RNA genome. HDV is considered a subviral satellite because it can only propagate in the presence of hepatitis B virus (HBV). The outer coat of the HDV particle is made up of three HBV envelope proteins (small, medium and large HBV surface antigens). The inner nucleocapsid of HDV is comprised of an approximately 1679 nucleotide single-stranded circular RNA genome and about 200 molecules of HDV antigen. The HDV small antigen (S-HDAg) and HDV large antigen (L-HDAg) have an identical N-terminus, with L-HDAg comprising 19 additional amino acids at its C-terminus. Both antigens are produced from the same reading frame. S-HDAg is produced in the early stages of an infection, enters the nucleus and supports viral replication. In contrast, L-HDAg is expressed in the later stage of HDV infection, acts as an inhibitor of viral replication and is required for assembly of viral particles.

An "HDV nucleic acid" refers to an HDV genomic RNA, an RNA encoded or synthesized by HDV, or any complementary DNA (cDNA) synthesized using an HDV RNA as a template. An "HDV antigen" refers to any protein or fragment thereof encoded by an HDV nucleic acid. In some examples, the HDV antigen is HDV small antigen, or an antigenic fragment thereof. In other examples, the HDV antigen is HDV large antigen, or an antigenic fragment thereof.

Hybridization: To form base pairs between complementary regions of two strands of DNA, RNA, or between DNA and RNA, thereby forming a duplex molecule. Hybridization conditions resulting in particular degrees of stringency will vary depending upon the nature of the hybridization method and the composition and length of the hybridizing nucleic acid sequences. Generally, the temperature of hybridization and the ionic strength (such as the Na concentration) of the hybridization buffer will determine the stringency of hybridization. Calculations regarding hybridization conditions for attaining particular degrees of stringency are discussed in Sambrook et al., (1989) Molecular Cloning, second edition, Cold Spring Harbor Laboratory, Plainview, N.Y. (chapters 9 and 11). The following is an exemplary set of hybridization conditions and is not limiting:

Very High Stringency (Detects Sequences that Share at Least 90% Identity)

Hybridization: 5×SSC at 65° C. for 16 hours

Wash twice: 2×SSC at room temperature (RT) for 15 minutes each

Wash twice: 0.5×SSC at 65° C. for 20 minutes each

High Stringency (Detects Sequences that Share at Least 80% Identity)

Hybridization: 5×-6×SSC at 65° C.-70° C. for 16-20 hours

Wash twice: 2×SSC at RT for 5-20 minutes each

Wash twice: 1×SSC at 55° C.-70° C. for 30 minutes each

Low Stringency (Detects Sequences that Share at Least 60% Identity)

Hybridization: 6×SSC at RT to 55° C. for 16-20 hours

Wash at least twice: 2×-3×SSC at RT to 55° C. for 20-30 minutes each.

Immunoassay: Any biochemical assay that measures the presence of an analyte (such as a protein) in a solution using an antibody. Exemplary immunoassays include, but are not limited to, enzyme-linked immunosorbent assay (ELISA), immunoblot (also referred to as a Western blot), immunoprecipitation, radioimmunoassay, and immunohistochemistry.

Immunosuppressive agent: Includes any drug, agent or compound having the ability to decrease the body's immune system responses. In some embodiments, the immunosuppressive drug is a corticosteroid. In other embodiments, the immunosuppressive drug is a small molecule (such as cyclosporine) or a monoclonal antibody (such as a cytokine blocker).

Inhibitor: Any chemical compound, nucleic acid molecule, small molecule, peptide or polypeptide (including an antibody) that can reduce activity of a gene product, interfere with expression of a gene, or inhibit nucleic acid synthesis, replication and/or assembly of a virus (e.g., HDV). In some examples, an inhibitor can reduce or inhibit the activity of a protein that is encoded by a gene, or inhibit a virus, either directly or indirectly. Direct inhibition can be accomplished, for example, by binding to a protein (such as a viral protein) or a virus particle and thereby preventing the protein or particle from binding an intended target, such as a receptor. Indirect inhibition can be accomplished, for example, by binding to an intended target of the protein or virus, such as a receptor or binding partner, thereby blocking or reducing activity of the protein or virus. In some examples, an inhibitor of the disclosure can inhibit a gene by reducing or inhibiting expression of the gene (such as expression of a viral gene), inter alia by interfering with gene expression (transcription, processing, translation, post-translational modification), for example, by interfering with RNA synthesis and blocking translation of the gene product or by post-translational modification of a gene product, or by causing changes in intracellular localization. In some embodiments of the present disclosure, the inhibitor of HDV is an agent that inhibits expression or activity of an HDV nucleic acid, an HDV protein, or an HDV particle. For example, the HDV inhibitor can be an inhibitor of HDV RNA replication, an HDV-specific antisense compound, an inhibitor of HDV particle assembly, or an antibody specific for an HDV antigen. In some examples, the HDV inhibitor is an agent that eliminates an HDV persistent infection, or blocks the establishment of a persistent HDV infection. In yet other examples, the HDV inhibitor is an agent that changes the localization of HDV (e.g. a change in location that moves HDV away from the salivary gland and/or lymph node).

Isolated: An "isolated" biological component (such as a nucleic acid molecule, protein, or cell) has been substantially separated or purified away from other biological components in the cell or tissue of the organism, or the organism itself, in which the component naturally occurs, such as other chromosomal and extra-chromosomal DNA and RNA, proteins and cells. Nucleic acid molecules and proteins that have been "isolated" include those purified by standard purification methods. The term also embraces nucleic acid molecules and proteins prepared by recombinant expression in a host cell as well as chemically synthesized nucleic acid molecules and proteins.

Lacrimal gland: A gland located in the upper, outer portion of the orbit of the eye. The lacrimal gland secretes tears.

Lymphoma: A type of cancer that begins in cells of the immune system. There are two primary categories of lymphoma—Hodgkin's lymphoma and non-Hodgkin's lymphoma (also referred to as "Hodgkin lymphoma" and "non-Hodgkin lymphoma"). Hodgkin's lymphoma is characterized by the presence of Reed-Sternberg cells. Non-Hodgkin's lymphoma (NHL) encompasses a large, diverse group of cancers of the immune cells. NHL can be further divided into cancers that have an indolent (slow-growing) course and those that have an aggressive (fast-growing) course. These subtypes behave and respond to treatment differently. Both Hodgkin's and non-Hodgkin's lymphomas can occur in children and adults, and prognosis and treatment depend on the stage and the type of cancer. Mucosa-associated lymphoid tissue (MALT) lymphoma is a type of NHL originating in B lymphocytes in the marginal zone of the mucosa-associated lymphoid tissue (MALT).

Non-steroidal anti-inflammatory drug (NSAID): A type of anti-inflammatory agent that works by inhibiting the production of prostaglandins. NSAIDS exert anti-inflammatory, analgesic and antipyretic actions. Examples of NSAIDS include ibuprofen, ketoprofen, piroxicam, naproxen, sulindac, aspirin, choline subsalicylate, diflunisal, fenoprofen, indomethacin, meclofenamate, salsalate, tolmetin and magnesium salicylate.

Oligonucleotide: A polynucleotide sequence of up to about 300 nucleotide bases in length. In some embodiments herein, the oligonucleotide is about 10 to about 50 nucleotides in length. In particular embodiments, the oligonucleotide is about 16 to about 40 nucleotides in length, or about 18 to about 26 nucleotides in length. In specific examples, the oligonucleotide is about 18 to about 26 nucleotides in length, such as 18, 19, 20, 21, 22, 23, 24, 25 or 26 nucleotides in length.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Patient: As used herein, the term "patient" includes human and non-human animals. The preferred patient for treatment is a human. "Patient" and "subject" are used interchangeably herein.

Pharmaceutically acceptable vehicles: The pharmaceutically acceptable carriers (vehicles) useful in this disclosure are conventional. Remington's Pharmaceutical Sciences, by E. W. Martin, Mack Publishing Co., Easton, Pa., 15th Edition (1975), describes compositions and formulations suitable for pharmaceutical delivery of one or more therapeutic compounds, molecules or agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Preventing, treating or ameliorating a disease: "Preventing" a disease (such as Sjögren's syndrome or lymphoma)

refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease.

Primers and probes: Short nucleic acid molecules, for example oligonucleotides 10 nucleotides or more in length. Primers are annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, e.g., by the polymerase chain reaction (PCR) or other nucleic-acid amplification methods known in the art. Probes are used to detect a specific nucleic acid sequence by hybridization. In some embodiments, the primers or probes are at least 10, at least 12, at least 14, at least 16, at least 18, at least 20, at least 22, at least 24, at least 26, at least 28, or at least 30 nucleotides in length. In some examples, the primers or probes are about 16 to about 40 nucleotides in length, or about 18 to about 26 nucleotides in length, such as about 18, 19, 20, 21, 22, 23, 24, 25 or 26 nucleotides in length.

Prognosis: The likelihood of the clinical outcome for a subject afflicted with a specific disease or disorder. With regard to Sjögren's syndrome, the prognosis is a representation of the likelihood (probability) that the disease will progress (worsen) in a subject (develop more severe signs and/or symptoms of the disease). For example, a poor prognosis can indicate an increase in inflammation of the salivary glands, which can lead to mouth dryness, swallowing difficulties, dental decay, gum disease, mouth sores and swelling, infection of the parotid glands and dry lips. In some cases, a poor prognosis indicates swelling of other glands, such as those lining the breathing passages (leading to lung infections) and vagina (causing recurrent vaginal infections). A poor prognosis can also indicate extraglandular symptoms, such as joint pain or inflammation (arthritis), Raynaud's phenomenon, lung inflammation, lymph-node enlargement, kidney, nerve, or muscle disease, or inflammation of the blood vessels (vasculitis).

Promoter: A promoter is an array of nucleic acid control sequences that directs transcription of a nucleic acid. A promoter includes necessary nucleic acid sequences near the start site of transcription, such as in the case of a polymerase II type promoter (a TATA element). A promoter also optionally includes distal enhancer or repressor elements which can be located as much as several thousand base pairs from the start site of transcription. Both constitutive and inducible promoters are included (see e.g., Bitter et al., Methods in Enzymology 153:516-544, 1987).

Promoting or restoring salivary production: The process of increasing salivary production in a subject with diminished salivary flow, such as may result from Sjögren's syndrome. In some embodiments, restoring or promoting salivary production can be accomplished by administering a therapeutic agent. In some examples, the therapeutic agent is a pharmaceutical, such as pilocarpine (Salagen™) or cevimeline (Evoxac™).

Promoting or restoring tear production: The process of increasing tear production in a subject with diminished tearing, such as may result from Sjögren's syndrome. In some embodiments, restoring tear production can be accomplished by administering a therapeutic agent.

Recombinant: A recombinant nucleic acid molecule is one that has a sequence that is not naturally occurring or has a sequence that is made by an artificial combination of two otherwise separated segments of sequence. This artificial combination can be accomplished by chemical synthesis or by the artificial manipulation of isolated segments of nucleic acid molecules, such as by genetic engineering techniques.

Salivary glands: Exocrine glands that produce saliva. As used herein, a "salivary gland" includes any salivary gland in a human subject, including, for example, the parotid glands, minor salivary glands, submandibular glands, sublingual glands and Von Ebner's glands. There are over 600 minor salivary glands located throughout the oral cavity.

Sample or biological sample: A biological specimen containing genomic DNA, RNA, protein, or combinations thereof, obtained from a subject. Examples include, but are not limited to, saliva, peripheral blood, urine, tissue biopsy, surgical specimen, and autopsy material. In one example, a sample includes a biopsy of a salivary gland, such as from a patient with Sjögren's syndrome or a healthy control subject. In other embodiments, the biological sample is a saliva sample. In another example, a sample includes a tumor biopsy, such as from a patient with lymphoma or a healthy control subject. In other embodiments, the biological sample is blood, or a component thereof, such as plasma or serum. In the context of the present disclosure "obtaining a biological sample" includes either directly collecting the sample from the subject, or obtaining the sample from a laboratory or service provider that has collected the sample from the subject. A sample "obtained from a subject" is a sample acquired by similar means.

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods. This homology is more significant when the orthologous proteins or cDNAs are derived from species which are more closely related (such as human and mouse sequences), compared to species more distantly related (such as human and *C. elegans* sequences).

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al., J. Mol. Biol. 215:403-10, 1990) is available from several sources, including the National Center for Biological Information (NCBI) and on the internet, for use in connection with the sequence analysis programs blastp, blastn, blastx, tblastn and tblastx. Additional information can be found at the NCBI web site.

Sialogogue medications: Orally available medications that increase saliva production by stimulating the muscarinic acetylcholine receptors. Currently, pilocarpine (Salagen™) and cevimeline (Evoxac™) are approved for this indication in the United States.

Sjögren's syndrome (SS): An autoimmune disorder characterized by immune cells that attack and destroy the glands that produce tears and saliva. Sjögren's syndrome is not life-threatening or life-shortening, but can significantly reduce quality of life. The hallmark symptoms of the disorder are dry mouth and dry eyes. Sjögren's syndrome may also cause skin, nose and vaginal dryness, and can affect other organs of the body including the kidneys, blood vessels, lungs, liver, pancreas and brain. Sjögren's syndrome affects 1-4 million people in the United States, with women being nine times more likely to develop the disease. The majority of Sjögren's sufferers are at least 40 years old at the time of diagnosis.

A number of different criteria can be used to identify a subject having Sjögren's syndrome and include one or more of: (i) ocular symptoms (for example, persistent dry eyes and/or recurrent sensation of sand or gravel in eyes); (ii) oral symptoms (for example, daily feeling of dry mouth, persistently swollen salivary glands, and/or drinking liquids to swallow dry food); (iii) objective evidence of ocular involvement defined as a positive result of a Schirmer's test performed without anesthesia (≤5 mm in 5 minutes) and/or Rose bengal score or other ocular surface staining score (≥4 according to van Bijsterveld's scoring system; (iv) histopathology in minor salivary glands (measuring focus score or Tarpley score); (v) salivary gland involvement demonstrated with objective evidence of salivary gland involvement by a positive result for unstimulated whole salivary flow (≤1.5 ml in 15 minutes), parotid sialography showing the presence of diffuse sialectasias (punctate, cavitary, or destructive pattern) without evidence of obstruction in the major ducts, and/or salivary scintigraphy showing delayed uptake, reduced concentration and/or delayed excretion of tracer; or (vi) autoantibodies (presence in the serum of antibodies to Ro (SSA) or La (SSB) antigens, or both. Thus, in some embodiments, a subject exhibiting one or more of the above signs or symptoms is selected for treatment according to the methods disclosed herein.

The presence of sicca (dryness) symptoms (sicca symptomology) in the absence of another connective tissue disease is designated "primary Sjögren's syndrome." Primary Sjögren's syndrome can also be characterized in subjects having a positive result for any four of the six criteria listed above, as long as either histopathology (item iv) or serology (item vi) is positive or the presence of any three of the four objective criteria listed above (that is, items iii, iv, v, vi). Patients with an autoimmune process (such as rheumatoid arthritis, systemic lupus erythematosus, progressive systemic sclerosis, scleroderma, or polymyositis), in the presence of item i or item ii listed above, plus any two criteria from items iii, iv, and v, are characterized as having "secondary Sjögren's syndrome."

Small interfering RNA (siRNA): A double-stranded nucleic acid molecule that modulates gene expression through the RNAi pathway (see, for example, Bass, *Nature* 411:428-9, 2001; Elbashir et al., *Nature* 411:494-8, 2001; and PCT Publication Nos. WO 00/44895; WO 01/36646; WO 99/32619; WO 00/01846; WO 01/29058; WO 99/07409; and WO 00/44914). siRNA molecules are generally 20-25 nucleotides in length with 2-nucleotide overhangs on each 3' end. However, siRNAs can also be blunt ended. Generally, one strand of a siRNA molecule is at least partially complementary to a target nucleic acid, such as a target mRNA. siRNAs are also referred to as "small inhibitory RNAs," "small interfering RNAs" or "short inhibitory RNAs." As used herein, siRNA molecules need not be limited to those molecules containing only RNA, but further encompasses chemically modified nucleotides and non-nucleotides having RNAi capacity or activity.

Subject: Living multi-cellular vertebrate organisms, a category that includes human and non-human mammals.

Susceptible to developing lymphoma: In the context of the present disclosure, "susceptible to developing lymphoma" refers to a subject that is at increased risk for developing lymphoma as compared to a control subject (e.g., a subject that has not been exposed to and/or infected with HDV) and/or the general population.

Synthetic: Produced by artificial means in a laboratory, for example a synthetic nucleic acid can be chemically synthesized in a laboratory.

Tarpley score (TS): Characterization of severity of the histopathology of Sjögren's syndrome tissue based on salivary gland biopsies. Symptomatic non-Sjögren's syndrome (dry eyes and/or dry mouth, but no histopathological lesions; also referred to as category "C") has a Tarpley score (TS)=0. Early ("E") Sjögren's syndrome (1-2 lymphocytic aggregates per salivary gland lobule, on average) has a TS=1. Intermediate ("I") Sjögren's syndrome (3 lymphocytic aggregates/lobule, on average) has a TS=2. Severe ("S") Sjögren's syndrome has a TS=3-4 (3=diffuse infiltration though acini associated with partial destruction of acinar tissue; 4=diffuse infiltration associated with complete loss of tissue architecture). Sjögren's syndrome lesions categorized as "less severe" or "focal/negligible disease" has a Tarpley score of 2, whereas Sjögren's syndrome lesions categorized as having "advanced lesions" or "severe/diffuse disease" has a Tarpley score of TS=$2^+$-4.

Therapeutically effective amount: A quantity of a specified pharmaceutical or therapeutic agent sufficient to achieve a desired effect in a subject, or in a cell, being treated with the agent. The effective amount of the agent will be dependent on several factors, including, but not limited to the subject or cells being treated, and the manner of administration of the therapeutic composition.

Therapy: The mode of treatment or care of a patient. In some cases, therapy refers to administration of a therapeutic agent. In some embodiments herein, therapy includes administering an agent that promotes salivary production, administering a corticosteroid, administering an immunosuppressive drug, administering a non-steroidal anti-inflammatory drug, or administering an inhibitor of HDV.

Vector: A vector is a nucleic acid molecule allowing insertion of foreign nucleic acid without disrupting the ability of the vector to replicate and/or integrate in a host cell. A vector can include nucleic acid sequences that permit it to replicate in a host cell, such as an origin of replication. A vector can also include one or more selectable marker genes and other genetic elements. An expression vector is a vector that contains the necessary regulatory sequences to allow transcription and translation of inserted gene or genes. In some embodiments herein, the vector is a plasmid vector. In other embodiments, the vector is a viral vector. In some examples, the viral vector is an AAV vector.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Introduction

Sjögren's syndrome is an autoimmune disease currently diagnosed by (1) a reduction in tear and/or saliva secretion, (2) accumulation of focal lymphocytic infiltrates in salivary gland tissue and (3) detection of auto-antibodies recognizing specific endogenous proteins, including ribonucleoproteins Ro(SSA) and La(SSB) (Vitali et al., *Ann Rheum Dis* 61:554-558, 2002). This disease is estimated to affect 2 million Americans with a prevalence of up to 3% in people over the age of 50 (Drosos et al., *Br J Rheum* 27(2):123-127, 1988).

Multiple gene expression analyses of primary Sjögren's syndrome (pSS) and associated autoimmune diseases have identified a common thread of upregulated pathways suggestive of a viral infection (Yao et al., *Autoimmun Rev* 12:558-566, 2013; Ronnblom and Eloranta, *Curr Opin Rheumatol* 25:248-253, 2013). These include pathways pointing toward pathogen exposure, including upregulation of type I interferon (IFN)-inducible genes and upstream viral-sensing toll-like receptors (Yao et al., *Autoimmun Rev* 12:558-566, 2013; Gottenberg et al., *Proc Natl Acad Sci USA* 103:2770-2775, 2006). Yet, with the collection of evidence supporting a viral-mediated trigger in autoimmune pathogenesis of Sjögren's syndrome, a direct association between viral infection and the development of autoimmune disease had not been established prior to the present disclosure.

Although multiple gene expression analyses have echoed a similar overlying viral-mediated theme, clinical studies have reported unique groups within the pSS patient population presenting with divergent symptomology and disease progression based on age of onset, gender, immunological presentation and extraglandular involvement across a large cohort of Sjögren's syndrome patients (Ramos-Casals et al., *Medicine (Baltimore)* 87:210-219, 2008). The shared stimulation of viral-mediated pathways and the divergent clinical characteristics across the patient population may be due to multiple etiologies, and potentially multiple viruses, behind the collective phenotypic presentation of pSS.

Prior studies have reported evidence of viruses in Sjögren's syndrome patients, most notably coxsackievirus B (CVB), human T lymphotropic virus type 1 (HTLV-1), and Epstein-Barr virus (EBV). Triantafyllopoulou et al. identified a 94 nucleotide fragment of CVB sequence and detected a CVB capsid protein in affected salivary gland tissue of pSS patients in a Greece cohort (Triantafyllopoulou et al., *Arthritis Rheum* 50:2897-2902, 2004), but no further evidence of CVB-mediated Sjögren's syndrome pathogenesis or repeated detection of coxsackievirus has been observed (Gottenberg et al., *Arthritis Rheum* 54:2026-2028, 2006).

A subset of Sjögren's syndrome patients have tested positive for HTLV-1 antibody and have detectable HTLV-1 protein in salivary gland tissue, but a causative or secondary relationship between HTLV-1 and Sjögren's syndrome remains to be established (Lee et al., *J Rheumatol* 39:809-815, 2012). Epstein-Barr virus also has been detected in salivary glands of pSS patients (Saito et al., *J Exp Med* 169:2191-2198, 1989). However, with 95% of the adult population being carriers of EBV, a causative or secondary relationship has been difficult to establish.

All three of these viruses can establish a latent infection and have been shown to reactivate upon conditions of stress (Feuer et al., *J Virol* 76:4430-4440, 2002; Torgeman et al., *Exp Cell Res* 271:169-179, 2001; Stowe et al., *Neuroimmunomodulation* 8:51-58, 2000). It is also noteworthy that confirmed hepatitis C virus (HCV) and human immunodeficiency virus (HIV) infections are exclusion criteria for diagnosis of Sjögren's syndrome. Both HCV and HIV active infections can result in sialadenitis, xerostomia and may result in development of virus-specific autoantibody profiles (Zandman-Goddard and Shoenfeld, *Autoimmun Rev* 1:329-337, 2002; Palazzi et al., *Autoimmun Rev* 11:659-663, 2012). Thus, more than one type of viral infection or concurrent infections may be able to elicit the collective Sjögren's syndrome phenotype.

Patients diagnosed with primary Sjögren's syndrome (pSS) are up to 40 times more likely to develop non-Hodgkin's lymphoma (NHL) than the general population. Sjögren's syndrome patients most frequently develop extranodal marginal zone (MZ) B-cell lymphomas of mucosa-associated lymphoid tissue (MALT) type. These pSS-associated MALT lymphomas are most commonly low-grade/indolent, localized (stage I and II) with extranodal manifestations. Salivary glands are the primary site of lymphoma development in pSS patients. Currently, the cause of NHL in Sjögren's syndrome patients, or NHL in the general population, has yet to be identified. Prior studies have suggested a multifactorial etiology including a combination of genetic susceptibility and environmental exposures, including viral infections.

IV. Overview of Several Embodiments

A. Sjögren's Syndrome

The primary challenge to identifying potential viral triggers of Sjögren's syndrome is differentiating between the background viral signatures of the oral cavity and opportunistic or reactivated viral infections associated with advanced disease from those viruses with the capacity to initiate autoimmune pathogenesis. To address this, a custom viral microarray was designed and utilized to differentiate viral signatures between healthy and Sjögren's syndrome salivary glands. Full length genomes were then recovered from patient samples and their role in eliciting a pSS-like phenotype was tested by functional genomic screening using adeno-associated virus vectors. Using this approach, hepatitis delta virus (HDV) genomes and antigens were identified in minor salivary glands of pSS patients. As disclosed herein, the ability of HDV antigens to trigger the development of a Sjögren's syndrome-like pathogenesis was confirmed in an animal model.

Provided herein are methods of diagnosing a subject as having Sjögren's syndrome, or susceptible to developing Sjögren's syndrome, by detecting the presence of hepatitis delta virus (HDV) nucleic acid or HDV antigen in a sample obtained from the subject; and diagnosing the subject as having Sjögren's syndrome, or susceptible to developing Sjögren's syndrome, if HDV nucleic acid or HDV antigen is detected in the sample.

In some embodiments, the method further includes administering an appropriate therapy to the subject diagnosed as having Sjögren's syndrome. Appropriate therapies can include, for example, administering an agent that promotes salivary production, such as pilocarpine or cevimeline; administering a corticosteroid, such as cortisol or prednisone; administering an immunosuppressive drug, such as a small molecule (e.g. cyclosporine) or a monoclonal antibody (e.g. a cytokine blocker); administering a non-steroidal anti-inflammatory drug, such as ibuprofen, naproxen or aspirin; or administering an inhibitor of HDV, such as an inhibitor of HDV RNA replication (e.g., IFN-α, ribavirin, viramidine), an HDV-specific antisense compound (such as antisense oligonucleotide or an siRNA), an inhibitor of HDV particle assembly (such as an FTI), or an antibody specific for an HDV antigen. Other therapies include administration of an additional agent, such as an interferon (IFN), such as IFN-α or IFN-γ, or a pegylated form thereof.

Methods of detecting HDV nucleic acid or HDV antigen in a sample are well known in the art and an appropriate method can be readily selected by one of skill in the art. In some embodiments, the method comprises detecting HDV nucleic acid by performing a reverse transcriptase polymerase chain reaction (RT-PCR) assay using HDV-specific nucleic acid primers. In some examples, the HDV-specific nucleic acid primers comprise the nucleotide sequence of SEQ ID NO: 3 and SEQ ID NO: 4; SEQ ID NO: 11 and SEQ ID NO: 12; or SEQ ID NO: 13 and SEQ ID NO: 14.

In some embodiments, the method comprises detecting HDV antigen by performing an immunoassay to detect HDV small antigen. In other embodiments, the method comprises detecting HDV antigen by performing an immunoassay to detect HDV large antigen. In particular examples, the immunoassay comprises ELISA, immunoblot (also referred to as a Western blot), immunoprecipitation, radioimmunoassay, or immunohistochemistry.

In particular examples, the method includes detecting HDV nucleic acid by performing an RT-PCR assay using HDV-specific nucleic acid primers, detecting HDV antigen by performing an immunoassay to detect HDV small antigen, or detecting HDV antigen by performing an immunoassay to detect HDV large antigen, or any combination thereof.

In some embodiments, the method further includes detecting the absence of HBV-specific antibodies in a blood or serum sample obtained from the subject, detecting the absence of HDV-specific antibodies in a blood or serum sample obtained from the subject, or both.

In some embodiments, the sample is a tissue sample, such as a salivary gland tissue sample (for example, tissue obtained by biopsy of a salivary gland). In some examples, the salivary gland is a minor salivary gland. In other examples, the salivary gland is a parotid gland, sublingual gland, submandibular gland or Von Ebner's gland. In other embodiments, the tissue sample comprises lacrimal gland tissue. In other embodiments, the biological sample is a bodily fluid sample, such as a saliva, tear, blood or serum sample.

Further provided herein are methods of treating a subject diagnosed with Sjögren's syndrome by selecting a subject diagnosed with Sjögren's syndrome; and administering an inhibitor of HDV to the subject. In some embodiments, the method includes selecting a subject diagnosed with Sjögren's syndrome in whom HDV nucleic acid or HDV antigen has been detected.

In some embodiments, the method further includes (as a first step) detecting the presence of HDV nucleic acid and/or HDV antigen in a sample obtained from the subject.

The HDV inhibitor can be any agent that inhibits expression or activity of an HDV nucleic acid or protein, or an HDV particle. In some embodiments, the HDV inhibitor is an inhibitor of HDV RNA replication. In some examples, the inhibitor of HDV RNA replication is interferon (IFN)-α, ribavirin, viramidine or mycophenolic acid.

In other embodiments, the HDV inhibitor is an antisense compound. In some examples, the antisense compound is an antisense oligonucleotide or a small interfering RNA (siRNA) specific for an HDV nucleic acid.

In other embodiments, the HDV inhibitor is an inhibitor of HDV particle assembly. In some examples, the inhibitor of HDV particle assembly is a farnesyltransferase inhibitor. In specific non-limiting examples, the farnesyltransferase inhibitor is FTI-277, FTI-2153 or BZA-5B.

In yet other embodiments, the HDV inhibitor is an antibody specific for an HDV antigen, such as the HDV small antigen or the HDV large antigen. In particular examples, the antibody specifically recognizes an HDV antigen expressed by an HDV genotype associated with Sjögren's syndrome, such as an antigen expressed by any one of SEQ ID NOs: 6-10.

The present disclosure also provides methods of reducing the development or onset of Sjögren's syndrome in a subject by immunizing the subject against HBV, which in turn inhibits/prevents infection with HDV.

The HDV nucleic acid sequences isolated from minor salivary glands of Sjögren's syndrome patients are most closely related to genotype 1 and genotype 3 HDV, but represent new HDV sequences. Provided herein is an isolated nucleic acid molecule at least 98.5%, at least 90%, at least 90.1%, at least 99.3%, at least 99.5% or at least 99.7% identical to the nucleotide sequence of SEQ ID NO: 6, 7, 8, 9 or 10. For example, the isolated nucleic acid molecule can include 1, 2, 3, 4, 5, 6, 7, or 8 nucleotide substitutions compared with SEQ ID NO: 6, 7, 8, 9 or 10. In some embodiments, the isolated nucleic acid molecule comprises or consists of the nucleotide sequence of SEQ ID NO: 6, 7, 8, 9 or 10. In some embodiments, the isolated nucleic acid molecule is conjugated to a detectable label, such as a fluorophore, an enzyme or a radioisotope. In some embodiments, the isolated nucleic acid molecule is a synthetic nucleic acid molecule. In some embodiments, the isolated nucleic acid molecule is operably linked a promoter. Also provided are vectors, including plasmid vectors and viral vectors, comprising the isolated nucleic acid molecules disclosed herein. Further provided are isolated cells comprising the nucleic acid molecules and vectors.

Isolated viruses comprising a nucleotide sequence at least 98.5%, at least 90%, at least 90.1%, at least 99.3%, at least 99.5% or at least 99.7% identical to the nucleotide sequence of SEQ ID NO: 6, 7, 8, 9 or 10 are also provided by the present disclosure. In some embodiments, the isolated virus comprises the nucleotide sequence of SEQ ID NO: 6, 7, 8, 9 or 10. In some examples, the virus further comprises HDV antigen (such as HDV large antigen, HDV small antigen, or both), and optionally one or more proteins from a helper virus, such as HBV.

Also provided herein are isolated oligonucleotides 16 to 40 nucleotides in length comprising at least 16 contiguous nucleotides of SEQ ID NO: 3, SEQ ID NO: 4. In some embodiments, the oligonucleotides are 18 to 36 nucleotides in length, 20 to 32 nucleotides in length, 22 to 30 nucleotides in length, 22 to 26 nucleotides in length, or 24 to 28 nucleotides in length. In particular examples, the oligonucleotides are 16, 17, 18, 19, 20, 21, 22, 23, 24, 25, 26, 27, 28, 29, 30, 31, 32, 33, 34, 35, 36, 37, 38, 39 or 40 nucleotides in length. In some examples, the isolated oligonucleotides comprise SEQ ID NO: 3 or SEQ ID NO: 4. In some embodiments, the isolated oligonucleotides are conjugated to a detectable label, such as a fluorophore, an enzyme or a radioisotope. In some embodiments, the oligonucleotide comprises at least one chemical modification, such as a modified internucleoside linkage, a modified sugar moiety or a modified base. In some embodiments, the isolated oligonucleotides are synthetic oligonucleotides.

Further provided is a method of detecting HDV nucleic acid in a biological sample performing an RT-PCR assay to amplify HDV nucleic acid that is present in the biological sample, wherein the RT-PCR assay is performed using a pair of primers specific for HDV nucleic acid, and wherein at least one of the primers comprises an oligonucleotide 16 to 40 nucleotides in length comprising at least 16 contiguous nucleotides of SEQ ID NO: 3, SEQ ID NO: 4, SEQ ID NO: 11, SEQ ID NO: 12, SEQ ID NO: 13 or SEQ ID NO: 14; and detecting amplified HDV nucleic acid. In some embodiments, the primers comprise SEQ ID NO: 3 and SEQ ID NO: 4; SEQ ID NO: 11 and SEQ ID NO: 12; or SEQ ID NO: 13 and SEQ ID NO: 14.

B. Lymphoma

The present disclosure also describes the detection of HDV nucleic acid and antigen in patients diagnosed with lymphoma. Expression of HDV antigen in healthy mice resulted in the development of tertiary lymphoid structures that are indicative of the early stages of lymphoma, such as non-Hodgkin's lymphoma. Methods of treating lymphoma in a subject, or preventing or inhibiting the development of lymphoma in a subject, by administering an inhibitor of HDV are provided. Methods for diagnosing a subject as susceptible to developing lymphoma by detecting the presence of HDV nucleic acid or antigen in a sample obtained from the subject are further provided. A sensitive, nested qPCR assay to detect HDV transcript and/or HDV genome in patient samples is also described.

Provided is a method of treating lymphoma in a subject, or preventing or inhibiting the development of lymphoma in a subject. In some embodiments, the method includes selecting a subject diagnosed with lymphoma or a subject susceptible to developing lymphoma; and administering an inhibitor of HDV to the subject. In some embodiments, the method also includes selecting a subject diagnosed with lymphoma or susceptible to developing lymphoma in whom HDV nucleic acid or HDV antigen has been detected.

In some embodiments, the method further includes (as a first step) detecting the presence of HDV nucleic acid and/or HDV antigen in a sample obtained from the subject.

The HDV inhibitor can be any agent that inhibits expression or activity of an HDV nucleic acid or protein, or an HDV particle, or inhibits HDV persistence. In some embodiments, the HDV inhibitor is an inhibitor of HDV RNA replication. In some examples, the inhibitor of HDV RNA replication is interferon (IFN)-α, ribavirin, viramidine or mycophenolic acid. The inhibitor of HDV replication may be non-naturally occurring, for example comprising an RNA analog or a synthetic small molecule drug.

In other embodiments, the HDV inhibitor is an antisense compound. In some examples, the antisense compound is an antisense oligonucleotide or a small interfering RNA (siRNA) specific for an HDV nucleic acid.

In other embodiments, the HDV inhibitor is an inhibitor of HDV particle assembly. In some examples, the inhibitor of HDV particle assembly is a farnesyltransferase inhibitor, such as a non-naturally occurring farnesyltransferase inhibitor. In specific non-limiting examples, the farnesyltransferase inhibitor is FTI-277, FTI-2153 or BZA-5B.

In yet other embodiments, the HDV inhibitor is an antibody specific for an HDV antigen, such as the HDV small antigen or the HDV large antigen. The antibody may be a non-naturally occurring engineered antibody (for example a humanized or framework substituted antibody).

Also provided are methods of diagnosing a subject as being susceptible to developing lymphoma. In some embodiments, the methods include detecting the presence of HDV nucleic acid or HDV antigen in a sample obtained from the subject; and diagnosing the subject as being susceptible to developing lymphoma if HDV nucleic acid or HDV antigen is detected in the sample. In some embodiments, the subject has previously been diagnosed as having Sjögren's syndrome. In other embodiments, the subject has not been previously diagnosed as having Sjögren's syndrome.

In some embodiments, the methods further include administering an appropriate therapy to the subject diagnosed with lymphoma. Appropriate therapies can include, for example, radiation, chemotherapy, stem cell transplant, immunotherapy, surgery, administering an inhibitor of HDV, such as an inhibitor of HDV RNA replication (e.g., IFN-α, ribavirin, viramidine), an HDV-specific antisense compound (such as antisense oligonucleotide or an siRNA), an inhibitor of HDV particle assembly (such as an FTI), or an antibody specific for an HDV antigen, or any combination thereof. Other therapies include administration of an additional agent, such as an interferon (IFN), such as IFN-α or IFN-γ, or a pegylated form thereof. In some examples, immunotherapy comprises administration of an antibody specific for an antigen expressed by lymphoma cells (e.g., CD20, CD52 or CD30), administration of interferon, or administration of an immunomodulatory agent.

Methods of detecting HDV nucleic acid or HDV antigen in a sample are well known in the art and an appropriate method can be readily selected by one of skill in the art. In some embodiments, the methods include detecting HDV nucleic acid in the sample by performing a reverse transcriptase polymerase chain reaction (RT-PCR) assay using HDV-specific nucleic acid primers. In some examples, the RT-PCR assay comprises a nested PCR assay comprising a first round of PCR using a first pair of oligonucleotide primers and a second round of PCR using a second pair of oligonucleotide primers. In some examples, the nested PCR assay amplifies HDV transcript if HDV is present in the sample. In particular examples, at least one of the HDV-specific nucleic acid primers comprises the nucleotide sequence of SEQ ID NO: 3, SEQ ID NO: 4, SEQ ID NO: 11, SEQ ID NO: 12, SEQ ID NO: 13 or SEQ ID NO: 14.

In non-limiting examples, the first pair of oligonucleotide primers comprises the sequences of SEQ ID NO: 11 and SEQ ID NO: 12; and/or the second pair of oligonucleotide primers comprises the sequences of SEQ ID NO: 13 and SEQ ID NO: 14.

In some embodiments, the HDV transcript is detected using a probe comprising SEQ ID NO: 15.

In other embodiments, the method comprises detecting HDV antigen by performing an immunoassay to detect HDV small antigen. In yet other embodiments, the method comprises detecting HDV antigen by performing an immunoassay to detect HDV large antigen. In particular examples, the immunoassay comprises ELISA, immunoblot (also referred to as a Western blot), immunoprecipitation, radioimmunoassay, or immunohistochemistry.

In particular examples, the method includes detecting HDV nucleic acid by performing an RT-PCR assay using HDV-specific nucleic acid primers, detecting HDV antigen by performing an immunoassay to detect HDV small antigen, or detecting HDV antigen by performing an immunoassay to detect HDV large antigen, or any combination thereof.

In some embodiments, the method further includes detecting the absence of HBV-specific antibodies in a blood or serum sample obtained from the subject, detecting the absence of HDV-specific antibodies in a blood or serum sample obtained from the subject, or both.

In some embodiments, the sample is a tissue sample, such as a salivary gland tissue sample (for example, tissue obtained by biopsy of a salivary gland) or a lymphoma tumor biopsy (such as a lymph node biopsy). In some examples, the salivary gland is a minor salivary gland. In other examples, the salivary gland is a parotid gland, sublingual gland, submandibular gland or Von Ebner's gland. In other embodiments, the biological sample is a bodily fluid sample, such as a saliva, tear, blood or serum sample.

In some embodiments of the methods disclosed herein, the lymphoma is non-Hodgkin's lymphoma (NHL). In some examples, the NHL is mucosa-associated lymphoid tissue (MALT) lymphoma.

Also provided herein are methods for the detection of HDV nucleic acid in a sample. In some embodiments, the methods include amplifying the HDV nucleic acid using a nested PCR assay, wherein the nested PCR assay comprises a first round of PCR using a first pair of oligonucleotide primers and a second round of PCR using a second pair of oligonucleotide primers; and detecting the amplified HDV nucleic acid using a probe specific for HDV transcript. In some examples, the nested PCR assay is preceded by reverse transcription of HDV RNA present in the sample. In particular examples, reverse transcription of HDV RNA is mediated by a reverse transcriptase enzyme and random hexamer primers. In specific examples, the first pair of oligonucleotide primers comprises the sequences of SEQ ID NO: 11 and SEQ ID NO: 12; and/or the second pair of oligonucleotide primers comprises the sequences of SEQ ID NO: 13 and SEQ ID NO: 14. In some examples, the HDV transcript is detected using a probe comprising SEQ ID NO: 15. In non-limiting examples, the probe comprises a detectable label and/or at least one of the primers comprises a detectable label.

Further provided herein are isolated oligonucleotides 16 to 40 nucleotides in length comprising at least 16 contiguous nucleotides of SEQ ID NO: 11, SEQ ID NO: 12, SEQ ID NO: 13, SEQ ID NO: 14 or SEQ ID NO: 15. In some embodiments, the oligonucleotides are 18 to 36 nucleotides in length, 20 to 32 nucleotides in length, 22 to 30 nucleotides in length, 22 to 26 nucleotides in length, 16 to 26 nucleotides in length, or 24 to 28 nucleotides in length. In particular examples, the oligonucleotides are 16, 17, 18, 19, 20, 21, 22, 23, 24, 25, 26, 27, 28, 29, 30, 31, 32, 33, 34, 35, 36, 37, 38, 39 or 40 nucleotides in length. In some examples, the isolated oligonucleotides comprise SEQ ID NO: 11, SEQ ID NO: 12, SEQ ID NO: 13, SEQ ID NO: 14 or SEQ ID NO: 15.

Also provided are oligonucleotides 16 to 40 nucleotides in length comprising a nucleotide sequence at least 80%, at least 85%, at least 90%, at least 95%, at least 96%, at least 97%, at least 98% or at least 99% identical to SEQ ID NO: 11, SEQ ID NO: 12, SEQ ID NO: 13, SEQ ID NO: 14 or SEQ ID NO: 15.

In some embodiments, the isolated oligonucleotides are conjugated to a detectable label, such as a fluorophore, an enzyme or a radioisotope. In some embodiments, the oligonucleotide comprises at least one chemical modification, such as a modified internucleoside linkage, a modified sugar moiety or a modified base. In some embodiments, the isolated oligonucleotides are synthetic oligonucleotides.

Also provided are kits for detecting HDV nucleic acid. In some embodiments, the kits comprise at least one HDV-specific oligonucleotide primer or probe disclosed herein. In some examples, the kit comprises at least one oligonucleotide selected from an oligonucleotide comprising SEQ ID NO: 11, an oligonucleotide comprising SEQ ID NO: 12, an oligonucleotide comprising SEQ ID NO: 13, an oligonucleotide comprising SEQ ID NO: 14 and an oligonucleotide comprising SEQ ID NO: 15. The kits optionally further include a Taq DNA polymerase, deoxynucleotides (dNTPs) and/or buffer.

In particular examples, the kits comprise at least one pair of oligonucleotide primers, wherein the primers comprise the sequences of SEQ ID NO: 11 and SEQ ID NO: 12; and/or SEQ ID NO: 13 and SEQ ID NO: 14. In some examples, the kits further include an oligonucleotide probe comprising the sequence of SEQ ID NO: 15.

In some examples, at least one oligonucleotide in the kit comprises a detectable label, such as such as a fluorophore, an enzyme or a radioisotope, or comprises at least one chemical modification, such as a modified internucleoside linkage, a modified sugar moiety or a modified base. In some cases, the oligonucleotides are synthetic oligonucleotides.

V. Methods for Diagnosing Sjögren's Syndrome or Lymphoma

Provided herein are methods of diagnosing a subject as having Sjögren's syndrome, or susceptible to developing Sjögren's syndrome, by detecting the presence of HDV nucleic acid or HDV antigen in a sample obtained from the subject; and diagnosing the subject as having Sjögren's syndrome, or susceptible to developing Sjögren's syndrome, if HDV nucleic acid or HDV antigen is detected in the sample.

Further provided herein are methods of diagnosing a subject as being susceptible to lymphoma by detecting the presence of HDV nucleic acid or HDV antigen in a sample obtained from the subject; and diagnosing the subject as being susceptible to lymphoma if HDV nucleic acid or HDV antigen is detected in the sample.

Methods of detecting viral DNA or viral proteins are well known in the art and an appropriate method can be readily selected. One of skill in the art understands that detecting the presence of a specific nucleic acid or protein (such as an HDV nucleic acid or protein) in a sample generally includes comparing the sample to a negative control sample or reference value. For example, the negative control sample can be a nucleic acid or tissue sample known to be free of HDV nucleic acid or protein, such as from a subject that has not been exposed to HDV.

A. Methods for Detection of HDV Nucleic Acid

In some embodiments, RNA is isolated from a sample of a subject, such as a fluid sample or tissue sample (such as salivary gland biopsy or a lymphoma tumor biopsy). General methods for RNA extraction are well known in the art and are disclosed in standard textbooks of molecular biology, including Ausubel et al., Current Protocols of Molecular Biology, John Wiley and Sons (1997). Methods for RNA extraction from paraffin embedded tissues are disclosed, for example, in Rupp and Locker, Lab Invest. 56:A67 (1987), and De Andres et al., *BioTechniques* 18:42044 (1995). In one example, RNA isolation can be performed using a purification kit, buffer set and protease from commercial manufacturers. Total RNA from tissue samples can be isolated, for example, using RNeasy Mini Kit (Qiagen) or RNA Stat-60 (Tel-Test). RNA prepared from salivary gland or other biological sample can be isolated, for example, by cesium chloride density gradient centrifugation.

Methods of detecting specific nucleic acid sequences include methods based on hybridization of polynucleotides, methods based on sequencing of polynucleotides, and proteomics-based methods. In some examples, nucleic acid in a sample is detected and/or quantified using northern blotting or in situ hybridization (Parker & Barnes, Methods in Molecular Biology 106:247-283, 1999); RNAse protection assays (Hod, *Biotechniques* 13:852-4, 1992); or PCR-based methods, such as reverse transcription polymerase chain reaction (RT-PCR) (Weis et al., Trends in Genetics 8:263-4, 1992). In some examples, a viral microarray or RT-PCR can be used to detect the presence of HDV nucleic acid in different samples, such as in salivary gland tissue or lymphoma tumor biopsy samples.

Methods for detecting and/or quantitating RNA are well known in the art. In one example, the method utilizes RT-PCR. Generally, the first step in nucleic acid detection by RT-PCR is the reverse transcription of the RNA template into cDNA, followed by its exponential amplification in a PCR reaction. The reverse transcription step is typically primed using specific primers, random hexamers, or oligo-dT primers, depending on the circumstances and the goal of the assay. In some embodiments herein, the method of detecting HDV nucleic acid utilizes RT-PCR and primers comprising the nucleotide sequences of SEQ ID NO: 3 and SEQ ID NO: 4. In other embodiments herein, the method of detecting HDV nucleic acid utilizes a reverse transcription step (using random hexamer primers) followed by a nested PCR assay. The nested PCR assay includes two rounds of PCR that lead to amplification of HDV transcript and/or HDV genome. In particular examples, the primers used for the nested PCR assay comprise SEQ ID NOs: 11-14. In non-limiting examples, the HDV transcript can be detected using a probe comprising SEQ ID NO: 15.

To minimize errors and the effect of sample-to-sample variation, RT-PCR can be performed using an internal standard. The ideal internal standard is expressed at a constant level among different tissues, and is unaffected by the experimental treatment. RNAs commonly used to normalize patterns of gene expression are mRNAs for the housekeeping genes glyceraldehyde-3-phosphate-dehydrogenase (GAPDH), beta-actin, and 18S ribosomal RNA.

A variation of RT-PCR is real time quantitative RT-PCR, which measures PCR product accumulation through a dual-labeled fluorogenic probe (e.g. TAQMAN® probe). Real time PCR is compatible both with quantitative competitive PCR, where internal competitor for each target sequence is used for normalization, and with quantitative comparative PCR using a normalization gene contained within the sample, or a housekeeping gene for RT-PCR (see Held et al., *Genome Research* 6:986 994, 1996). Quantitative PCR is also described in U.S. Pat. No. 5,538,848. Related probes and quantitative amplification procedures are described in U.S. Pat. Nos. 5,716,784 and 5,723,591.

The steps of a representative protocol for detecting/quantitating gene expression using fixed, paraffin-embedded tissues as the RNA source, including RNA isolation, purification, primer extension and amplification are given in various published journal articles (see Godfrey et al., *J. Mol. Diag.* 2:84-91, 2000; Specht et al., *Am. J. Pathol.* 158:419-429, 2001).

In some examples, the presence of nucleic acid in a sample is identified or confirmed using the microarray technique. Thus, the expression profile can be measured in either fresh or paraffin-embedded tissue or cells, using microarray technology, such as by using a viral microarray (see Example 1).

In situ hybridization (ISH) is another method for detecting nucleic acid molecules of interest. ISH applies and extrapolates the technology of nucleic acid hybridization to the single cell level, and, in combination with the art of cytochemistry, immunocytochemistry and immunohistochemistry, permits the maintenance of morphology and the identification of cellular markers to be maintained and identified, and allows the localization of sequences to specific cells within populations, such as tissues and blood samples. ISH is a type of hybridization that uses a complementary nucleic acid to localize one or more specific nucleic acid sequences in a portion or section of tissue (in situ), or, if the tissue is small enough, in the entire tissue (whole mount ISH).

Sample cells or tissues are treated to increase their permeability to allow a probe to enter the cells. The probe is added to the treated cells, allowed to hybridize at pertinent temperature, and excess probe is washed away. A complementary probe is labeled with a radioactive, fluorescent or antigenic tag, so that the probe's location and quantity in the tissue can be determined using autoradiography, fluorescence microscopy or immunoassay. The sample may be any sample as herein described, such as a salivary gland biopsy. Probes can be designed to specifically bind the nucleic acid of interest, such as an HDV nucleic acid set forth herein as any one of SEQ ID NOs: 6-10.

B. Methods for Detection of HDV Antigen

In some examples, samples obtained from a subject, such as a blood sample or a tissue sample (such as a salivary gland sample or a tumor biopsy), are evaluated for the presence of HDV antigen, such as HDV large and/or small antigen.

Antibodies specific HDV protein can be used for detection and quantitation by one of a number of immunoassay methods that are well known in the art, such as those presented in Harlow and Lane (*Antibodies, A Laboratory Manual*, CSHL, New York, 1988). Methods of constructing such antibodies are known in the art. Alternatively, HDV-specific antibodies can be obtained from commercially or publically available sources.

Any standard immunoassay format (such as ELISA, Western blot, or radioimmunoassay) can be used to detect and/or measure protein levels. Thus, HDV protein in a sample can readily be evaluated using these methods. Immunohistochemical techniques can also be utilized for detection of HDV protein. General guidance regarding such techniques can be found in Bancroft and Stevens (*Theory and Practice of Histological Techniques*, Churchill Livingstone, 1982) and Ausubel et al. (*Current Protocols in Molecular Biology*, John Wiley & Sons, New York, 1998). In one examples, HDV antigen is detected using confocal immunofluorescent antigen detection with an HDV specific affinity purified antibody against amino acids 96-111 of delta antigen (accession M21012, Yenzyme, Calif.) (see Example 1).

C. Other Methods for Sjögren's Syndrome Diagnosis

In some embodiments of the diagnostic methods disclosed herein, if the diagnostic test indicates the subject has Sjögren's syndrome, or is susceptible to developing Sjögren's syndrome, the subject is subjected to additional diagnostic tests to confirm the diagnosis by other means. Alternatively, the test is used to confirm a diagnosis already indicated by other means.

Any one of a number of means known in the art of diagnosing a subject with Sjögren's syndrome can be used. Other means of diagnosing Sjögren's syndrome, or confirming a diagnosis of Sjögren's syndrome, can include one or more of: (i) ocular symptoms (for example, persistent dry eyes and/or recurrent sensation of sand or gravel in eyes); (ii) oral symptoms (for example, daily feeling of dry mouth, persistently swollen salivary glands, and/or drinking liquids to swallow dry food); (iii) objective evidence of ocular involvement defined as a positive result of a Schirmer's test performed without anesthesia (≤5 mm in 5 minutes) and/or Rose bengal score or other ocular surface staining score (≥4 according to van Bijsterveld's scoring system; (iv) histopathology in minor salivary glands (measuring focus score or Tarpley score); (v) salivary gland involvement demonstrated with objective evidence of salivary gland involvement by a positive result for unstimulated whole salivary flow (≤1.5 ml in 15 minutes), parotid sialography showing the presence of diffuse sialectasias (punctate, cavitary, or destructive pattern) without evidence of obstruction in the major ducts, and/or salivary scintigraphy showing delayed uptake, reduced concentration and/or delayed excretion of tracer; and/or (vi) autoantibodies (presence in the serum of antibodies to Ro (SSA) or La (SSB) antigens, or both.

VI. Methods for the Treatment of Sjögren's Syndrome or Lymphoma

Provided herein are methods of treating a subject diagnosed with Sjögren's syndrome by selecting a subject diagnosed with Sjögren's syndrome; and administering an inhibitor of HDV to the subject. In some embodiments, the method includes selecting a subject diagnosed with Sjögren's syndrome in whom HDV nucleic acid or HDV antigen has been detected.

Also provided herein are methods of treating lymphoma in a subject, or preventing or inhibiting the development of lymphoma in a subject, by selecting a subject diagnosed with lymphoma or susceptible to developing lymphoma; and administering an inhibitor of HDV to the subject. In some embodiments, the method includes selecting a subject diagnosed with lymphoma or susceptible to developing lymphoma in whom HDV nucleic acid or HDV antigen has been detected.

The HDV inhibitor can be any agent that inhibits expression or activity of an HDV nucleic acid or protein, or an HDV particle. For example, the HDV inhibitor can be an inhibitor of HDV RNA replication, an HDV-specific antisense compound, an inhibitor of HDV particle assembly, or an antibody specific for an HDV antigen. The HDV inhibitor may also be an agent that eliminates the persistent infection of HDV, which occurs in the absence of HBV infection. In yet other examples, the HDV inhibitor is an agent that blocks the establishment of a persistent HDV infection, or an agent that changes the localization of HDV (e.g. a change in location that moves HDV away from the salivary gland and/or lymph node).

In some embodiments disclosed herein, the HDV inhibitor is an inhibitor of HDV RNA replication. A number of inhibitors of viral replication are known in the art. In some examples, the inhibitor of HDV RNA replication is interferon (IFN)-α, ribavirin, viramidine or mycophenolic acid.

In other embodiments, the HDV inhibitor is an antisense compound. In some examples, the antisense compound is an antisense oligonucleotide or a small interfering RNA (siRNA) specific for an HDV nucleic acid. Chemical modifications of antisense compounds are discussed below.

In other embodiments, the HDV inhibitor is an inhibitor of HDV particle assembly. In some examples, the inhibitor of HDV particle assembly is a farnesyltransferase inhibitor, such as FTI-277, FTI-2153 or BZA-5B.

In yet other embodiments, the HDV inhibitor is an antibody specific for an HDV antigen, such as the HDV small antigen or the HDV large antigen. In particular examples, the antibody specifically recognizes an HDV antigen expressed by an HDV genotype associated with Sjögren's syndrome, such as an antigen expressed by any one of SEQ ID NOs: 6-10.

A. Antisense Compounds Specific for HDV

Antisense compounds, such as antisense oligonucleotides or si SiRNA molecules, specific for an HDV nucleic acid can be readily designed using publically available HDV nucleic acid sequences GenBank™ Accession No. M21012, set forth herein as SEQ ID NO: 1), or any of the HDV nucleic acid sequences set forth herein (SEQ ID NOs: 5-10).

Antisense compounds need not be 100% complementary to the target nucleic acid molecule to specifically hybridize with the target nucleic acid molecule. For example, the antisense compound, or antisense strand of the compound if a double-stranded compound, can be at least 75%, at least 80%, at least 85%, at least 90%, at least 95%, at least 99% or 100% complementary to the selected target nucleic acid sequence. Methods of screening antisense compounds for specificity are well known in the art (see, for example, U.S. Patent Application Publication No. 2003-0228689).

Generally, the principle behind antisense technology is that an antisense compound hybridizes to a target nucleic acid and effects the modulation of gene expression activity or function. The modulation of gene expression can be achieved by, for example, target RNA degradation or occupancy-based inhibition. An example of modulation of target RNA function by degradation is RNase H-based degradation of the target RNA upon hybridization with a DNA-like antisense compound, such as an antisense oligonucleotide.

Another example of modulation of gene expression by target degradation is RNA interference (RNAi) using small interfering RNAs (siRNAs). RNAi is a form of antisense-mediated gene silencing involving the introduction of double stranded (ds)RNA-like oligonucleotides leading to the sequence-specific reduction of targeted endogenous RNA levels.

Each of the above-described antisense compounds provides sequence-specific target gene regulation. This sequence-specificity makes antisense compounds effective tools for the selective modulation of a target nucleic acid of interest, such as an HDV nucleic acid.

In some embodiments, the antisense compounds are antisense oligonucleotides. The antisense oligonucleotides can be any suitable length to allow for hybridization and degradation of an RNA. The length of an antisense oligonucleotide can vary, but is typically about 15 to about 40 nucleotides, including 15, 16, 17, 18, 19, 20, 21, 22, 23, 24, 25, 26, 27, 28, 29, 30, 31, 32, 33, 34, 35, 36, 37, 38, 39 or 40 nucleotides. In some embodiments, the antisense oligonucleotides are about 20 to about 35 nucleotides in length. The antisense oligonucleotides can be DNA, RNA or analogs thereof. Furthermore, the oligonucleotides provided herein can be unmodified or can comprise one or more modifications, such as modified internucleoside linkages, modified sugar moieties, modified bases, or a combination thereof. Oligonucleotide modifications are described in detail below.

In other embodiments, the antisense compounds are siRNA molecules. siRNAs useful for the disclosed methods include short double-stranded RNA from about 17 nucleotides to about 29 nucleotides in length, preferably from about 19 to about 25 nucleotides in length, such as about 21 to about 23 nucleotides in length. The siRNAs are made up of a sense RNA strand and a complementary antisense RNA strand annealed together by standard Watson-Crick base-pairing interactions. The sense strand includes a nucleic acid sequence that is substantially identical to a nucleic acid sequence contained within the target nucleic acid. As used herein, an siRNA nucleic acid sequence that is "substantially identical" to a target sequence is a nucleic acid sequence that is identical to the target sequence, or that differs from the target sequence by one, two or three nucleotides. The sense and antisense strands of the siRNA can either include two complementary, single-stranded RNA molecules, or can be a single molecule having two complementary portions (which are base-paired) separated a single-stranded "hairpin" region.

The siRNA can also be altered RNA that differs from naturally-occurring RNA by the addition, deletion, substitution and/or alteration of one or more nucleotides. Such alterations can include addition of non-nucleotide material, such as to one or both of the ends of the siRNA or to one or more internal nucleotides of the siRNA; modifications that make the siRNA resistant to nuclease digestion; or the substitution of one or more nucleotides in the siRNA with deoxyribonucleotides. One or both strands of the siRNA can also include a 3' overhang. As used herein, a "3' overhang" refers to at least one unpaired nucleotide extending from the 3'-end of a duplexed RNA strand. Thus, in certain embodiments, the siRNA includes at least one 3' overhang of from 1 to about 6 nucleotides (which includes ribonucleotides or deoxyribonucleotides) in length, from 1 to about 5 nucleotides in length, from 1 to about 4 nucleotides in length, or from about 2 to about 4 nucleotides in length. In a particular embodiment, the 3' overhang is present on both strands of the siRNA and is 2 nucleotides in length. For example, each strand of the siRNA can comprise 3' overhangs of dithymidylic acid ("TT") or diuridylic acid ("uu").

Antisense compounds, such as antisense oligonucleotides and siRNAs, can be produced chemically or biologically, or can be expressed from a recombinant plasmid or viral vector. Exemplary methods for producing and testing antisense compounds are well known in the art (see, for example, U.S. Pat. Nos. 5,849,902 and 4,987,071; U.S. Patent Application Publication Nos. 2002/0173478 and 2004/0018176; Stein and Cheng, *Science* 261:1004, 1993; Werner and Uhlenbeck, *Nucl. Acids Res.* 23:2092-2096, 1995; Hammann et al., *Antisense and Nucleic Acid Drug Dev.* 9:25-31).

In some examples, the antisense compounds contain one or more modifications to enhance nuclease resistance and/or increase activity of the compound. Modified antisense compounds include those comprising modified backbones or non-natural internucleoside linkages. As defined herein, oligonucleotides having modified backbones include those that retain a phosphorus atom in the backbone and those that do not have a phosphorus atom in the backbone.

Examples of modified oligonucleotide backbones include, but are not limited to, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkyl-phosphonates, thionoalkyl-phosphotriesters, and boranophosphates having normal 3'-5' linkages, 2'-5' linked analogs of these, and those having inverted polarity wherein the adjacent pairs of the nucleoside units are linked 3'-5' to 5'-3' or 2'-5' to 5'-2'. Representative U.S. patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

Examples of modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439.

In some embodiments, both the sugar and the internucleoside linkage of the nucleotide units of the oligonucleotide or antisense compound are replaced with novel groups. One such modified compound is an oligonucleotide mimetic referred to as a peptide nucleic acid (PNA). In PNA compounds, the sugar-backbone of an oligonucleotide is replaced with an amide containing backbone, in particular an aminoethylglycine backbone. The bases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262. Further teaching of PNA compounds can be found in Nielsen et al. (*Science* 254, 1497-1500, 1991).

Modified oligonucleotides can also contain one or more substituted sugar moieties. In some examples, the oligonucleotides can comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. In other embodiments, the antisense compounds comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. In one example, the modification includes 2'-methoxyethoxy (also known as 2'-O-(2-methoxyethyl) or 2'-MOE) (Martin et al., *Helv. Chim. Acta.*, 78, 486-504, 1995). In other examples, the modification includes 2'-dimethylaminooxyethoxy (also known as 2'-DMAOE) or 2'-dimethylaminoethoxyethoxy (also known in the art as 2'-O-dimethylaminoethoxyethyl or 2'-DMAEOE).

Similar modifications can also be made at other positions of the compound. Antisense compounds can also have sugar mimetics such as cyclobutyl moieties in place of the pentofuranosyl sugar. Representative United States patents that teach the preparation of modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920.

Oligonucleotides can also include base modifications or substitutions. As used herein, "unmodified" or "natural" bases include the purine bases adenine (A) and guanine (G), and the pyrimidine bases thymine (T), cytosine (C) and uracil (U). Modified bases include other synthetic and natural bases, such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further modified bases have been described (see, for example, U.S. Pat. No. 3,687,808; and Sanghvi, Y. S., Chapter 15, Antisense Research and Applications, pages 289-302, Crooke, S. T. and Lebleu, B., ed., CRC Press, 1993).

Certain of these modified bases are useful for increasing the binding affinity of antisense compounds. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. Representative U.S. patents that teach the preparation of modified bases include, but are not limited to, U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,681,941; and 5,750,692.

B. Farnesyltransferase Inhibitors (FTIs) as HDV Inhibitors

Farnesylation refers to the process of adding a farnesyl group (a 15-carbon prenyl lipid) to conserved cysteine residues at or near the C-terminus of a protein. Farnesyltransferases, the enzymes that mediate this process, recognize a particular substrate, referred to as a CXXX box motif (SEQ ID NO: 6), at the C-terminal end of proteins. The HDV large antigen (L-HDAg) contains a conserved CXXX motif and farnesylation of this site has been shown to be required for HDV particle assembly (Glenn et al., *Science* 256:1331-1333, 1992; Hwang et al., *Virology* 190:413-422, 1992; Einav and Glenn, *J Antimicrob Chemother* 52(6):883-886, 2003).

Thus. in some embodiments herein, the inhibitor of HDV is a farnesyltransferase inhibitor (FTI). A number of FM are known in the art, some of which have been shown to inhibit HDV particle assembly in vitro and/or in vivo (Glenn et al., *J Virol* 72:9303-9306, 1998; Bordier et al., *J Virol* 76:10465-10472, 2002; Bordier et al., *J Clin Invest* 112:407-414, 2003). Any suitable FTI can be selected for use with the disclosed methods.

In particular non-limiting examples, the FTI for use with disclosed methods is FTI-277, FTI-2153 or BZA-5B.

C. Administration of Therapeutic Agents

One skilled in the art can readily determine a therapeutically effective amount of an agent to be administered to a given subject by taking into account several factors, such as the size and weight of the subject; the extent of disease progression; the age, health and sex of the subject; the route of administration; whether the administration is regional or systemic; and the specific type of agent to be administered. One skilled in the art can also readily determine an appropriate dosage regimen for administering to a subject an agent that inhibits HDV.

For example, an effective amount of a therapeutic agent can be based on the approximate body weight of a subject to be treated. Such effective amounts can be administered by any suitable route, such as, for example, intravenously or locally into the salivary gland.

One skilled in the art can also readily determine an appropriate dosage regimen for the administration of a therapeutic agent disclosed herein to a given subject. For example, a therapeutic agent can be administered to the subject once (e.g., as a single injection or deposition). Alternatively, a therapeutic agent can be administered once or twice daily to a subject for a period of from about three to about twenty-eight days, more particularly from about seven to about ten days.

Therapeutic agents can be administered to a subject in need of treatment using any suitable means known in the art. Methods of administration include, but are not limited to, intraductal, intradermal, intramuscular, intraperitoneal, parenteral, intravenous, subcutaneous, vaginal, rectal, intranasal, inhalation, oral or by gene gun. Intranasal administration refers to delivery of the compositions into the nose and nasal passages through one or both of the nares and can comprise delivery by a spraying mechanism or droplet mechanism, or through aerosolization of the therapeutic agent. Administration of the compositions by inhalant can be through the nose or mouth via delivery by spraying or droplet mechanisms. Delivery can be directly to any area of the respiratory system via intubation. Parenteral administration is generally achieved by injection. Injectables can be prepared in conventional forms, either as liquid solutions or suspensions, solid forms suitable for solution of suspension in liquid prior to injection, or as emulsions. Injection solutions and suspensions can be prepared from sterile powders, granules, and tablets. Administration can be systemic or local (such as directly into the salivary gland). In some embodiments of the present disclosure, administration occurs by directly delivery to the salivary gland, such as by retrograde instillation.

Therapeutic agents can be administered in any suitable manner, preferably with pharmaceutically acceptable carriers. Pharmaceutically acceptable carriers are determined in part by the particular composition being administered, as well as by the particular method used to administer the composition. Accordingly, there is a wide variety of suitable formulations of pharmaceutical compositions of the present disclosure.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

In some embodiments, a single agent is administered to the subject in need of treatment. In other embodiments, two or more agents (such as 2, 3, 4, 5, or more) are administered to the subject. When two or more agents are administered to the subject, the agents can be administered simultaneously (or within quick succession, such as within minutes of each other), or they can be administered at different times. For example, two or more agents can be administered one hour, twelve hours, one day, two days, five days, one week, two weeks or one month apart.

In some embodiments, an HDV inhibitor can be administered to a subject in combination with one or more additional treatments for lymphoma, such as radiation therapy, chemotherapy, stem cell transplant, immunotherapy and/or surgery.

The following examples are provided to illustrate certain particular features and/or embodiments. These examples should not be construed to limit the disclosure to the particular features or embodiments described.

EXAMPLES

Example 1: Hepatitis Delta Virus (HDV) Detected in Sjögren's Syndrome Salivary Glands This example describes the identification of HDV nucleic acid and protein in the salivary gland of patients with Sjögren's syndrome. This example further demonstrates that mice transduced with recombinant AAV expressing HDV small and large antigens develop a disease that mimics primary Sjögren's syndrome in humans.

HDV Detected in pSS Salivary Gland

All primary Sjögren's syndrome patients contributing to this study met the European-American classification criteria for diagnosis of primary Sjögren's syndrome. Microarray analysis of RNA isolated from minor salivary gland tissue from healthy volunteers and Sjögren's syndrome patients was performed using a viral microarray. This method can identify RNA viruses and RNA transcripts of actively replicating DNA viruses within the affected salivary gland tissue. The viral microarray contains over 3000 probes for virus families known to infect vertebrates. Probes were designed to detect viral sequences shared with multiple members across a viral family (Wong et al., *Genome Biol* 8:R93, 2007). This approach was used to offer the most coverage in detection of viral signatures in the affected tissue with a limited number of probes.

Analysis of viral sequences in salivary gland tissue identified the presence of hepatitis delta virus (HDV) significantly increased in over 50% of the pSS patients compared to healthy volunteers (FIG. 1A). Hepatitis delta virus is a negative sense, single stranded RNA virus (Casey, J. L., *Hepatitis delta virus*, Springer, 2006). The 1694 nucleotide viral genome contains a single open reading frame that undergoes adenosine deamination by ADAR-1 at the initial stop codon rendering two distinct hepatitis delta antigens (HDAg). The small delta antigen (S-HDAg) is responsible for initiation of RNA genome replication and is expressed early in the infection cycle. The large antigen (L-HDAg) is expressed in later stages of viral infection and plays a role in viral packaging. The HDV genome is replicated using a double rolling-circle model of replication similar to plant viroids (Flores et al., *RNA Biol* 8:200-206, 2011). This replication method initiates with the production of an antigenome that serves as a template for HDAg mRNA synthesis and full HDV genome production. Confirmation of viral sequence was performed using a gene specific PCR amplification protocol and deep sequencing (Hamatake and Lau, *Hepatitis B and D protocols*, Humana Press, 2004). HDV sequences with homology to clades 1 and 3 were present in the patients sequenced (FIG. 1C and FIG. 1D).

Patients that tested positive for HDV by microarray analysis were further analyzed for the presence of antigen in the affected salivary gland tissue. Confocal immunofluorescent antigen detection with an HDV specific affinity purified antibody against amino acids 96-111 of delta antigen (accession M21012, Yenzyme, Calif.) produced a nuclear speckled and cytoplasmic localization pattern suggestive of a combined S-HDAg and L-HDAg cytoplasmic expression (FIG. 1B).

Local HDV in Absence of Detectible HBV

Figure 2A:
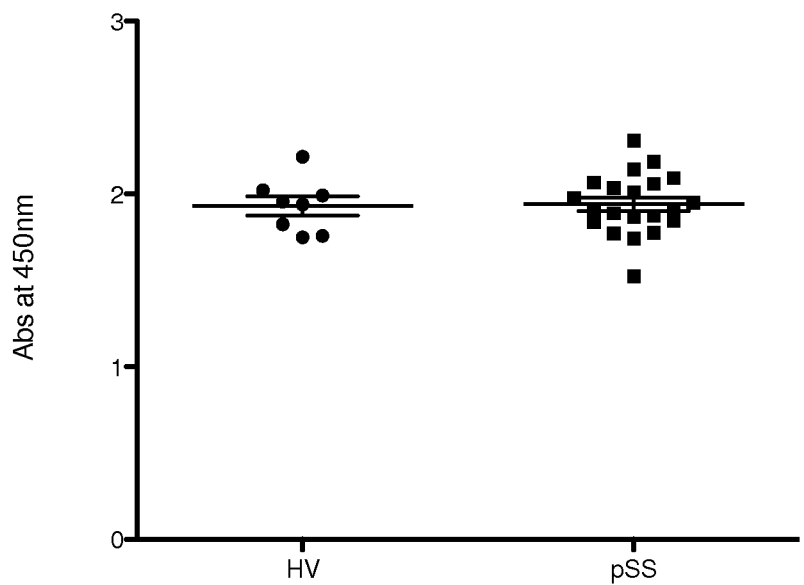
FIGS. 2A-2B: Primary Sjögren's syndrome patients with detected levels of HDV in salivary gland tissue tested negative for anti-HDV antibody and anti-hepatitis B virus (HBV) core antigen (HBVc) antibody.
Figure 2B:
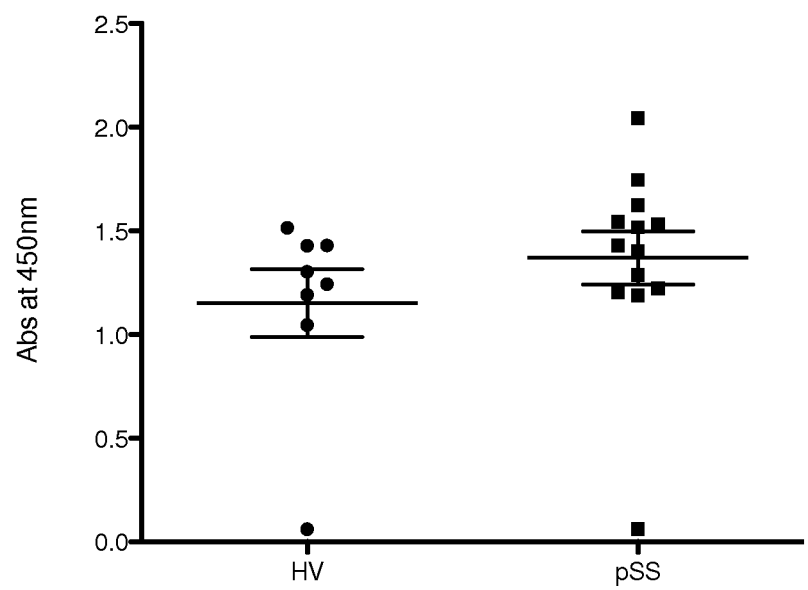

Classically, HDV is thought to require a helper virus, hepatitis B virus (HBV), for packaging and transmission (Casey, J. L., *Hepatitis delta virus*, Springer, 2006). Primary Sjögren's syndrome patients that possessed detectible HDV RNA in minor salivary gland tissue were negative for HBV in microarray and PCR. Probe intensity of over 100 microarray probes recognizing sequences from the Hepadnaviridae family showed no significant difference between healthy volunteers and the pSS cohort tested (Table 1). In addition, there was a lack of significant correlation between the intensity of the Hepadnaviridae microarray probes with the HDV microarray probe intensity (Table 1). Serum anti-hepatitis B virus core antibodies (HBcAb) or hepatitis B surface antigen were not detected in pSS patients that were positive for HDAg in salivary gland tissue (FIG. 2B and Table 2, respectively). This is in line with previous reports of similar rates of HBcAb detection between healthy controls and pSS (Ram et al., *Autoimmun Rev* 7:621-625, 2008). Similarly, no anti-HDV antigen antibodies were detected in serum from pSS subjects using a commercially available HDV antibody detection ELISA kit designed to detect HDV in an active HBV:HDV co-infection (International Immuno-Diagnostics) (FIG. 2A).

TABLE 1

A lack of positive significant correlation was noted between level of hepatitis delta virus (HDV) probe intensity and probes that recognize viruses from the Hepadnaviridae family. Pearson correlation coefficient (PCC) was calculated between HDV and Hepadnaviridae probe intensities within the primary Sjögren's syndrome co-hort.

| Accession (GI) Number | Probe Name | Similarity Score |
|---|---|---|
| 9628827 | gi_29_9628827 | 0.24231684 |
| 22256030 | gi_29_22256030 | 0.18431515 |
| 9628827 | gi_22_9628827 | 0.18092173 |
| 22256030 | gi_22_22256030 | 0.12675416 |
| 9625568 | gi_110_9625568 | 0.119371355 |
| 49246207 | gi_20_49246207 | 0.115206 |
| 9625568 | gi_57_9625568 | 0.1134941 |
| 9630370 | gi_20_9630370 | 0.109876156 |
| 21326584 | gi_16_21326584 | 0.10851103 |
| 49246207 | gi_109_49246207 | 0.10802859 |
| 9630370 | gi_8_9630370 | 0.102727175 |
| 9630370 | gi_19_9630370 | 0.098847866 |
| 21326584 | gi_9_21326584 | 0.0906294 |
| 48696604 | gi_75_48696604 | 0.08130163 |
| 9626719 | gi_104_9626719 | 0.07727754 |
| 21326584 | gi_14_21326584 | 0.068612814 |
| 9626719 | gi_20_9626719 | 0.05911553 |
| 9630370 | gi_15_9630370 | 0.054857254 |
| 48696604 | gi_46_48696604 | 0.051366568 |
| 9626714 | gi_9_9626714 | 0.048202217 |
| 22256030 | gi_1_22256030 | 0.04753691 |
| 9626719 | gi_116_9626719 | 0.04072529 |
| 9626719 | gi_44_9626719 | 0.038819313 |
| 9630370 | gi_15_9630370 | 0.03727156 |
| 9625568 | gi_20_9625568 | 0.03624797 |
| 9630370 | gi_14_9630370 | 0.03396666 |
| 21326584 | gi_5_21326584 | 0.03324592 |
| 21326584 | gi_10_21326584 | 0.033089936 |
| 9628827 | gi_1_9628827 | 0.03262317 |
| 9626719 | gi_101_9626719 | 0.03262317 |
| 48696604 | gi_104_48696604 | 0.03262317 |
| 49246207 | gi_107_49246207 | 0.03262317 |
| 21326584 | gi_11_21326584 | 0.03262317 |
| 48696569 | gi_111_48696569 | 0.03262317 |
| 49246207 | gi_116_49246207 | 0.03262317 |
| 48696569 | gi_118_48696569 | 0.03262317 |
| 48696604 | gi_118_48696604 | 0.03262317 |
| 48696569 | gi_120_48696569 | 0.03262317 |
| 9626719 | gi_14_9626719 | 0.03262317 |
| 9628827 | gi_14_9628827 | 0.03262317 |
| 22256030 | gi_15_22256030 | 0.03262317 |
| 48696569 | gi_15_48696569 | 0.03262317 |
| 9628827 | gi_15_9628827 | 0.03262317 |
| 21326584 | gi_18_21326584 | 0.03262317 |
| 49246207 | gi_18_49246207 | 0.03262317 |
| 9626714 | gi_18_9626714 | 0.03262317 |
| 9626714 | gi_19_9626714 | 0.03262317 |
| 21326584 | gi_22_21326584 | 0.03262317 |
| 21326584 | gi_22_21326584 | 0.03262317 |
| 21326584 | gi_23_21326584 | 0.03262317 |
| 21326584 | gi_26_21326584 | 0.03262317 |
| 9626714 | gi_27_9626714 | 0.03262317 |
| 49246207 | gi_45_49246207 | 0.03262317 |
| 48696569 | gi_47_48696569 | 0.03262317 |
| 9626719 | gi_50_9626719 | 0.03262317 |
| 49246207 | gi_51_49246207 | 0.03262317 |
| 9626719 | gi_51_9626719 | 0.03262317 |
| 48696604 | gi_53_48696604 | 0.03262317 |

TABLE 1-continued

A lack of positive significant correlation was noted between level of hepatitis delta virus (HDV) probe intensity and probes that recognize viruses from the Hepadnaviridae family. Pearson correlation coefficient (PCC) was calculated between HDV and Hepadnaviridae probe intensities within the primary Sjögren's syndrome co-hort.

| Accession (GI) Number | Probe Name | Similarity Score |
|---|---|---|
| 49246207 | gi_53_49246207 | 0.03262317 |
| 22256030 | gi_58_22256030 | 0.03262317 |
| 22256030 | gi_6_22256030 | 0.03262317 |
| 9628827 | gi_6_9628827 | 0.03262317 |
| 9625568 | gi_65_9625568 | 0.03262317 |
| 22256030 | gi_7_22256030 | 0.03262317 |
| 9626714 | gi_73_9626714 | 0.03262317 |
| 9626719 | gi_73_9626719 | 0.03262317 |
| 49246207 | gi_76_49246207 | 0.03262317 |
| 49246207 | gi_78_49246207 | 0.03262317 |
| 9625568 | gi_79_9625568 | 0.03262317 |
| 9628827 | gi_8_9628827 | 0.03262317 |
| 9626719 | gi_83_9626719 | 0.03262317 |
| 9625568 | gi_92_9625568 | 0.03262317 |
| 22256030 | gi_8_22256030 | 0.03252393 |
| 48696569 | gi_85_48696569 | 0.031067312 |
| 48696569 | gi_87_48696569 | 0.030825615 |
| 9625568 | gi_90_9625568 | 0.030416071 |
| 9625568 | gi_22_9625568 | 0.027078986 |
| 22256030 | gi_7_22256030 | 0.027070403 |
| 48696604 | gi_20_48696604 | 0.026582897 |
| 9625568 | gi_46_9625568 | 0.023499012 |
| 9626714 | gi_10_9626714 | 0.02169931 |
| 9625568 | gi_77_9625568 | 0.020311117 |
| 48696604 | gi_73_48696604 | 0.010974407 |
| 21326584 | gi_25_21326584 | 0.007618249 |
| 9625568 | gi_108_9625568 | 0.006661952 |
| 9628827 | gi_17_9628827 | −0.009503603 |
| 48696569 | gi_52_48696569 | −0.009588838 |
| 22256030 | gi_12_22256030 | −0.020192146 |
| 48696569 | gi_17_48696569 | −0.02758348 |
| 48696569 | gi_109_48696569 | −0.07066083 |
| 48696604 | gi_44_48696604 | −0.09997618 |
| 9628827 | gi_3_9628827 | −0.10156798 |
| 48696604 | gi_18_48696604 | −0.122792244 |
| 9630370 | gi_3_9630370 | −0.13456202 |
| 48696604 | gi_116_48696604 | −0.13479269 |
| 21326584 | gi_13_21326584 | −0.16312766 |
| 9630370 | gi_14_9630370 | −0.18382204 |
| 9628827 | gi_8_9628827 | −0.24456 |
| 22256030 | gi_9_22256030 | −0.26242125 |
| 9630370 | gi_13_9630370 | −0.270427 |
| 9630370 | gi_9_9630370 | −0.3615979 |
| 21326584 | gi_21_21326584 | −0.66936874 |
| 21326584 | gi_16_21326584 | −0.69898057 |
| 9630370 | gi_23_9630370 | −0.7722173 |

Inapparent or occult HBV infections have been observed in HBV:HDV co-infected patients and HDV co-infection has been reported to hinder the replication and detection of HBV (Raimondo et al., *J Hepatol* 46:160-170, 2007; Arribas et al., *Aids* 19:1361-1365, 2005; Colombo et al., *J Hepatol* 12:64-69, 1991). Alone, HDV has been shown to persist for extended periods in the absence of an active HBV infection in vitro and autonomous expression of HDV antigens have been shown to induce an interferon response. Prior studies have evaluated HBV in pSS patient populations and have found similar or lower HBV infection rates in pSS patient cohorts compared to the general population (Ram et al., *Autoimmun Rev* 7:621-625, 2008; Marcos et al., *Autoimmun Rev* 8:616-620, 2009). Chen et al. suggested HBV infections may actually protect individuals from developing pSS (Chen et al., *Clin Rheumatol* 31:309-315, 2012). Together, the data disclosed herein indicates that HDV RNA and antigen expression can occur locally within the salivary gland in the absence of a detectable HBV infection.

HDV and Clinical Correlations

Several correlations were observed between patient clinical results and the level of HDV in salivary gland tissue. Levels of HDV positively correlated with total IgG, anti-nuclear antibody (ANA) and anti-SSA antibody values (Table 2) but did not with serum anti-SSB antibody levels.

The SSA/Ro ribonucleoprotein complexes recognized by anti-SSA antibodies are comprised of RNA and either SSA/R052(TRIM21) or SSA/Ro60(TROVE2). Prior studies have detailed an association between anti-SSA/Ro52(TRIM21) and Sjögren's syndrome, while anti-SSA/Ro60 was more associated with systemic lupus erythematosus (SLE) (Dugar et al., Postgrad Med J 86:79-82, 2010; Menendez et al., Autoimmunity 46:32-39, 2013). TRIM21 is an intracellular Fc receptor that has been shown to recognize pathogens that internalize with bound antibodies (Keeble et al., Proc Natl Acad Sci USA 105:6045-6050, 2008; McEwan et al., Nat Immunol 14:327-336, 2013). Binding of IgG coated intracellular viral particles to TRIM21 targets viral particles for degradation and stimulates proinflammatory cytokine production. The identified correlation of HDV levels in salivary gland tissue with anti-SSA levels and association of antibodies to intracellular viral sensing SSA/R052(TRIM21) with Sjögren's syndrome further suggests the potential of a viral trigger in the development or propagation of pSS.

Active HDV infections have been associated with altered liver functions most often characterized by altered levels of liver enzymes, alanine aminotransferase (ALT) and aspartate aminotransferase (AST) detected in serum. The levels of ALT and AST were within standard clinical range and did not correlate with increased HDV presence in salivary gland tissue (Table 2). The identification of HDV present in pSS salivary gland tissue, lack of a detectible systemic HBV or HDV infection and normal liver enzyme levels are suggestive of a novel type of chronic HDV infection.

TABLE 2

Correlations between clinical parameters and HDV levels in minor salivary gland biopsy. Levels of anti-nuclear antibodies (ANA) and anti-SSA/Ro antibody positively correlated with levels of HDV. No correlation was observed between HDV and levels of serum anti-SSB/La antibody. IgG levels in serum positively correlated with levels of HDV. Liver function tests, including measurement of serum aspartate aminotransferase (AST) and alanine aminotransferase (ALT) were within normal clinical range and did not correlate with levels of HDV detected in salivary gland tissue.

| Variable | By Variable | Correlation | Signif. Prob. |
| --- | --- | --- | --- |
| Anti-ANA antibody | HDV | 0.4344 | 0.0383* |
| Anti-SSA/Ro Antibody | HDV | 0.4363 | 0.0374* |
| Anti-SSB/La Antibody | HDV | 0.1767 | 0.4199 |
| IgG | HDV | 0.5561 | 0.0088* |
| IgM | HDV | −0.1523 | 0.5098 |
| AST | HDV | −0.0532 | 0.8188 |
| ALT | HDV | −0.2373 | 0.3003 |

*$p < 0.05$, n = 21-23.

HDV Antigens Induce pSS in Mice

Figure 6:
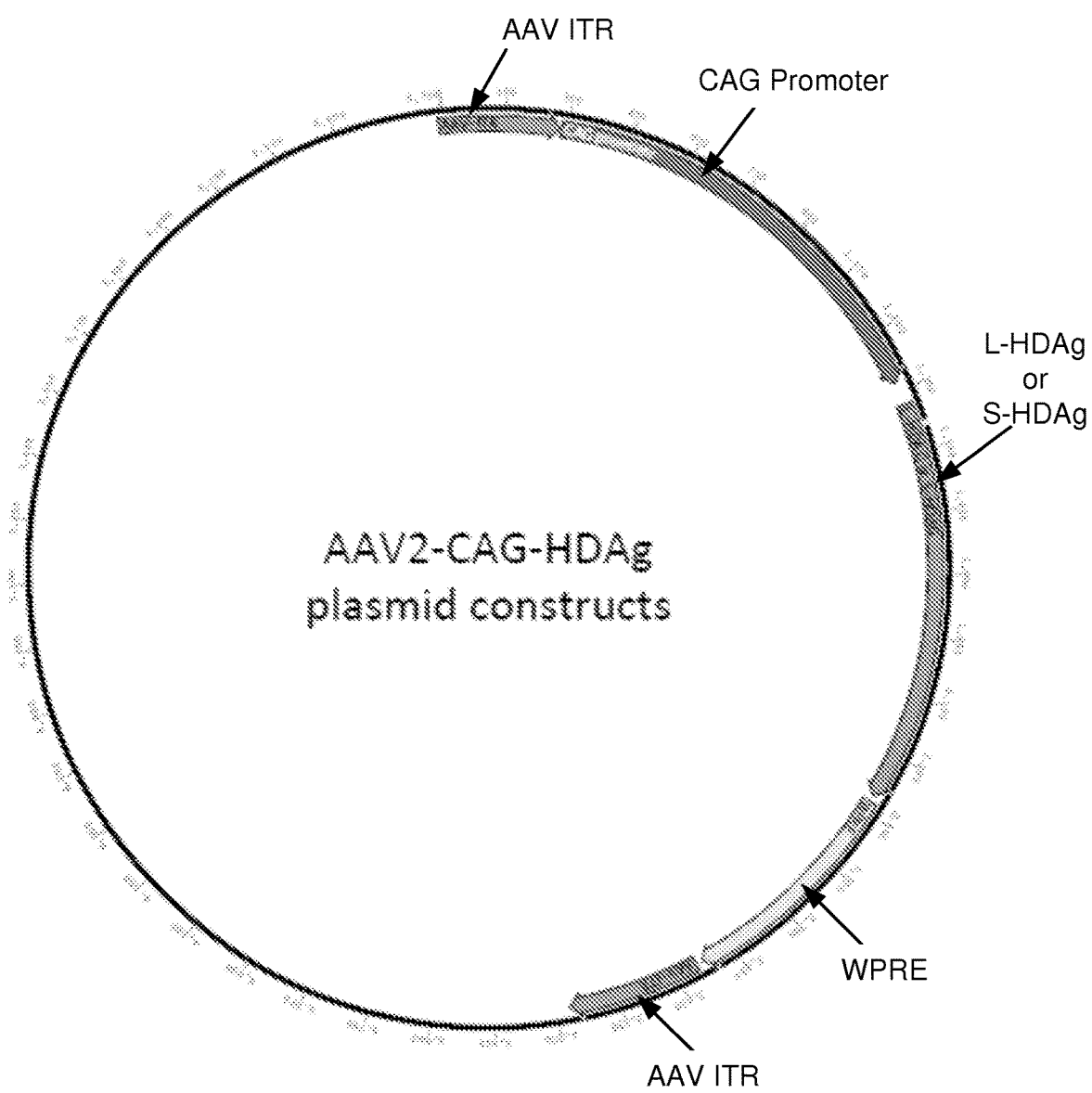
FIG. 6: Depiction of AAV2-CAG-HDAg plasmids used for production of AAV1-CAG-Large-HDAg and AAV2-CAG-Small-HDAg viral vectors. Capped by AAV2 inverted terminal repeat (ITR) sequence, the CAG promoter was used to drive expression of either the small HDV antigen (S-HDAg) or the large HDV antigen (L-HDAg). WPRE is a woodchuck hepatitis virus posttranscriptional regulatory element (WPRE).

The key to identifying a viral trigger in the development of viral-mediated autoimmunity is establishing evidence that the virus is able to initiate development of disease phenotype. The challenge of evaluating HDV in the salivary gland tissue in the absence of HBV was delivering the viral antigens to the glands in the absence of a true helper virus. Therefore, to evaluate HDV antigen (HDAg) for the potential to initiate development of Sjögren's syndrome-like symptomology, recombinant adeno-associated virus serotype 2 (rAAV-2) was used to deliver viral antigen transgenes to female C57-BL6 mouse salivary glands through retrograde cannulation. The rAAV-2 viral particles contained expression cassettes for luciferase (control), S-HDAg, L-HDAg or a combination of S-HDAg and L-HDAg (S-HDAg/L-HDAg) (FIG. 6).

Figure 3:
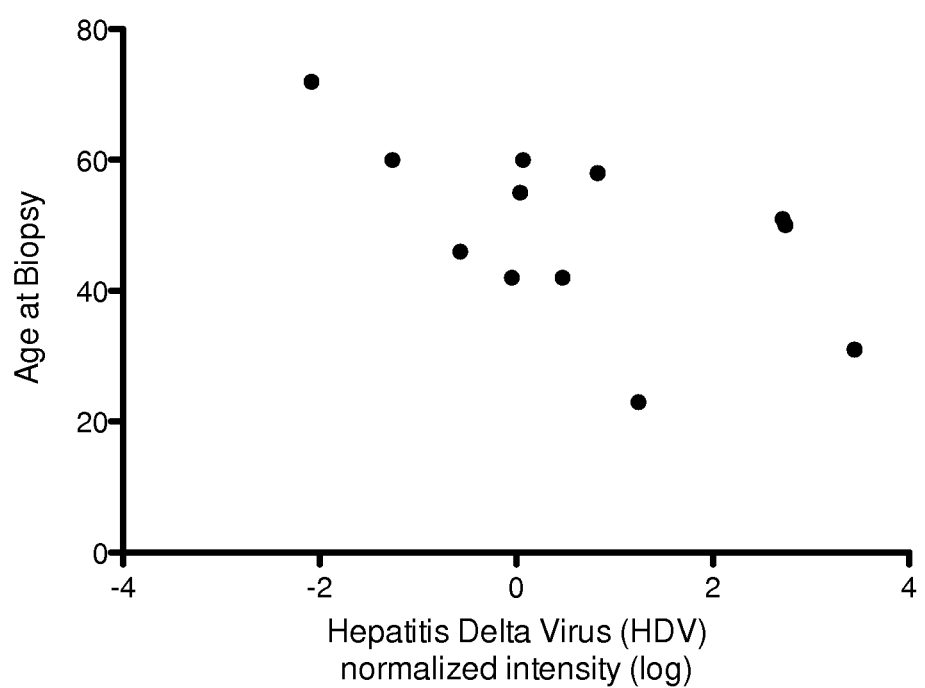
FIG. 3: Negative trend between level of HDV RNA detected in salivary gland and age of pSS patient at time of biopsy. Pairwise correlation=−0.5737, n=12, p=0.0511.

Recombinant AAV was produced and utilized for cannulation of submandibular salivary glands in female C57/BL6 mice as previously reported (Voutetakis et al., Proc Natl Acad Sci 101:3053-3058, 2004). Viral aliquots of rAAV2-HDAg used for cannulation were spiked with 10% rAAV2-luciferase to confirm effective cannulation. One week post cannulation, mice were monitored for luciferase expression in the salivary gland tissue region by intraperitoneal injection with luciferin and imaging of luminescence using the Xenogen imaging system (Weller et al., Nat Med 16:662-664, 2010). Mice that had detectible levels of luciferase activity were utilized for the study. At the termination of the study, secondary detection of antigen expression in salivary gland was confirmed by PCR (FIG. 3).

Figure 4A:
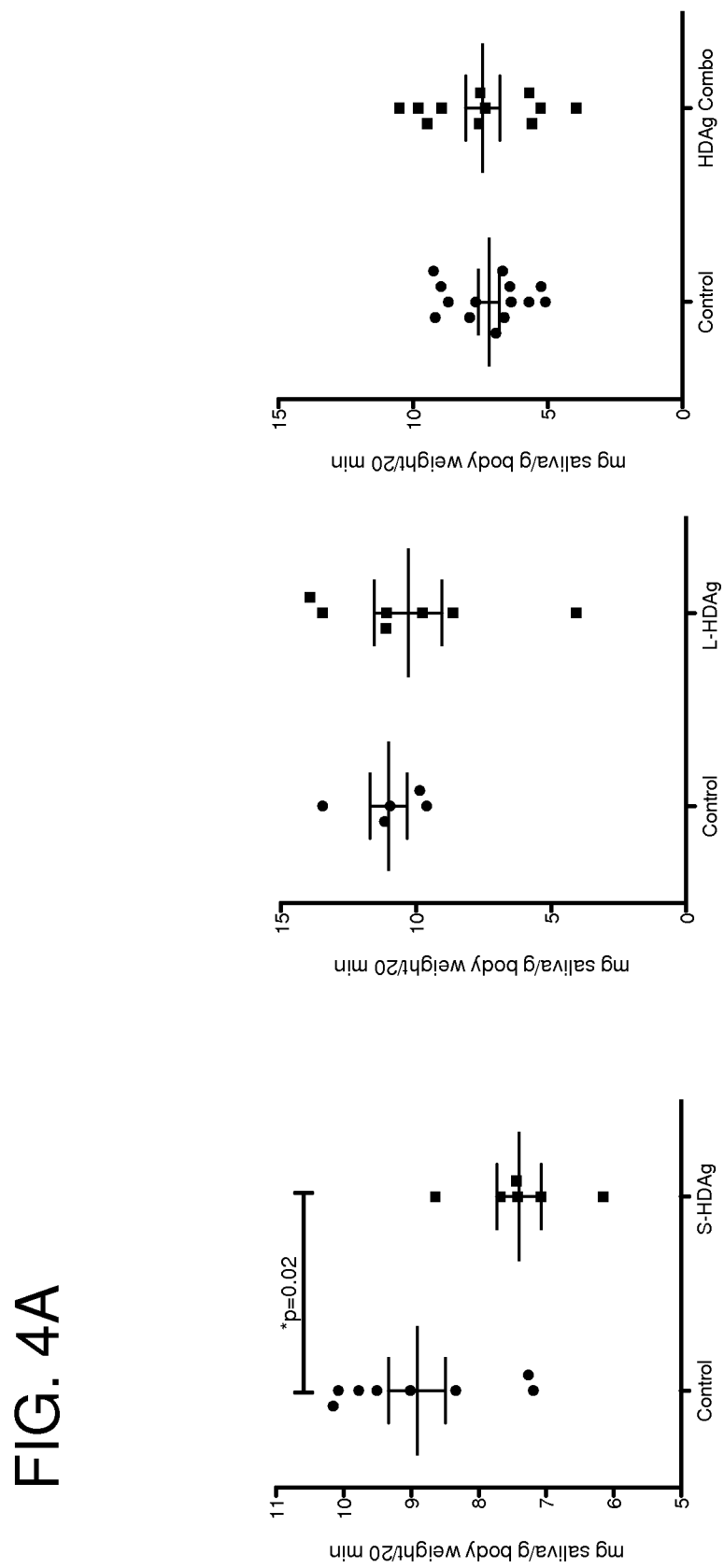
FIGS. 4A-4H: Stimulated saliva, lymphocytic foci and autoantibody profiles in HDAg-mouse model correlate with HDV-positive pSS.

Mice were monitored for pilocarpine stimulated saliva flow at 1 month and 3 months post cannulation. Of the three experimental groups tested, mice expressing the S-HDAg had a significant decrease in stimulated saliva flow at 3 months post cannulation (FIG. 4A). No change in pilocarpine stimulated saliva production was noted in mice that expressed the L-HDAg or combined S-HDAg/L-HDAg. Together, these data suggest that the expression of S-HDAg, which is representative of early stages of HDV infection, possesses the capacity to impact stimulated saliva production.

Figure 4B:
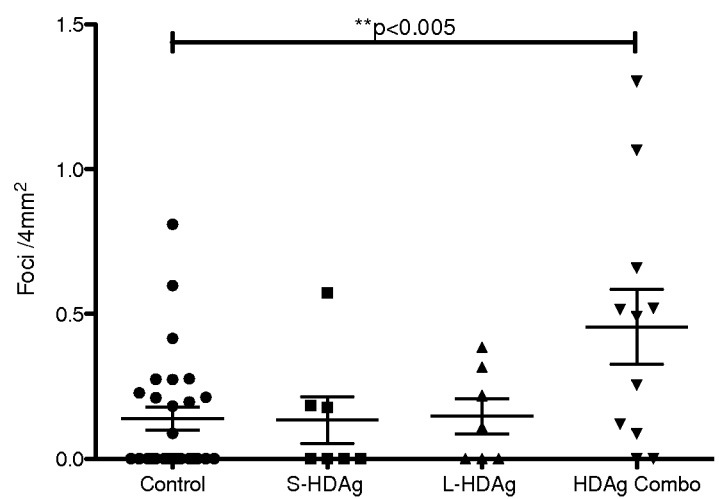
Figure 4C:
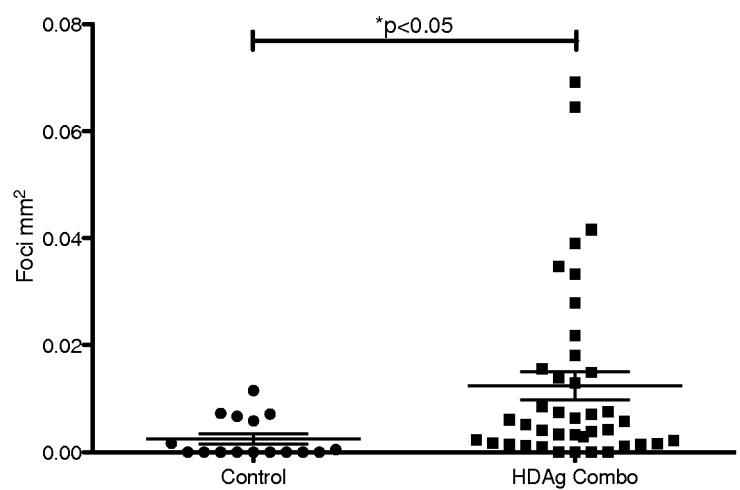

Focal accumulation of B-lymphocytes and T-lymphocytes within the affected salivary gland is often reported in pSS patients. Salivary glands were assessed for the development of foci at the termination of the study. Mice that were cannulated with the combined S-HDAg/L-HDAg showed an increase in foci (FIG. 4B). No significant increase in foci was noted with singular expression of S-HDAg or L-HDAG to the salivary glands. The area of the foci in the treated animals was also significantly increased in mice that were cannulated with rAAV2-S-HDAg/L-HDAg compared to foci area in the control mice (FIG. 4C). Expression of both S-HDAg and L-HDAg, representative of protein expression in later stages HDV infection, possesses the capacity to induce significant focal accumulation of lymphocytes in salivary gland tissue.

Figure 4D:
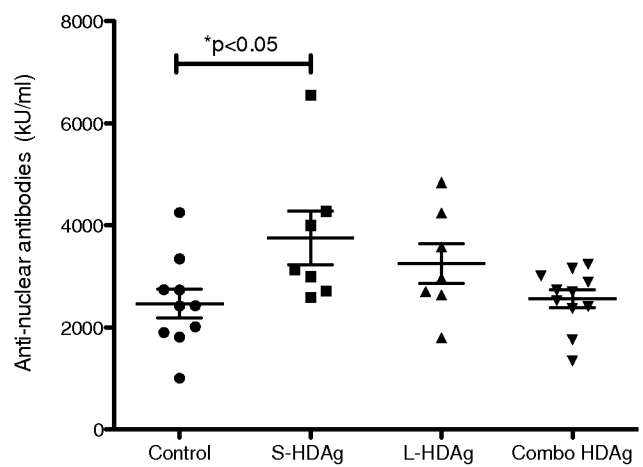
Figure 4E:
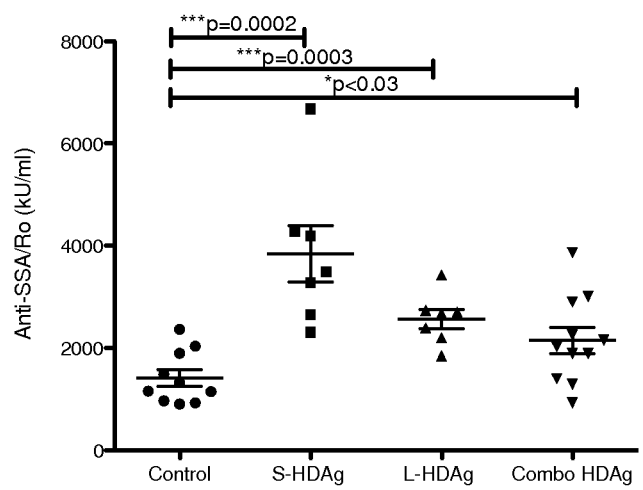
Figure 4F:
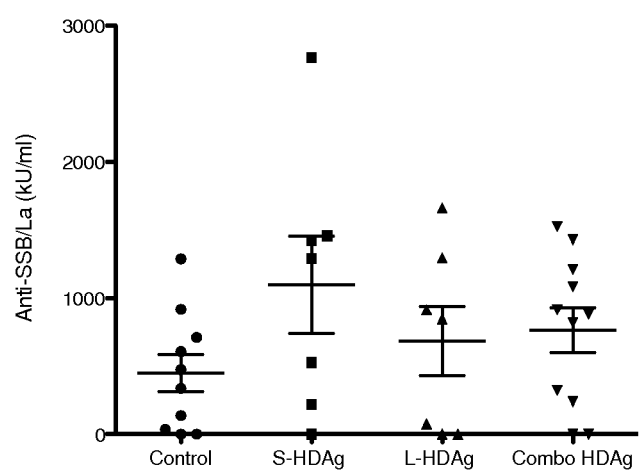
Figure 4G:
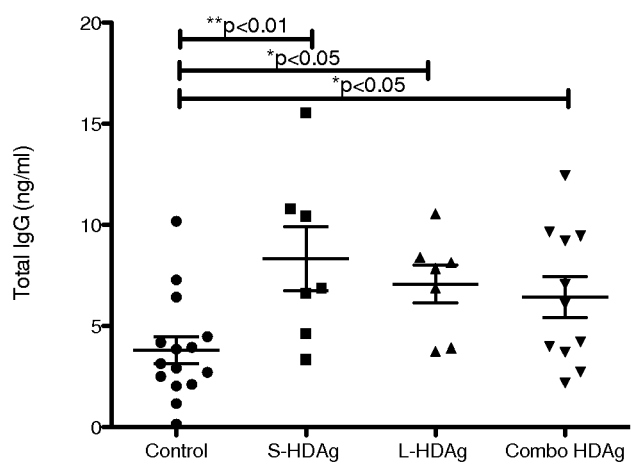

Analysis of the autoantibody profiles in mice cannulated with the delta antigens identified the development of a similar autoantibody profile to the HDV positive pSS patient cohort. Mice transduced with AAV-S-HDAg showed a significant upregulation of anti-nuclear antibodies (ANA) compared with the control group (FIG. 4D). There was a trend of increased anti-ANA in the mice expressing L-HDAg or the combination of delta antigens. The mice cannulated with S-HDAg, L-HDAg or S-HDAg/L-HDAG all developed significant levels of anti-SSA (anti-Ro) antibodies compared to rAAV2-luciferase transduced controls (FIG. 4E). A lack of development of anti-SSB (La) antibody was noted across all HDV study groups (FIG. 4F). All three groups of HDV antigen treated mice showed a significant increase in total IgG levels in serum (FIG. 4G). This autoantibody profile correlates with the profile observed in HDV-positive pSS patients tested (FIG. 3C). Prior studies have noted the development of autoantibodies in patients with chronic HDV infections, consisting of ANA, liver-kidney microsomal antibodies (LKM) and smooth muscle antibody (SMA) among others (Zauli et al., Clin Exp Immunol 78:80-84, 1989; Amengual et al., Clin Exp Immunol 78:80-

84, 1989; Philipp et al., *Biomed Pharmacother* 49:344-349, 1995). The data disclosed herein together with prior reports of autoantibodies in the presence of chronic HDV further support the ability of HDV to trigger autoimmunity. The type of autoantibody profile developed in the presence of HDV may be dependent on the tissues with active HDV gene expression.

Figure 4H:
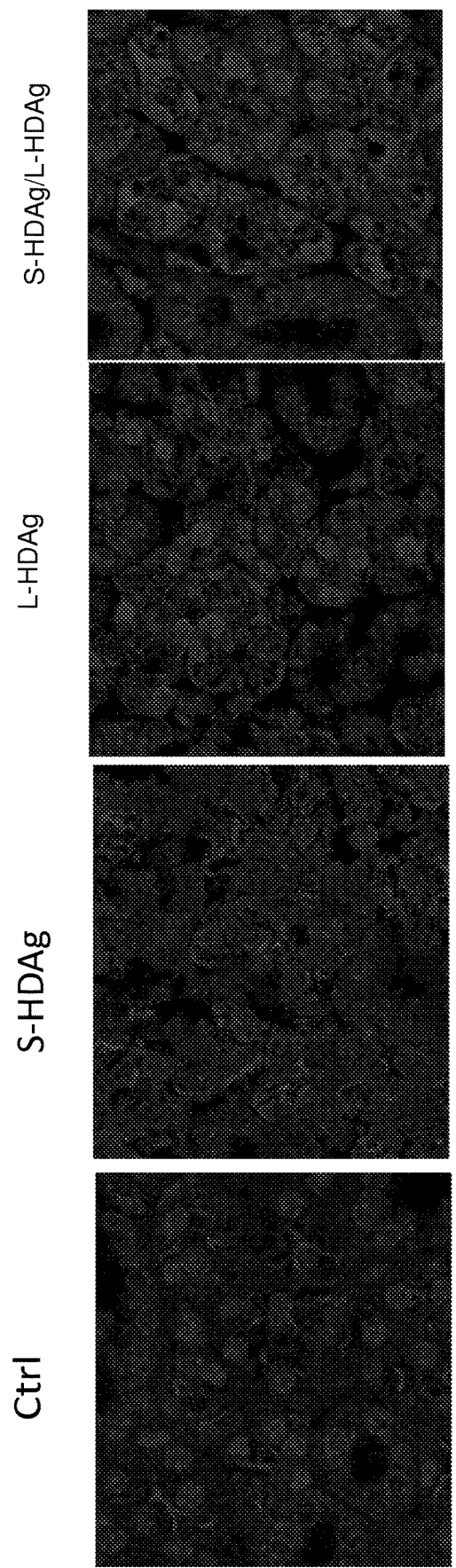

Detection of the delta antigens in the mouse salivary glands rendered a similar pattern to HDV positive pSS immunohistochemical staining. As shown in FIG. 4H, mice that were cannulated with S-HDAg, L-HDAg or a combination of the two delta antigens showed staining patterns characteristic to reported HDV localization. Salivary glands that were cannulated with rAAV2-S-HDAg rendered a speckled staining pattern for HDAg within the nucleus and accumulation within the cytoplasm. Salivary glands that were cannulated with rAAV2-L-HDAg presented with accumulation of antigen within the cytoplasm but lacked a detectable nuclear localization. The salivary glands that were cannulated with a combination of the delta antigens showed a predominant staining pattern in the cytoplasm. The salivary glands that were transduced with L-HDAg alone or the combined delta antigens presented a similar staining pattern to that observed in the pSS minor salivary glands.

Viral Trigger for Sjögren's Syndrome

This study identified the unique presence of hepatitis delta virus in salivary gland tissue of pSS patients using a custom viral microarray. Subsequent confirmation of HDV RNA and antigen expression validated the initial microarray detection of HDV in the United States cohort of pSS patients tested. Expression of HDV antigens in the salivary glands of healthy female C57/BL6 mice recapitulating the phenotypic development of Sjögren's syndrome, supporting the hypothesis that HDV is able to trigger development of pSS. This conclusion is supported by the altered saliva production, increased lymphocytic infiltrates in the salivary glands, and development of an antibody profile similar to that observed in HDV positive pSS patients. The studies disclosed herein indicate that HDV is capable of instigating or propagating the development of autoimmunity and a Sjögren's syndrome phenotype.

Disease progression in the HDV animal model disclosed herein follows the reported development of disease phenotype in Sjögren's syndrome patient populations and correlates with the HDV infection timeline. As detailed in FIG. 5, the small delta antigen is expressed early in the HDV infection cycle. Expression of S-HDAg in mouse salivary gland initiated reduction of saliva flow and significant development of anti-SSA, ANA and IgG antibodies. Later stages of HDV infection transitions to L-HDAg synthesis after ADAR-1 mediated mutation of the S-HDAg amber stop codon. In the current study, expression of L-HDAg alone did not reduce saliva production, foci development or produce additive autoantibody levels. During a natural HDV infection, L-HDAg is expressed in the presence of S-HDAg and both antigens form the ribonucleoprotein complex with the RNA genome for packaging into the HBV viral coat. Introduction of both S-HDAg and L-HDAg into the mouse salivary gland rendered a significant increase in lymphocytic infiltrates developing in the transduced salivary gland. The expression of early stage and late stage HDV antigens mimicked the development of disease that has been reported in both animal models and in humans diagnosed with primary Sjögren's syndrome (FIG. 5). Autoantibodies have been reported to appear in advance of inflammation and development of lymphocytic lesion within the gland in both animal models and in humans (Theander et al., poster presentation at the 11th International Symposium on Sjögren's Syndrome, Athens, Greece, 2011).

Future Direction of HDV Treatment

Prior studies of hepatitis B virus (HBV) in pSS patient populations have not identified a connection between HBV infection and the development of Sjögren's syndrome. In line with these prior studies, the studies disclosed herein were unable to detect the presence of HBV antigen, antibody or viral sequence in the HDV-positive pSS samples tested. Therefore, these findings indicate that the development of disease does not rely on the presence of HBV, but on the deposition and chronic presence of HDV within the affected tissue.

Inhibitors of HDV have shown promise in the treatment of HBV:HDV superinfections. Prenylation inhibitors, including FTI-277 and FTI-2153, block post-translational farnesylation of the L-HDAg, thereby hindering packaging of HDV ribonucleoprotein complex in the HBV virion[23]. These small molecule drugs have shown potential in cancer treatment and blocking HDV viremia in a HBV-transgenic mouse model. Interferon-alpha based therapies have shown modest ability to inhibit chronic HDV (Arribas et al., *Aids* 19:1361-1365, 2005).

The study disclosed herein identified sequence homologous to HDV genotype 1 and HDV genotype 3 in pSS salivary gland tissue. Epidemiological studies have noted the presence of HDV genotype 1 throughout the world with concentrations in North America, Europe, Middle East, Northern Africa and Asia (Wedemeyer and Manns, *Nat Rev Gastroenterol Hepatol* 7:31-40, 2010). HDV genotype 3 is localized to South America. Testing for the presence of HDV occurs if there is evidence of current or past HBV infection. A majority of HBV:HDV infections resolve but are known to render a chronic HDV presence.

Example 2: Detection of HDV in Lymphoma

This example describes the detection of HDV nucleic acid in the salivary gland of a patient diagnosed with lymphoma, and in the parotid or submandibular glands of patients with pSS-associated lymphoma. The data described in this example further demonstrates that expression of HDV antigens in a mouse model results in the development of tertiary lymphoid structures (TLS) within salivary gland tissue.

Detection of HDV Nucleic Acid

Figure 7:
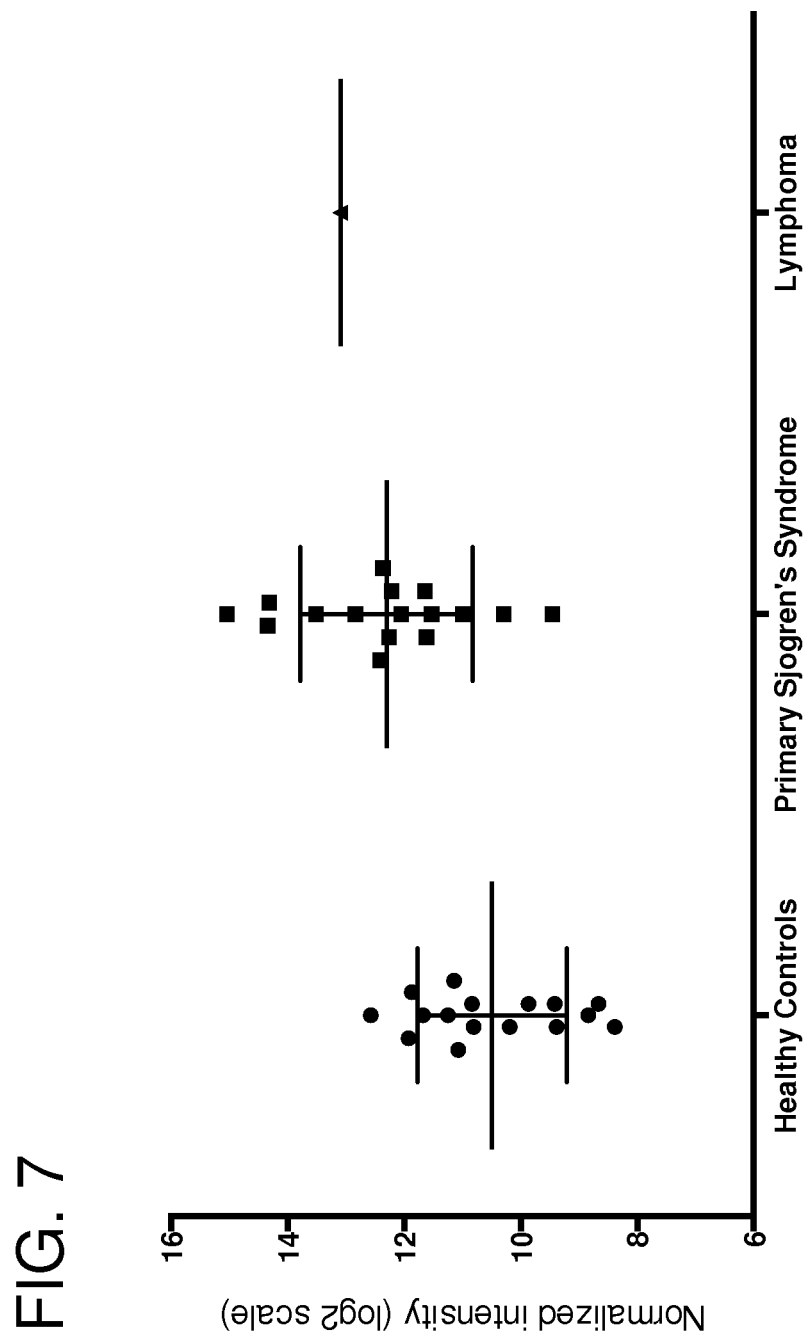
FIG. 7: Hepatitis delta virus (HDV) identified in a patient diagnosed with lymphoma. A biopsy from the minor salivary gland of a patient diagnosed with lymphoma was analyzed by viral microarray. Normalized HDV probe intensity of healthy controls, primary Sjögren's syndrome patients and the lymphoma patient are depicted in the graph. The lymphoma patient exhibited an elevated level of HDV compared to healthy controls.

Microarray analysis of RNA isolated from minor salivary gland tissue from healthy volunteers, patients with primary Sjögren's syndrome, or a patient diagnosed with lymphoma was performed using a viral microarray. This method can identify RNA viruses and RNA transcripts of actively replicating DNA viruses within the affected salivary gland tissue. The viral microarray contains over 3000 probes for virus families known to infect vertebrates. Probes were designed to detect viral sequences shared with multiple members across a viral family (Wong et al., *Genome Biol* 8:R93, 2007). As shown in FIG. 7, the patient diagnosed with lymphoma was positive for HDV in a minor salivary gland biopsy, exhibiting elevated levels of HDV compared to healthy controls.

Mouse Model Expressing HDV Antigens

To evaluate HDV antigen (HDAg) for the potential to initiate development of pathology indicative of lymphoma, recombinant adeno-associated virus serotype 2 (rAAV-2) was used to deliver viral antigen transgenes to female C57-BL6 mouse salivary glands through retrograde cannulation. The rAAV-2 viral particles contained expression cassettes for luciferase (control), S-HDAg, L-HDAg or a combination of S-HDAg and L-HDAg (S-HDAg/L-HDAg).

Recombinant AAV was produced and utilized for cannulation of submandibular salivary glands in female C57/BL6 mice as previously reported (Voutetakis et al., *Proc Natl Acad Sci* 101:3053-3058, 2004). Viral aliquots of rAAV2-HDAg used for cannulation were spiked with 10% rAAV2-luciferase to confirm effective cannulation. One week post cannulation, mice were monitored for luciferase expression in the salivary gland tissue region by intraperitoneal injection with luciferin and imaging of luminescence using the Xenogen imaging system (Weller et al., *Nat Med* 16:662-664, 2010). Mice that had detectible levels of luciferase activity were utilized for the study. At the termination of the study, secondary detection of antigen expression in salivary gland was confirmed by PCR.

Figure 8:
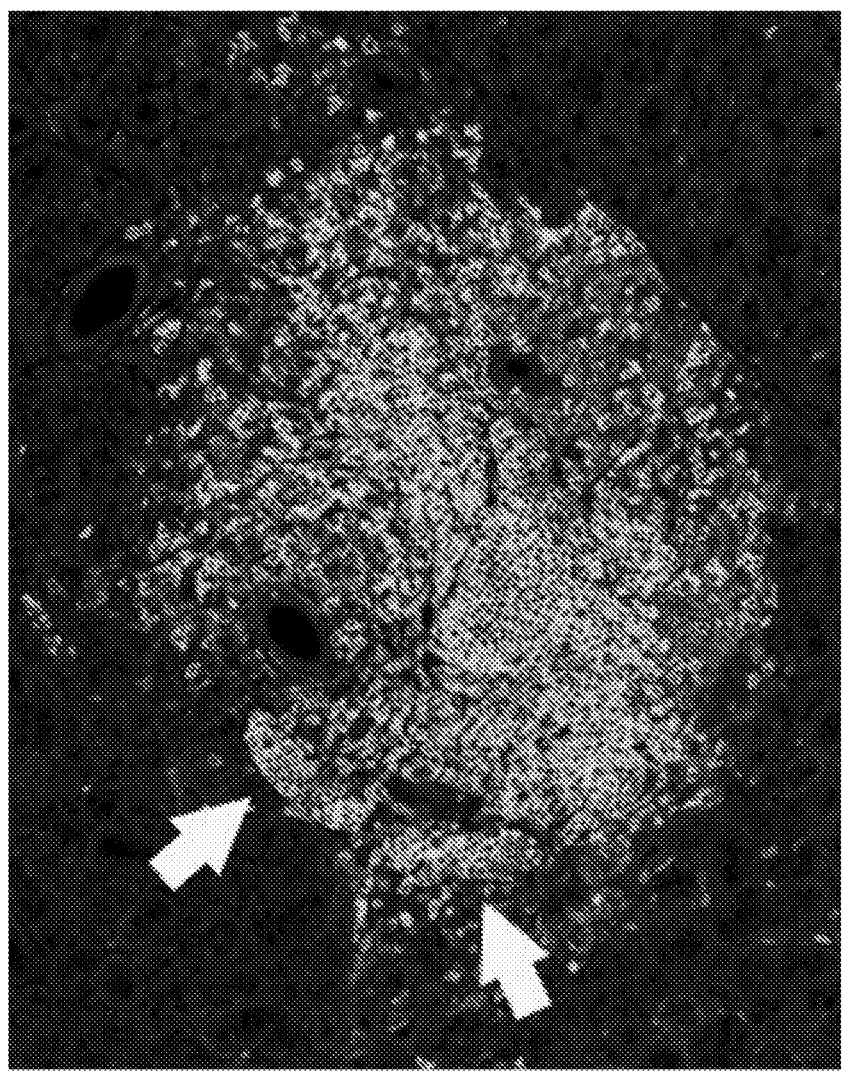
FIG. 8: Organized tertiary lymphoid structures (TLS) are present in mice expressing HDV antigen. Salivary glands were harvested from mice expressing HDV antigens at four months post cannulation. Formalin-fixed paraffin-embedded salivary gland tissue was immunostained for B cells and T cells. Organization of B and T cells is a characteristic of TLS and is a precursor to the development of lymphoma. Arrows depict connections to draining lymph nodes.

Salivary glands were harvested from mice expressing HDV antigens at four months post cannulation. Expression of HDV antigens in the salivary glands of these mice resulted in increased lymphocytic infiltrate accumulation within the salivary gland, including the presence of organized TLS within the focal lymphocytic lesions in the salivary gland tissue and reactive cervical and axillary lymph nodes (FIG. 8). This phenotype is suggestive of early stage development of non-Hodgkin's lymphoma (NHL).

Detection of HDV in MALT Lymphoma

To identify HDV in additional lymphoma samples, a sensitive, nested qPCR assay was designed to detect HDV transcript (see Example 3), and an HDV antigen-specific antibody was used to detect HDV antigen in biopsied lymphoma tissues.

Figure 9:
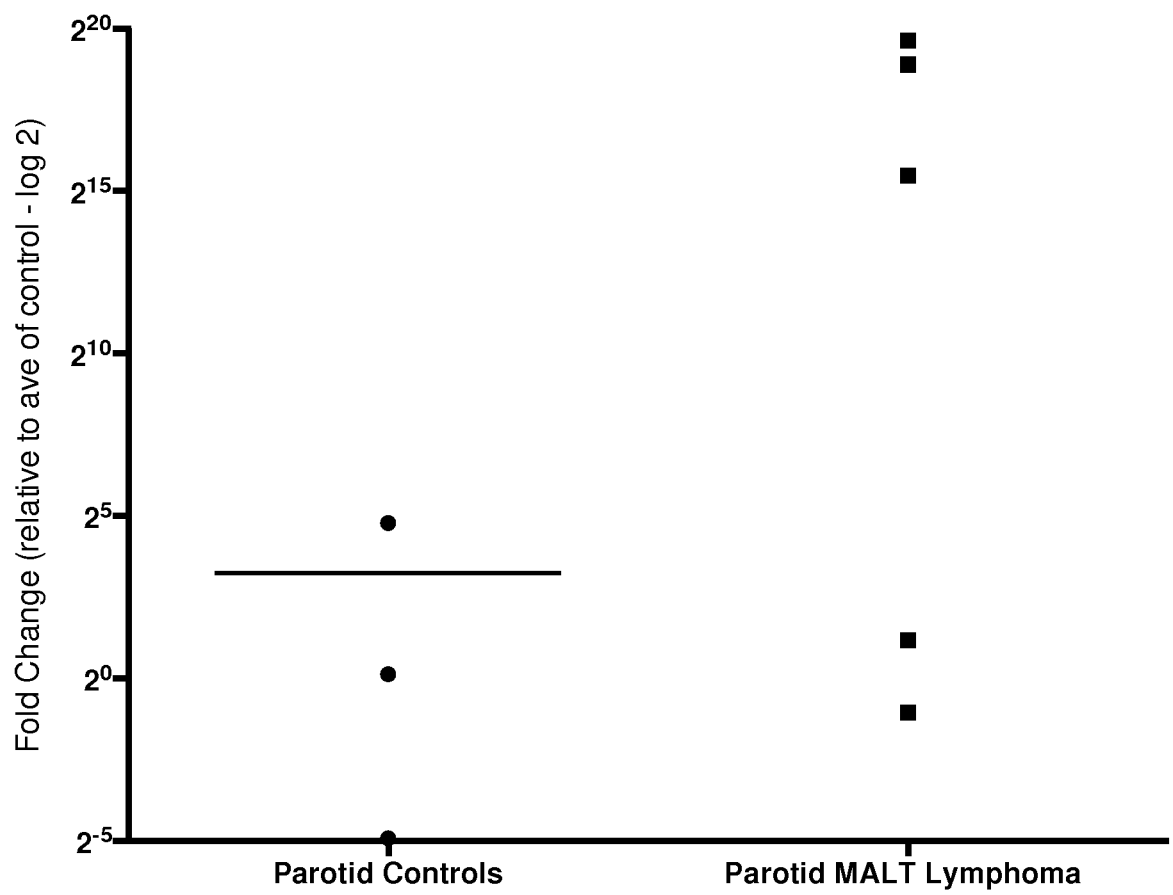
FIG. 9: HDV detected in MALT lymphoma. HDV nucleic acid was detected in three of five parotid MALT lymphoma biopsies, but was absent in parotid control tissues using the nested qPCR assay designed to detect HDV transcript and genome sequence (see Example 2). n=3-5.

Primary Sjögren's syndrome (pSS) patients that had developed NHL were analyzed for the presence of HDV antigen and (2) the presence of HDV sequence in RNA isolated from NHL mucosa-associated lymphoid tissue (MALT) tumor biopsies. As shown in FIG. 9, HDV nucleic acid was present in three of five parotid MALT lymphoma biopsies, but was absent in parotid control tissues using the nested qPCR assay designed to detect HDV transcript and genome sequence.

Figure 10A:
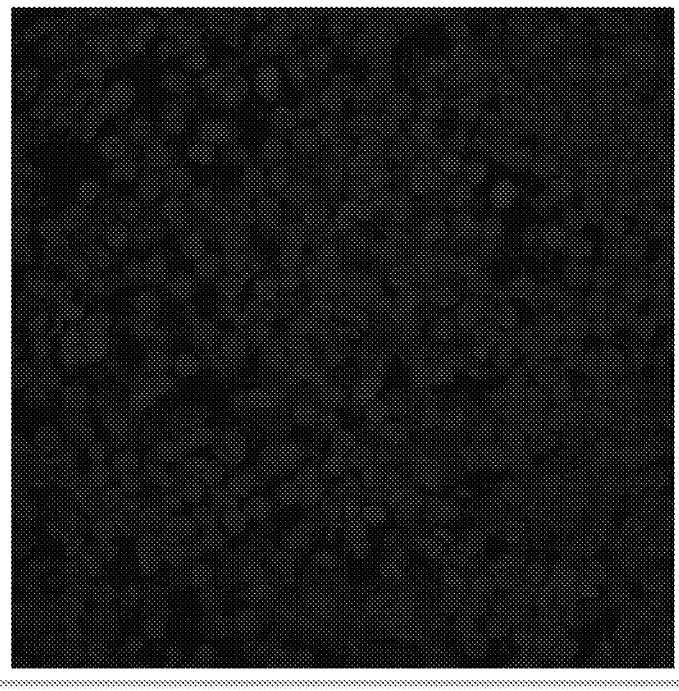
FIGS. 10A-10B: Detection of HDAg in submandibular MALT lymphoma. HDV antigen (HDAg) was detected in formalin-fixed paraffin-embedded biopsied tissue from submandibular MALT lymphoma (FIG. 10B). Rabbit IgG (RbIgG) was used as an isotype control (FIG. 10A).
Figure 10B:
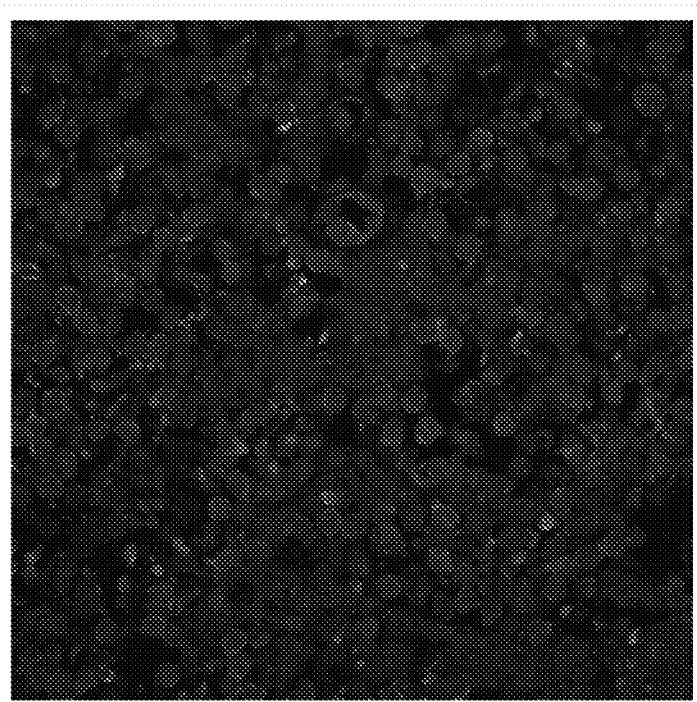
Figure 11:
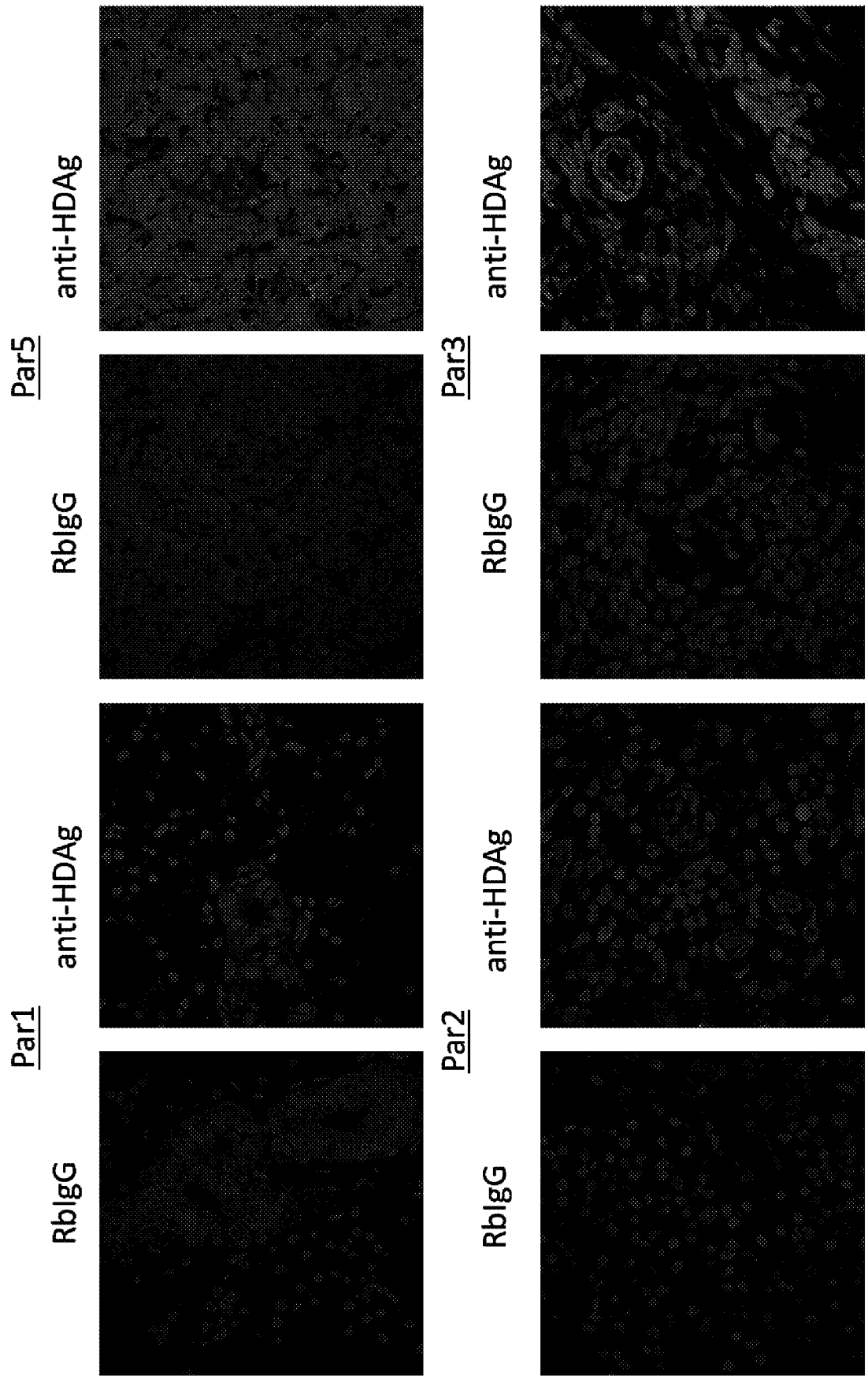
FIG. 11: Detection of HDAg in parotid MALT lymphoma. HDAg was detected in formalin-fixed paraffin-embedded biopsied tissue from parotid MALT lymphoma. Par3 and Par 5 are tissue from parotid MALT lymphoma. Par1 and Par2 are control parotid tissues. Rabbit IgG (RbIgG) was used as an isotype control.

Immunohistochemical staining also detected HDAg in biopsy tissue of a patient with submandibular MALT lymphoma (FIG. 10), and biopsied tissue from two patients with parotid MALT lymphoma (FIG. 11).

The results of the studies to detect HDV nucleic acid and antigen in MALT lymphoma biopsies are summarized in Table 3.

TABLE 3

HDV detected in MALT lymphoma. (A) RNA isolated from parotid MALT lymphoma tested positive for HDV sequence using the nested qPCR-based test designed to detect a region of HDV transcript and genome (see Example 3). Of the samples tested, 3 of 5 parotid MALT lymphoma biopsies tested positive for HDV sequence. (B) HDV antigen was detected in 2 of 2 formalin-fixed paraffin-embedded lymphoma tumors evaluated for the presence of HDV antigen. The two parotid tissue negative controls were negative for HDV antigen in comparison to lymphoma tissues.

A. HDV Sequence Results

| Sample Type | Sample | Cycle threshold (Ct) | HDV Pos/Neg |
|---|---|---|---|
| Parotid MALT | par1 | 14.65 | Positive |
| Parotid MALT | par4 | 35.97 | Negative |
| Parotid MALT | par8 | 15.16 | Positive |
| Parotid MALT | par10 | 34.26 | Negative |
| Parotid MALT | par17 | 15.41 | Positive |
| Parotid cancer control | par12 | 40.00 | Negative |
| Parotid cancer control | par16 | 33.39 | Negative |
| Parotid cancer control | par21 | 33.13 | Negative |
| Parotid cancer control | par22 | 36.22 | Negative |

B. HDV Antigen Tissue Results

| Tissue | Sample | Sample Type | HDAg Pos/Neg |
|---|---|---|---|
| Parotid MALT | par1 | Control | Negative |
| Parotid MALT | par2 | Control | Negative |
| Parotid MALT | par3 | Lymphoma | Positive |
| Parotid MALT | par4 | Lymphoma | Negative (Non-viable fat tissue) |
| Parotid MALT | par5 | Lymphoma | Positive |
| Submandibular gland MALT | 109 | Lymphoma | Positive |

These results demonstrate that HDV antigen and nucleic acid is present in patients diagnosed with pSS-associated NHL, as well as NHL not associated with Sjögren's syndrome. In addition, these data indicate that patients with or without Sjögren's syndrome and testing positive for the presence of HDV are at greater risk for developing lymphoma than patients testing negative for HDV.

Example 3: Nested PCR Assay for Detection of HDV Genome and/or Transcript

This example describes a sensitive, nested qPCR assay developed to detect HDV transcript and/or HDV genome in patient samples. Previous assays used to detect HDV in the classic HDV:HBV co-infection were designed to detect HDV genome sequence in the presence of high viral genome copy number. The present assay is focused on detection of the transcript region and incorporates nested primers sets which greatly increase the specificity and sensitivity of the assay. In contrast to previously described PCR assays for detection of HDV, the qPCR assay disclosed herein is designed to amplify regions of HDV present in both genomic, antigenomic and transcript viral sequences and incorporates nested primer and probe set to increased specificity and sensitivity of assay.

The assay described below was used in the HDV nucleic acid detection studies described in Example 2.

RNA Isolation and Reverse Transcription

RNA was isolated from salivary gland or lymphoma tumor biopsy using Qiagen RNEASY™ Mini Kit. Synthesis of cDNA was performed with 100 ng of isolated RNA using SUPERSCRIPT™ II Reverse Transcriptase or SUPERSCRIPT™ III Reverse Transcriptase (Life Technologies) and random hexamer primers (100 ng/reaction) according to the manufacturer's protocol.

Reagents

The following reagents were used in the PCR assay: HOTSTARTAQ™ Plus DNA Polymerase (Qiagen); dNTP; TAQMAN™ 2×PCR master mix (Life Technologies); and primers and probe re-suspended in PCR grade water to a concentration of 100 µM.

```
Primer MW-154-F1:
                                            (SEQ ID NO: 11)
GGCTACTCTTCTTTCCCTTCTC Primer MW-284-R1:
                                            (SEQ ID NO: 12)
ACAAGGAGAGGCAGGATCA Primer MW-174-F2:
                                            (SEQ ID NO: 13)
TCTCGTCTTCCTCGGTCAA Primer MW-251-R2:
                                            (SEQ ID NO: 14)
GCCCTCGAGAACAAGAAGAA HDV-Probe (FAM/TAMRA labeled):
                                            (SEQ ID NO: 15)
FAM/TTCCTCCTTGCTGAGGTTCTTGCC/TAMSp/
```

First Round PCR

The first found of PCR was carried out in a total volume of 25 µL containing the following reagents:

| Reagent | Volume (µL) |
|---|---|
| Q-solution | 5.0 |
| MgCl$_2$ | 3.5 |
| 10X buffer | 2.5 |
| Forward Primer (F1) | 0.125 |
| Reverse Primer (R1) | 0.125 |
| HOTSTARTAQ™ Plus DNA Polymerase | 0.25 |
| dNTP | 0.25 |
| Water | 12.25 |
| cDNA | 1.0 |

PCR conditions for the first round of PCR included one 5-minute cycle at 95° C.; 35 cycles of 30 seconds at 94° C., 30 seconds at 50° C. and 30 seconds at 72° C.; and one 10-minute cycle at 72° C. Samples were then stored at 4° C. prior to the nested PCR assay.

Nested qPCR

The nested PCR assay was carried out in a total volume of 25 µL containing the following reagents:

| Reagent | Volume (µL) |
|---|---|
| ABI TAQMAN™ Universal 2X master mix | 12.5 |
| Forward Primer (F2) | 0.125 |
| Reverse Primer (R2) | 0.125 |
| HDV Probe | 0.0625 |
| Water | 11.1875 |
| First round PCR product | 1.0 |

PCR conditions for the nested qPCR assay included one 2-minute cycle at 50° C.; one 10-minute cycle at 95° C.; and 40 cycles of 15 seconds at 95° C., 30 seconds at 50° C. and 60 seconds at 60° C.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. A method of diagnosing a subject as having Sjögren's syndrome, or susceptible to developing Sjögren's syndrome, comprising:
   detecting the presence of hepatitis delta virus (HDV) nucleic acid in a salivary gland sample obtained from the subject by performing a reverse transcriptase polymerase chain reaction (RT-PCR) assay using HDV-specific nucleic acid primers, wherein at least one of the HDV-specific nucleic acid primers comprises the nucleotide sequence of SEQ ID NO: 3, SEQ ID NO: 4, SEQ ID NO: 11, SEQ ID NO: 12, SEQ ID NO: 13 or SEQ ID NO: 14;
   detecting the presence of auto-antibodies to Ro(SSA) and/or La(SSB) in a blood or serum sample obtained from the subject, or detecting accumulation of focal lymphocytic infiltrates in the salivary gland sample obtained from the subject; and
   diagnosing the subject as having Sjögren's syndrome, or susceptible to developing Sjögren's syndrome, if HDV nucleic acid is detected in the salivary gland sample and (i) auto-antibodies to Ro(SSA) and/or La(SSB) are detected in the blood or serum sample; or (ii) accumulation of focal lymphocytic infiltrates is detected in the salivary gland sample.

2. The method of claim 1, wherein the RT-PCR assay comprises a nested PCR assay comprising a first round of PCR using a first pair of oligonucleotide primers and a second round of PCR using a second pair of oligonucleotide primers.

3. The method of claim 2, wherein the nested PCR assay amplifies HDV transcript if HDV is present in the sample.

4. The method of claim 3, wherein the first pair of oligonucleotide primers comprises the sequences of SEQ ID NO: 11 and SEQ ID NO: 12.

5. The method of claim 3, wherein the second pair of oligonucleotide primers comprises the sequences of SEQ ID NO: 13 and SEQ ID NO: 14.

6. The method of claim 3, wherein the HDV transcript is detected using a probe comprising SEQ ID NO: 15.

7. The method of claim 1, further comprising detecting the absence of hepatitis B virus (HBV)-specific antibodies in a blood or serum sample obtained from the subject.

8. The method of claim 1, further comprising detecting the absence of HDV-specific antibodies in a blood or serum sample obtained from the subject.

9. The method of claim 1, wherein the salivary gland is a minor labial salivary gland, parotid gland or a submandibular gland.

10. The method of claim 1, further comprising administering an appropriate therapy to the subject diagnosed as having Sjögren's syndrome, wherein the appropriate therapy comprises administering an agent that promotes salivary production, administering a corticosteroid, administering an immunosuppressive drug, administering a non-steroidal anti-inflammatory drug, or any combination thereof.

11. A method of diagnosing a subject as having Sjögren's syndrome, and treating the subject, comprising:
    detecting the presence of hepatitis delta virus (HDV) nucleic acid in a salivary gland sample obtained from the subject;
    detecting the presence of auto-antibodies to Ro(SSA) and/or La(SSB) in a blood or serum sample obtained from the subject, or detecting accumulation of focal lymphocytic infiltrates in the salivary gland sample obtained from the subject;
    diagnosing the subject as having Sjögren's syndrome if HDV nucleic acid is detected in the salivary gland sample and additionally (i) auto-antibodies to Ro(SSA) and/or La(SSB) are detected in the blood or serum sample; or (ii) accumulation of focal lymphocytic infiltrates is detected in the salivary gland sample; and
    administering an appropriate therapy to the subject diagnosed as having Sjögren's syndrome, wherein the appropriate therapy comprises administering an agent that promotes salivary production, administering a corticosteroid, administering an immunosuppressive drug, administering a non-steroidal anti-inflammatory drug, or any combination thereof.

12. The method of claim 11, wherein the method comprises detecting HDV nucleic acid by performing a reverse transcriptase polymerase chain reaction (RT-PCR) assay using HDV-specific nucleic acid primers.

13. The method of claim 12, wherein the HDV-specific nucleic acid primers comprise the nucleotide sequence of SEQ ID NO: 3, SEQ ID NO: 4, SEQ ID NO: 11, SEQ ID NO: 12, SEQ ID NO: 13 or SEQ ID NO: 14.

14. The method of claim 12, wherein the RT-PCR assay comprises a nested PCR assay comprising a first round of PCR using a first pair of oligonucleotide primers and a second round of PCR using a second pair of oligonucleotide primers.

15. The method of claim 14, wherein the nested PCR assay amplifies HDV transcript if HDV is present in the sample.

16. The method of claim 15, wherein the first pair of oligonucleotide primers comprises the sequences of SEQ ID NO: 11 and SEQ ID NO: 12.

17. The method of claim 15, wherein the second pair of oligonucleotide primers comprises the sequences of SEQ ID NO: 13 and SEQ ID NO: 14.

18. The method of claim 15, wherein the HDV transcript is detected using a probe comprising SEQ ID NO: 15.

19. The method of claim 11, further comprising detecting the absence of hepatitis B virus (HBV)-specific antibodies in a blood or serum sample obtained from the subject.

20. The method of claim 11, further comprising detecting the absence of HDV-specific antibodies in a blood or serum sample obtained from the subject.

21. The method of claim 11, wherein the salivary gland is a minor labial salivary gland, parotid gland or a submandibular gland.

22. A method of diagnosing a subject as having non-Hodgkin's lymphoma, and treating the subject, comprising:
    detecting the presence of hepatitis delta virus (HDV) nucleic acid in a salivary gland sample obtained from the subject, wherein the method comprises detecting HDV nucleic acid by performing a reverse transcriptase polymerase chain reaction (RT-PCR) assay using HDV-specific nucleic acid primers;
    detecting the presence of tertiary lymphoid structures in the salivary gland sample obtained from the subject;
    diagnosing the subject as having non-Hodgkin's lymphoma if HDV nucleic acid and tertiary lymphoid structures are detected in the salivary gland sample; and
    administering an appropriate therapy to the subject diagnosed with non-Hodgkin's lymphoma, wherein the appropriate therapy comprises radiation, chemotherapy, stem cell transplant, immunotherapy, surgery or any combination thereof.

23. The method of claim 22, wherein the non-Hodgkin's lymphoma comprises mucosa-associated lymphoid tissue (MALT) lymphoma.

24. The method of claim 22, wherein the HDV-specific nucleic acid primers comprise the nucleotide sequence of SEQ ID NO: 3, SEQ ID NO: 4, SEQ ID NO: 11, SEQ ID NO: 12, SEQ ID NO: 13 or SEQ ID NO: 14.

25. The method of claim 22, wherein the RT-PCR assay comprises a nested PCR assay comprising a first round of PCR using a first pair of oligonucleotide primers and a second round of PCR using a second pair of oligonucleotide primers.

26. The method of claim 22, wherein the salivary gland is a minor labial salivary gland, parotid gland or a submandibular gland.

27. A method of diagnosing a subject as susceptible to developing non-Hodgkin's lymphoma, comprising:
    detecting the presence of hepatitis delta virus (HDV) nucleic acid in a salivary gland sample obtained from the subject by performing a reverse transcriptase polymerase chain reaction (RT-PCR) assay using HDV-specific nucleic acid primers, wherein at least one of the HDV-specific nucleic acid primers comprises the nucleotide sequence of SEQ ID NO: 3, SEQ ID NO: 4, SEQ ID NO: 11, SEQ ID NO: 12, SEQ ID NO: 13 or SEQ ID NO: 14;
    detecting the presence of tertiary lymphoid structures in the salivary gland sample obtained from the subject; and
    diagnosing the subject as susceptible to developing non-Hodgkin's lymphoma if HDV nucleic acid and tertiary lymphoid structures are detected in the sample.

28. The method of claim 27, wherein the RT-PCR assay comprises a nested PCR assay comprising a first round of PCR using a first pair of oligonucleotide primers and a second round of PCR using a second pair of oligonucleotide primers.

29. The method of claim 27, wherein the salivary gland is a minor labial salivary gland, parotid gland or a submandibular gland.

* * * * *